(12) United States Patent
West et al.

(10) Patent No.: US 11,814,750 B2
(45) Date of Patent: Nov. 14, 2023

(54) COMPOSITIONS, METHODS AND SYSTEMS FOR PROCESSING OR ANALYZING MULTI-SPECIES NUCLEIC ACID SAMPLES

(71) Applicant: Personalis, Inc., Menlo Park, CA (US)

(72) Inventors: John West, Cupertino, CA (US); Richard Chen, Menlo Park, CA (US); Christian Haudenschild, Menlo Park, CA (US); Gabor Bartha, Menlo Park, CA (US); Shujun Luo, Menlo Park, CA (US)

(73) Assignee: Personalis, Inc., Fremont, CA (US)

( * ) Notice: Subject to any disclaimer, the term of this patent is extended or adjusted under 35 U.S.C. 154(b) by 344 days.

(21) Appl. No.: 16/953,758

(22) Filed: Nov. 20, 2020

(65) Prior Publication Data

US 2021/0246510 A1 Aug. 12, 2021

Related U.S. Application Data

(63) Continuation of application No. PCT/US2019/034023, filed on May 24, 2019, which is a continuation-in-part of application No. 16/056,982, filed on Aug. 7, 2018, now Pat. No. 10,801,064.

(60) Provisional application No. 62/678,475, filed on May 31, 2018.

(51) Int. Cl.
| C40B 30/04 | (2006.01) |
| C40B 20/04 | (2006.01) |
| C12Q 1/6886 | (2018.01) |
| C12Q 1/70 | (2006.01) |
| C12Q 1/689 | (2018.01) |

(52) U.S. Cl.
CPC .............. *C40B 20/04* (2013.01); *C12Q 1/689* (2013.01); *C12Q 1/6886* (2013.01); *C12Q 1/701* (2013.01); *C40B 30/04* (2013.01)

(58) Field of Classification Search
None
See application file for complete search history.

(56) References Cited

U.S. PATENT DOCUMENTS

| 4,458,066 A | 7/1984 | Caruthers et al. |
| 4,683,202 A | 7/1987 | Mullis |
| 4,988,617 A | 1/1991 | Landegren et al. |

(Continued)

FOREIGN PATENT DOCUMENTS

| CN | 105044108 A | 11/2015 |
| EP | 0281927 B1 | 6/1995 |

(Continued)

OTHER PUBLICATIONS

EP, Extended European Search Report for EP19810366.5, dated Mar. 4, 2022.

(Continued)

*Primary Examiner* — Christian C Boesen
(74) *Attorney, Agent, or Firm* — ORRICK, HERRINGTON & SUTCLIFFE LLP; Gargi Talukder; Alex Straughn

(57) ABSTRACT

Provided herein are compositions, methods, and systems for sample processing and/or data analysis. Sample processing may include nucleic acid sample processing and subsequent sequencing. Methods and systems of the present disclosure can be used, for example, for the analysis of a nucleic acid sample from a human, non-human, and combinations thereof.

24 Claims, 18 Drawing Sheets

(56) References Cited

U.S. PATENT DOCUMENTS

| | | |
|---|---|---|
| 5,143,854 A | 9/1992 | Pirrung et al. |
| 5,242,794 A | 9/1993 | Whiteley et al. |
| 5,299,491 A | 4/1994 | Kawada |
| 5,382,510 A | 1/1995 | Levine et al. |
| 5,412,087 A | 5/1995 | McGall et al. |
| 5,432,065 A | 7/1995 | Fuller |
| 5,472,672 A | 12/1995 | Brennan |
| 5,494,810 A | 2/1996 | Barany et al. |
| 5,641,658 A | 6/1997 | Adams et al. |
| 5,928,907 A | 7/1999 | Woudenberg et al. |
| 6,015,674 A | 1/2000 | Woudenberg et al. |
| 6,045,996 A | 4/2000 | Cronin et al. |
| 6,582,938 B1 | 6/2003 | Su et al. |
| 6,754,655 B1 | 6/2004 | Segal |
| 6,818,395 B1 | 11/2004 | Quake et al. |
| 7,169,560 B2 | 1/2007 | Lapidus et al. |
| 7,211,390 B2 | 5/2007 | Rothberg et al. |
| 7,211,654 B2 | 5/2007 | Gao et al. |
| 7,244,559 B2 | 7/2007 | Rothberg et al. |
| 7,264,929 B2 | 9/2007 | Rothberg et al. |
| 7,280,922 B2 | 10/2007 | Mei et al. |
| 7,282,337 B1 | 10/2007 | Harris |
| 7,300,788 B2 | 11/2007 | Matsuzaki et al. |
| 7,323,305 B2 | 1/2008 | Leamon et al. |
| 7,335,762 B2 | 2/2008 | Rothberg et al. |
| 7,361,488 B2 | 4/2008 | Fan et al. |
| 7,534,561 B2 | 5/2009 | Sana et al. |
| 7,582,420 B2 | 9/2009 | Oliphant et al. |
| 7,785,783 B2 | 8/2010 | Morley et al. |
| 7,803,550 B2 | 9/2010 | Makarov et al. |
| 8,026,094 B2 | 9/2011 | Green et al. |
| 8,140,270 B2 | 3/2012 | Kingsmore et al. |
| 8,415,101 B2 | 4/2013 | Garner |
| 8,417,459 B2 | 4/2013 | Reese et al. |
| 8,532,930 B2 | 9/2013 | Rabinowitz et al. |
| 8,589,175 B2 | 11/2013 | Glauser et al. |
| 8,785,353 B2 | 7/2014 | Van Eijk et al. |
| 8,862,410 B2 | 10/2014 | Hatchwell et al. |
| 9,109,256 B2 | 8/2015 | Shuber |
| 9,128,861 B2 | 9/2015 | Bartha et al. |
| 9,183,496 B2 | 11/2015 | Harris et al. |
| 9,228,232 B2 | 1/2016 | Faham et al. |
| 9,416,422 B2 | 8/2016 | Cheung |
| 9,453,257 B2 | 9/2016 | Hoyal-Wrightson et al. |
| 9,512,485 B2 | 12/2016 | Richardson et al. |
| 9,725,755 B2 | 8/2017 | Poole et al. |
| 9,727,692 B2 | 8/2017 | Harris et al. |
| 9,745,626 B2 | 8/2017 | Bartha et al. |
| 9,909,186 B2 | 3/2018 | Schultz |
| 10,032,000 B1 | 7/2018 | Harris et al. |
| 10,125,399 B2 | 11/2018 | West |
| 10,174,375 B2 | 1/2019 | Lo et al. |
| 10,255,330 B2 | 3/2019 | Chandratillake et al. |
| 10,262,103 B2 | 4/2019 | Lehrer et al. |
| 10,266,890 B2 | 4/2019 | Bartha et al. |
| 10,415,091 B2 | 9/2019 | Bartha et al. |
| 10,450,611 B2 | 10/2019 | West et al. |
| 10,597,717 B2 | 3/2020 | Maguire et al. |
| 10,711,306 B2 | 7/2020 | Shiina et al. |
| 10,738,355 B2 | 8/2020 | Sahin et al. |
| 10,741,269 B2 | 8/2020 | Chudova et al. |
| 10,801,064 B2 | 10/2020 | West et al. |
| 10,801,070 B2 | 10/2020 | Clement et al. |
| 10,900,088 B2 | 1/2021 | Vogelstein et al. |
| 11,047,006 B2 | 6/2021 | Salk et al. |
| 11,062,789 B2 | 7/2021 | Chiu et al. |
| 11,124,824 B2 | 9/2021 | Sarwal et al. |
| 11,142,797 B2 | 10/2021 | Moynahan et al. |
| 11,155,867 B2 | 10/2021 | Bartha et al. |
| 11,286,530 B2 | 3/2022 | Rabinowitz et al. |
| 11,345,968 B2 | 5/2022 | Mortimer et al. |
| 2002/0006615 A1 | 1/2002 | Goldsborough et al. |
| 2002/0164629 A1 | 11/2002 | Quake et al. |
| 2003/0096011 A1 | 5/2003 | Tracy |
| 2003/0099964 A1 | 5/2003 | Patil et al. |
| 2003/0220777 A1 | 11/2003 | Kitchen et al. |
| 2005/0042668 A1 | 2/2005 | Perlin |
| 2005/0086035 A1 | 4/2005 | Peccoud et al. |
| 2005/0250125 A1 | 11/2005 | Novakoff |
| 2005/0260645 A1 | 11/2005 | Green et al. |
| 2006/0184489 A1 | 8/2006 | Weiner et al. |
| 2006/0278241 A1 | 12/2006 | Ruano |
| 2007/0111247 A1 | 5/2007 | Stephens et al. |
| 2007/0184436 A1 | 8/2007 | Myerson et al. |
| 2009/0026082 A1 | 1/2009 | Rothberg et al. |
| 2009/0029364 A1 | 1/2009 | Zirwes et al. |
| 2009/0127589 A1 | 5/2009 | Rothberg et al. |
| 2009/0183268 A1 | 7/2009 | Kingsmore et al. |
| 2009/0191565 A1 | 7/2009 | Lapidus et al. |
| 2009/0326832 A1 | 12/2009 | Heckerman et al. |
| 2010/0029498 A1 | 2/2010 | Gnirke et al. |
| 2010/0035252 A1 | 2/2010 | Rothberg et al. |
| 2010/0042438 A1 | 2/2010 | Moore et al. |
| 2010/0137143 A1 | 6/2010 | Rothberg et al. |
| 2010/0188073 A1 | 7/2010 | Rothberg et al. |
| 2010/0197507 A1 | 8/2010 | Rothberg et al. |
| 2010/0282617 A1 | 11/2010 | Rothberg et al. |
| 2010/0300559 A1 | 12/2010 | Schultz et al. |
| 2010/0300895 A1 | 12/2010 | Nobile et al. |
| 2010/0301398 A1 | 12/2010 | Rothberg et al. |
| 2010/0304982 A1 | 12/2010 | Hinz et al. |
| 2011/0004413 A1 | 1/2011 | Carnevali et al. |
| 2011/0009296 A1 | 1/2011 | Kain et al. |
| 2011/0184896 A1 | 7/2011 | Guyon |
| 2012/0058480 A1 | 3/2012 | Lewis et al. |
| 2012/0077682 A1 | 3/2012 | Bowcock et al. |
| 2012/0116688 A1 | 5/2012 | Bhubaneswar et al. |
| 2012/0143512 A1 | 6/2012 | Reese et al. |
| 2012/0270206 A1 | 10/2012 | Ginns et al. |
| 2013/0073217 A1 | 3/2013 | Dewey et al. |
| 2013/0090908 A1 | 4/2013 | Dewey et al. |
| 2013/0096011 A1 | 4/2013 | Rava et al. |
| 2013/0124100 A1 | 5/2013 | Drmanac et al. |
| 2013/0173177 A1 | 7/2013 | Pelleymounter |
| 2013/0178389 A1 | 7/2013 | Lapidus et al. |
| 2013/0296535 A1 | 11/2013 | Church et al. |
| 2013/0311448 A1 | 11/2013 | Thompson |
| 2013/0332081 A1 | 12/2013 | Reese et al. |
| 2014/0200147 A1 | 7/2014 | Bartha et al. |
| 2015/0051087 A1 | 2/2015 | Rabinowitz et al. |
| 2015/0057160 A1 | 2/2015 | Breuer et al. |
| 2016/0019341 A1 | 1/2016 | Harris et al. |
| 2016/0032396 A1 | 2/2016 | Diehn et al. |
| 2016/0041987 A1 | 2/2016 | Lapir et al. |
| 2016/0092631 A1 | 3/2016 | Yandell et al. |
| 2016/0122831 A1 | 5/2016 | West |
| 2016/0283484 A1 | 9/2016 | Chandratillake et al. |
| 2017/0199961 A1 | 7/2017 | Yelensky et al. |
| 2017/0253921 A1 | 9/2017 | Liu et al. |
| 2017/0356053 A1 | 12/2017 | Otto et al. |
| 2018/0051338 A1 | 2/2018 | West et al. |
| 2018/0203974 A1 | 7/2018 | Venn |
| 2018/0258489 A1 | 9/2018 | Danenberg |
| 2018/0363066 A1 | 12/2018 | Chalmers et al. |
| 2019/0211406 A1 | 7/2019 | Babiarz et al. |
| 2019/0285518 A1 | 9/2019 | Lu et al. |
| 2020/0024669 A1 | 1/2020 | Spetzler et al. |
| 2020/0048711 A1 | 2/2020 | Snyder |
| 2020/0202224 A1 | 6/2020 | Lanman et al. |
| 2021/0054452 A1 | 2/2021 | West et al. |
| 2021/0062258 A1 | 3/2021 | Bartha et al. |
| 2021/0062276 A1 | 3/2021 | West |
| 2021/0238677 A1 | 8/2021 | West et al. |
| 2021/0398609 A1 | 12/2021 | Sigurjonsson et al. |

FOREIGN PATENT DOCUMENTS

| | | |
|---|---|---|
| EP | 1342794 B1 | 9/2003 |
| EP | 3212808 | 9/2017 |
| EP | 2861788 B1 | 10/2018 |
| WO | WO-2000018957 A1 | 4/2000 |
| WO | WO 2005098046 A2 | 10/2005 |
| WO | WO-2007055244 A1 | 5/2007 |
| WO | WO 2010054589 A1 | 5/2010 |

(56) References Cited

FOREIGN PATENT DOCUMENTS

| | | |
|---|---|---|
| WO | WO-2011050341 A1 | 4/2011 |
| WO | WO 2011/057094 A1 | 5/2011 |
| WO | WO-2011057061 A1 | 5/2011 |
| WO | WO-2011091046 A1 | 7/2011 |
| WO | WO-2011160063 A2 | 12/2011 |
| WO | WO-2011160206 A1 | 12/2011 |
| WO | WO-2012142611 A2 | 10/2012 |
| WO | WO-2014053295 A1 | 4/2014 |
| WO | WO-2014062717 A1 | 4/2014 |
| WO | WO-2014113204 A1 | 7/2014 |
| WO | WO-2014207245 A1 | 12/2014 |
| WO | WO-2015051275 A1 | 4/2015 |
| WO | WO-2016070131 | 5/2016 |
| WO | WO-2017205823 A1 | 11/2017 |
| WO | WO 2018/053365 A1 | 3/2018 |
| WO | WO-2019231856 A1 | 12/2019 |

OTHER PUBLICATIONS

Bent, et al., "Enriching pathogen transcripts from infected samples: A capture-based approach to enhanced host-pathogen RNA sequencing", Analytical Biochemistry, Jul. 1, 2013; vol. 438, No. 1, pp. 90-96, XP055220731, DOI: 10.1016/j.ab.2013.03.008. * abstract; pp. 91-92 "Material and Methods" *.

Yu et al., "Mung Bean Nuclease Treatment Increases Capture Specificity of Microdroplet-PCR Based Targeted DNA Enrichment", PLOS ONE, Jul. 24, 2014, vol. 9, No. 7, p. e103491, XP055462530, DOI: 10.1371/journal.pone.0103491. * abstract *.

Ausubel, et al. eds. Current Protocols in Molecular Biology. United States. Greene Publishing Associates and Wiley-Interscience. 1987. (Table of Contents).

Chang, et al., Role of Bacteria in Oncogenesis. Clinical Microbiology Reviews, Oct. 2010; vol. 23 No. 4: p. 837-857.

Data Sciences Platform @ Broad Institute. (2019). Genome Analysis ToolkitVariant Discovery in High-Throughput Sequencing Data. Retrieved from https://www.broadinstitute.org/gatk.

Freshney. Culture of Animal Cells: A Manual of Basic Technique and Specialized Applications. 6th Edition. 2010.

Gnirke, et al. Solution Hybrid Selection with Ultra-long Oligonucleotides for Massively Parallel Targeted Sequencing. Nat. Biotechnol. (Feb. 1, 2009), 27(2):182-9.

Li H.*, Handsaker B.*, Wysoker A., Fennell T., Ruan J., Homer N., Marth G., Abecasis G., Durbin R. and 1000 Genome Project Data Processing Subgroup (2009) The Sequence alignment/map (SAM) format and SAMtools. Bioinformatics, 25, 2078-9. [PMID: 19505943].

Moore, et al., Direct screening of blood by PCR and pyrosequencing for a 16S rRNA gene target from emergency department and intensive care unit patients being evaluated for bloodstream infection. Journal of clinical microbiology. Jan. 2016; 54(1): 99-105.

Novocraft. (2014). Retrieved from http://www.novocraft.com/.

PCT/US2019/034023 International Search Report and Written Opinion dated Aug. 16, 2019.

Sambrook, et al. Molecular Cloning: A Laboratory Manual. 4th Edition, 2012.

Stevanovic et al., Landscape of immunogenic tumor antigens in successful immunotherapy of virally induced epithelial cancer. Science, Apr. 14, 2017, vol. 356, No. 6334, pp. 200-205 Especially abstract, p. 1, 2, 15, Fig. S1.

Sudhakar, et al., Characterization of clonal immunoglobulin heavy (IGH) V-D-J gene rearrangements and the complementary-determining region in South Indian patients with precursor B-cell acute lymphoblastic leukemia. Blood Research, Mar. 2017; 52(1): 55-61.

U.S. Appl. No. 16/056,982 Notice of Allowance dated Jun. 17, 2020.

U.S. Appl. No. 16/056,982 Office Action dated Aug. 7, 2019.

U.S. Appl. No. 16/056,982 Office Action dated Feb. 7, 2019.

VarScan. (2009). Retrieved from http://varscan.sourceforge.net/.

Wang, K. (2010). ANNOVAR Documentation. Retrieved from http://annovar.openbioinformatics.org/.

Adessi, et al. Solid phase Dna amplification: characterisation of primer attachment and amplification mechanisms. Nucleic Acids Res. Oct. 15, 2000;28(20):E87.

Akey et al., "Haplotypes vs. single marker linkage disequilibrium tests: what do we gain?", European Journal of Human Genetics, Apr. 20, 2001, vol. 8, pp. 291-300.

Albert, et al. Direct selection of human genomic loci by microarray hybridization. Nat Methods. Nov. 2007;4(11):903-5. Epub Oct. 14, 2007.

Alter et al., "Clinical and molecular features associated with biallelic mutations in FANCD1/BRCA2," Journal of Medical Genetics 2007;44:1-9. doi: 10.1136/jmg.2006.043257.

Anderson et al., "Next Generation DNA Sequencing and the Future of Genomic Medicine", Genes 2010, 38-69; doi:10.3390/genes1010038.

Anonymous, "Nature Definition of Mendelian Trait", Scitable by natureEDUCATION, 2014.

Arup's product "Exome Sequencing Symptom-Guided Analysis". http:--www.aruplab.com-guides-ug-tests-2006332.jsp. Accessed Oct. 1, 2014.

Asan, et al. Comprehensive comparison of three commercial human whole-exome capture platforms. Genome Biol. Sep. 28, 2011;12(9):R95. doi: 10.1186-gb-2011-12-9-r95.

Baingridge, et al. Whole exome capture in solution with 3 Gbp of data. Genome Biol. 2010;11(6):R62. doi: 10.1186-gb-2010-11-6-r62. Epub Jun. 17, 2010.

Baird, et al. Developing recombinant antibodies for biomarker detection. Cancer Biomark. 2010;6(5-6):271-9. doi: 10.3233-CBM-2009-0144.

Bamshad., "Exome sequencing as a tool for Mendelian disease gene discovery", Nature Reviews Genetics, Nov. 2011, 12, 745-755.

Beck, et al. Profile of the circulating DNA in apparently healthy individuals. Clin Chem. Apr. 2009;55(4):730-8. doi: 10.1373-clinchem.2008.113597. Epub Jan. 30, 2009.

Behjati, et al. Genome sequencing of normal cells reveals developmental lineages and mutational processes. Nature. Sep. 18, 2014;513(7518):422-5. doi: 10.1038-nature13448. Epub Jun. 29, 2014.

Benesova et al., "Mutation-based detection and monitoring of cell-free tumor DNA in peripheral blood of cancer patients", Analytical Biochemistry vol. 433, Issue 2, Feb. 15, 2013, pp. 227-234.

Bentley, et al., "Accurate whole human genome sequencing using reversible terminator chemistry," Nature. Nov. 6, 2008; 456(7218): 53-59. doi:10.1038/nature07517.

Biesecker, et al. A genomic view of mosaicism and human disease. Nat Rev Genet. May 2013; 14(5):307-20. doi: 10.1038-nrg3424.

Bischoff, et al. Cell-free fetal DNA and intact fetal cells in maternal blood circulation: implications for first and second trimester non-invasive prenatal diagnosis. Hum Reprod Update. Nov.-Dec. 2002;8(6):493-500.

Blanco et al., "Highly Efficient DNA Synthesis by the Phage phi 29 DNA polymerase", Journal of Biological Chemistry, vol. 264, No. 15, pp. 8935-8940, May 25, 1989.

Blaschko. The nerve distribution in the skin in their relation to the diseases of the skin: a report to the VII Congress of the German Society of Dermatology, held at Wroclaw 28-30. May 1901. (in German with English abstract).

Boers et al., "High-Throughput Multilocus Sequence Typing: Bringing Molecular Typing to the Next Level," PloS ONE 2012; 7(7):e39630.

Bonadona, et al. Cancer risks associated with germline mutations in MLH1, MSH2, and MSH6 genes in Lynch syndrome. JAMA. Jun. 8, 2011;305(22):2304-10. doi: 10.1001-jama.2011.743.

Boulesteix, et al. Evaluating microarray-based classifiers: an overview. Cancer Inform. 2008;6:77-97. Epub Feb. 29, 2008.

Braslavsky, et al. Sequence information can be obtained from single DNA molecules. Proc Natl Acad Sci USA. Apr. 1, 2003;100(7):3960-4. Epub Mar. 21, 2003.

Browne, et al. Increased promoter methylation in exfoliated breast epithelial cells in women with a previous breast biopsy. Epigenetics. Dec. 2011;6(12):1425-35. doi: 10.4161-epi.6.12.18280.

(56) References Cited

OTHER PUBLICATIONS

Brunstein., "In-depth coverage: some useful NGS terms", Nov. 2014, Website, 1-5.

Bryzgunova, et al. Isolation and comparative study of cell-free nucleic acids from human urine. Ann NY Acad Sci. Sep. 2006;1075:334-40.

Burrell et al., "The causes and consequences of genetic heterogeneity in cancer evolution" Nature. Sep. 19, 2013;501(7467):338-45. doi: 10.1038/nature12625.

Carlson, et al. Decoding cell lineage from acquired mutations using arbitrary deep sequencing. Nat Methods. Nov. 27, 2011;9(1):78-80. doi: 10.1038-nmeth.1781.

Cell fate map adapted from the Gilberts Developmental Biology, Fourth edition, Figure 9.1. Apr. 16, 2014. http:- -biology.stackexchange.com-questions-16555-where-does-the-fate-map-of-a-human-embryo-end.

Chan et al., "Cancer Genome Scanning in Plasma: Detection of Tumor-Associated Copy Number Aberrations, Single-Nucleotide Variants, and Tumoral Heterogeneity by Massively Parallel Sequencing", Clinical Chemistry 59:1, 211-224 (2013).

Chiu, et al. Effects of blood-processing protocols on fetal and total DNA quantification in maternal plasma. Clin Chem. Sep. 2001;47(9):1607-13.

Choi, et al. Genetic diagnosis by whole exome capture and massively parallel DNA sequencing. Proc Natl Acad Sci U S A. Nov. 10, 2009;106(45):19096-101. doi: 10.1073-pnas.0910672106. Epub Oct. 27, 2009.

Chu, Tianjiao et al., "Statistical model for whole genome sequencing and its application to minimally invasive diagnosis of fetal genetic disease", Bioinformatics, vol. 25, No. 10, 2009, pp. 1244-1250.

Clark, et al. Performance comparison of exome DNA sequencing technologies. Nat Biotechnol. Sep. 25, 2011;29(10):908-14. doi: 10.1038-nbt.1975.

Craig, et al. Identification of genetic variants using bar-coded multiplexed sequencing. Nat Methods. Oct. 2008;5(10):887-93. Epub Sep. 14, 2008.

Damani, et al. Characterization of circulating endothelial cells in acute myocardial infarction. Sci Transl Med. Mar. 21, 2012 ;4(126):126ra33. doi: 10.1126-scitranslmed.3003451.

Davies, et al., "Indications for Hematopoietic Cell Transplantation in Acute Leukemia," Biology of Blood and Marrow Transplantation 14:154-164 (2008). doi:10.1016/j.bbmt.2007.10.024.

Dawe, et al. Cell migration from baby to mother. Cell Adh Migr. Jan.-Mar. 2007;1(1):19-27. Epub Jan. 28, 2007.

Dawson, et al., "Analysis of Circulating Tumor DNA to Monitor Metastatic Breast Cancer," New England Journal of Medicine, 2013;368:1199-209; DOI:10.1056/NEJMoa1213261. Published online Mar. 13, 2013.

De La Chapelle. The incidence of Lynch syndrome. Fam Cancer. 2005;4(3):233-7.

De Mattos-Aruda et al., Circulating tumor cells and cell-free DNA as tools for managing breast cancer, Nat. Rev. Clin. Oncol 10, 377-389 (2013); published online May 28, 2013 doi:10.1038-nrclinonc.2013.80.

De Mattos-Aruda et al., "Capturing intra-tumor genetic heterogeneity by de novo mutation profiling of circulating cell-free tumor DNA: a proof of principle", Annals of Oncology, vol. 25, No. 9, Jul. 9, 2014, pp. 1729-1735.

Decathelineau, et al. The final step in programmed cell death: phagocytes carry apoptotic cells to the grave. Essays Biochem. 2003;39:105-17.

Diaz, et al. Insights into therapeutic resistance from whole-genome analyses of circulating tumor DNA. Oncotarget. Oct. 8, 2013;4(10):1856-7.

Diaz, et al. Liquid Biopsies: Genotyping Circulating Tumor DNA. JCO Feb. 20, 2014 vol. 32 No. 6 579-586.

Dressman, et al. Transforming single DNA molecules into fluorescent magnetic particles for detection and enumeration of genetic variations. Proc Natl Acad Sci U S A. Jul. 22, 2003;100(15):8817-22. Epub Jul. 11, 2003.

Drmanac et al., "Human Genome Sequencing Using Unchained Base Reads on Self-Assembling DNA Nanoarrays", Science, 327(5961), pp. 78-81, Nov. 5, 2009.

Ellinger et al., "The role of cell-free circulating DNA in the diagnosis and prognosis of prostate cancer", Urologic Oncology 29:124-129 (2011), 124-129.

Elsharawy et al., "Accurate variant detection across non-amplified and whole genome amplified DNA using targeted next generation sequencing", BMC Genomics 13(500), pp. 1-14, Sep. 20, 2012.

Elshimali, et al. The clinical utilization of circulating cell free DNA (CCFDNA) in blood of cancer patients. Int J Mol Sci. Sep. 13, 2013;14(9):18925-58. doi: 10.3390-ijms140918925.

Saeys, et al. A review of feature selection techniques in bioinformatics. Bioinformatics. Oct. 1, 2007;23(19):2507-17. Epub Aug. 24, 2007.

Saiki, et al. Analysis of enzymatically amplified beta-globin and HLA-DQ alpha DNA with allele-specific oligonucleotide probes. Nature. Nov. 13-19, 1986;324(6093):163-6.

Samuels, et al. Genetic mosaics and the germ line lineage. Genes (Basel). Apr. 17, 2015;6(2):216-37. doi: 10.3390-genes6020216.

Sandri, et al. Apoptosis, DNA damage and ubiquitin expression in normal and mdx muscle fibers after exercise. FEBS Lett. Oct. 16, 1995;373(3):291-5.

Schmitt, et al. Detection of ultra-rare mutations by next-generation sequencing. Proc Natl Acad Sci US A. Sep. 4, 2012;109(36):14508-13. doi: 10.1073-pnas.1208715109. Epub Aug. 1, 2012.

Schwarzenbach, et al. Detection and monitoring of cell-free DNA in blood of patients with colorectal cancer. Ann NY Acad Sci. Aug. 2008;1137:190-6. doi: 10.1196-annals.1448.025.

Shaw et al. Genomic analysis of circulating cell-free DNA infers breast cancer dormancy. Genome Research 22(2):220-231 (Oct. 11, 2011).

Shigemizu et al., "A practical method to detect SNVs and indels from whole genome and exome sequencing data", Scientific Reports, 3(1), pp. 1-6, Jul. 8, 2013. Main Text.

Shigemizu et al., "A practical method to detect SNVs and indels from whole genome and exome sequencing data", Scientific Reports, 3(1), pp. 1-6, Jul. 8, 2013; Supplementary Information.

Sims et al., "Sequencing depth and coverage: key considerations in genomic analyses," Nat Rev Genet. Feb. 2014;15(2):121-32. doi: 10.1038/nrg3642.

Singleton, et al. Phevor combines multiple biomedical ontologies for accurate identification of disease-causing alleles in single individuals and small nuclear families. Am J Hum Genet. Apr. 3, 2014;94(4):599-610. doi: 10.1016-j.ajhg.2014.03.010.

Smyth. Limma: linear models for microarray data. In: Bioinformatics and Computational Biology Solutions using R and Bioconductor. R. Gentleman, V. Carey, S. Dudoit, R. Irizarry, W. Huber (eds.), 2005, Springer, New York, pp. 397-420.

Snyder et al., "Genetic Basis for Clinical Response to CTLA-4 Blockade in Melanoma", Dec. 4, 2014, New England Journal of Medicine.

Soni, et al. Progress toward ultrafast DNA sequencing using solid-state nanopores. din Chem. Nov. 2007;53(11):1996-2001. Epub Sep. 21, 2007.

Spalding, et al. Retrospective birth dating of cells in humans. Cell. Jul. 15, 2005;122(1):133-43.

Stemmer, et al. Single-step assembly of a gene and entire plasmid from large Nos. of oligodeoxyribonucleotides. Gene. Oct. 16, 1995; 164(1):49-53.

Sulston, et al. Post-embryonic cell lineages of the nematode, *Caenorhabditis elegans*. Dev Biol. Mar. 1977;56(1):110-56.

Sulston, et al. The embryonic cell lineage of the nematode *Caenorhabditis elegans*. Dev Biol. Nov. 1983;100(1):64-119.

SVBio's services. http:--www.svbio.com-service-offerings-current-services. Accessed Oct. 1, 2014.

Swanton, Charles, "Plasma-derived Tumor DNA Analysis at Whole-Genome Resolution," Editorials, Clinical Chemistry 59:1, 6-8; 2013.

(56) References Cited

OTHER PUBLICATIONS

Teer et al., "Exome sequencing: the sweet spot before whole genomes", Human Molecular Genetics, 19(R2), R145-R151, Aug. 12, 2010.
Tewhey, et al. Microdroplet-based PCR enrichment for large-scale targeted sequencing. Nat Biotechnol. Nov. 2009;27(11):1025-31. doi: 10.1038-nbt.1583. Epub Nov. 1, 2009.
The Human Cell Lineage Flagship Initiative. Last updated Nov. 10, 2010. 1 page. http:--www.lineage-flagsh ip.eu-.
Tug, et al. Exercise-induced increases in cell free DNA in human plasma originate predominantly from cells of the haematopoietic lineage. Exerc Immunol Rev. 2015;21 :164-73.
Turajlic et al., "Whole genome sequencing of matched primary and metastatic acral melanomas", Genome Research, 22(2), pp. 196-207, Feb. 22, 2012. Main document.
Turajlic et al., "Whole genome sequencing of matched primary and metastatic acral melanomas", Genome Research, 22(2), pp. 196-207, Feb. 22, 2012.Supplementary Figures.
Turajlic et al., "Whole genome sequencing of matched primary and metastatic acral melanomas", Genome Research, 22(2), pp. 196-207, Feb. 22, 2012.Supplementary Tables.
Valadi, et al. Exosome-mediated transfer of mRNAs and microRNAs is a novel mechanism of genetic exchange between cells. Nat Cell Biol. Jun. 2007;9(6):654-9. Epub May 7, 2007.
Vale et al., "Does anti-EGFR therapy improve outcome in advanced colorectal cancer? A systematic review and meta-analysis", Cancer Treatment Reviews 38 (2012) 618-625.
Van Driel, et al. A text-mining analysis of the human phenome. Eur J Hum Genet. May 2006; 14(5):535-42.
Vasan, Biomarkers of cardiovascular disease: molecular basis and practical considerations. Circulation. May 16, 2006;113(19):2335-62.
Velculescu, et al. Characterization of the yeast transcriptome. Cell. Jan. 24, 1997;88(2):243-51.
Velculescu, et al. Serial analysis of gene expression. Science. Oct. 20, 1995;270(5235):484-7.
Vietsch, et al., Circulating DNA and Micro-RNA in Patients with Pancreatic Cancer, Pancreat Disord Ther. Jun. 2015; 5(2): 156. doi: 10.4172-2165-7092.1000156.
Vinay; et al., "Immune evasion in cancer: Mechanistic basis and therapeutic strategies", Seminars in Cancer Biology, Elsevier, 2015, 35, S185-S198.
Vincent, et al. Helicase-dependent isothermal DNA amplification. EMBO Rep. Aug. 2004;5(8):795-800. Epub Jul. 9, 2004.
Vos, et al. AFLP: a new technique for DNA fingerprinting. Nucleic Acids Res. Nov. 11, 1995; 23(21):4407-14.
Wagle, Nikhil et al., "High-Throughput Detection of Actionable Genomic Alterations in Clinical Tumor Samples by Targeted, Massively Parallel Sequencing", Cancer Discovery, Jan. 2012.
Walker, et al. Strand displacement amplification—an isothermal, in vitro DNA amplification technique. Nucleic Acids Res. Apr. 11, 1992 ;20(7):1691-6.
Wang, et al. Clonal evolution in breast cancer revealed by single nucleus genome sequencing. Nature. Aug. 14, 2014;512(7513):155-60. doi: 10.1038-nature13600. Epub Jul. 30, 2014.
Warren, R.L. et al., Targeted assembly of short sequence reads. PLOS One, 6(5): May 5, 2011; p. e19816, XP055347747, DOI:10.1371-journal.pone-0019816.
Wasserstrom, et al. Reconstruction of cell lineage trees in mice. PLoS One. Apr. 9, 2008;3(4):e1939. doi: 10.1371-journal.pone. 0001939.
Westin, et al. Anchored multiplex amplification on a microelectronic chip array. Nat Biotechnol. Feb. 2000;18(2):199-204.
Xiao, et al. Identifying mRNA, microRNA and protein profiles of melanoma exosomes. PLoS One. 2012;7(10):e46874. doi: 10.1371-journal.pone.0046874. Epub Oct. 9, 2012.
Yang, Yaping et al., "Clinical Whole-Exome Sequencing for the Diagnosis of Mendelian Disorders", New England Journal of Medicine, 369;16, Oct. 2, 2013.

Yeung et al., "LOH in the HLA Class I Region at 6p21 is Associated with Shorter Survival in Newly Diagnosed Glioblastoma", Clinical Cancer Research, pp. 1816-1826, Apr. 1, 2013.
Yi et al., "Sequencing of Fifty Human Exomes Reveals Adaptation to High Altitude", Science, 329(5987), pp. 75-78, Jul. 2, 2010.
Zeerleder. The struggle to detect circulating DNA. Crit Care. 2006;10(3):142. Epub May 16, 2006.
Ley et al., "DNA Sequencing of a cytogenetically normal acute myeloid leukemia genome", Nature, vol. 456|Nov. 6, 2008.
Li, et al., "Novel computational methods for increasing PCR primer design effectiveness in directed sequencing", BMC Bioinformatics. Apr. 11, 2008;9:191. doi: 10.1186-1471-2105-9-191.
Liao et al., "Targeted Massively Parallel Sequencing of Maternal Plasma DNA Permits Efficient and Unbiased Detection of Fetal Alleles", Clinical Chemistry 57:1, 92-101 (2011).
Liu, et al. Placental mosaicism for Trisomy 13: a challenge in providing the cell-free fetal DNA testing. J Assist Reprod Genet. May 2014;31(5):589-94. doi: 10.1007-s10815-014-0182-7. Epub Feb. 5, 2014.
Lizardi, et al. Mutation detection and single-molecule counting using isothermal rolling-circle amplification. Nat Genet. Jul. 1998;19(3):225-32.
Lo et al., "Presence of fetal DN in maternal plasma and serum", Lancet 1997 350 485-87.
Lo, et al. Rapid clearance of fetal DNA from maternal plasma. Am J Hum Genet. Jan. 1999;64(1):218-24.
Lou, et al. High-throughput DNA sequencing errors are reduced by orders of magnitude using circle sequencing. Proc Natl Acad Sci U SA. Dec. 3, 2013;110(49):19872-7. doi: 10.1073-pnas.1319590110. Epub Nov. 15, 2013.
Lu et al., "Cancer immunotherapy targeting neoantigens", Seminars in Immunology, Elsevier, 2016, 28, 22-27; epub Nov. 30, 2015.
Madeleine et al., "Comprehensive Analysis of HLA-A, HLA-B, HLA-C, HLA-DRB1, and HLA-DQB1 Loci and Squamous Cell Cervical Cancer Risk", Cancer Res 2008; 68 (9), May 1, 2008.
Maluf et al., The Urine microRNA profile may help profile may help monitor post-transplant renal graft function, Kidney International. Jan. 1, 2014; vol. 85. No. 2: pp. 439-449. XP055442385.
Mamanova et al., "Target-enrichment strategies for next-generation sequencing", Nature Methods, vol. 7, No. 2, Feb. 2010.
Margulies, et al. Genome sequencing in microfabricated high-density picolitre reactors. Nature. Sep. 15, 2005;437(7057):376-80. Epub Jul. 31, 2005.
Market, et al., V(D)J Recombination and the Evolution of the Adaptive Immune System. PLOS Biol. 2003; 1(1):e16. https:--doi.org-10.1371-journal.pbio.0000016.
Marsh. Pyrosequencing applications. Methods Mol Biol. 2007;373:15-24.
Masuzaki, et al. Detection of cell free placental DNA in maternal plasma: direct evidence from three cases of confined placental mosaicism. J Med Genet. Apr. 2004; 41 (4):289-92.
Mayo Clinic staff. Tests and Procedures, Urine cytology, Definition. Published Nov. 15, 2014. 3 pages. On the Mayo Clinic web site, at: http:--www.mayoclinic.org-tests-procedures-urine-cytology-basics-definition-prc-20020408.
Mercer, et al., Targeted sequencing for gene discovery and quantification using RNA captureSeq. Nat Protoc May 2014. vol. 9, No. 5, pp. 989-1009. Especially p. 990 col. 2 para 1, p. 990 Fig 2, p. 1991 Box 1, p. 992 col. 1 para 2.
Mertes et al., "Targeted enrichment of genomic DNA regions for next-generation sequencing", Briefings in Functional Genomics, vol. 10, No. 6, 374-386, Nov. 26, 2011.
Michaelson, et al. Whole-genome sequencing in autism identifies hot spots for de novo germline mutation. Cell. Dec. 21, 2012;151(7):1431-42. doi: 10.1016-j.cell.2012.11.019.
Miller, et al., Basic concepts of microarrays and potential applications in clinical microbiology. Clinical Microbiology Reviews, Oct. 2009, p. 611-633.
Misawa et al., "Significance of chromosomal alterations and mutations of the N-RAS and TP53 genes in relation to leukemogenesis of acute myeloid leukemia", Leuk Res. Jul. 1998;22(7):631-7. doi: 10.1016/s0145-2126(98)00056-3.

(56) References Cited

OTHER PUBLICATIONS

Mitra, et al. In situ localized amplification and contact replication of many individual DNA molecules. Nucleic Acids Res. Dec. 15, 1999;27(24):e34.
Moudrianakis, et al. Base sequence determination in nucleic acids with the electron microscope. 3. Chemistry and microscope of guanine-labeled DNA. Proc Natl Acad Sci U S A. Mar. 1965;53:564-71.
Muniappan, et al. The DNA polymerase beta replication error spectrum in the adenomatous polyposis coli gene contains human colon tumor mutational hotspots. Cancer Res. Jun. 1, 2002; 62 (11 ):3271-5.
Murray, et al., Improved double-stranded DNA sequencing using the linear polymerase chain reaction. Nucleic Acids Research, vol. 17, No. 21. p. 8889. Nov. 11, 1989.
Naxerova, et al. Hypermutable DNA chronicles the evolution of human colon cancer. Proc Natl Acad Sci U S A. May 6, 2014; 111(18):E1889-98. doi: 10.1073-pnas.1400179111. Epub Apr. 21, 2014.
Naxerova, et al. Using tumour phylogenetics to identify the roots of metastasis in humans. Nat Rev Clin on col. May 2015; 12(5):258-72. doi: 10.1038-nrclinonc.2014.238. Epub Jan. 20, 2015.
Newman et al., "An ultrasensitive method for quantitating circulating tumor DNA with broad patient coverage", Nat Med. May 2014 ; 20(5) 548-554. doi:10.1038/nm.3519.
Newman et al., "An ultrasensitive method for quantitating circulating tumor DNA with broad patient coverage", Nat Med. May 2014 ; 20(5) 548-554. Supplementary Excel Spreadsheet.
Newman et al., "Integrated digital error suppression for improved detection of circulating tumor DNA", Nat Biotechnol. May 2016 ; 34(5): 547-555. doi:10.1038/nbt.3520.
Ng et al., "Exome sequencing identifies the cause of a mendelian disorder", Nature Genetics, 42(1), pp. 30-35, Nov. 13, 2009.
Ng, et al. Targeted capture and massively parallel sequencing of 12 human exomes. Nature. Sep. 10, 2009;461(7261):272-6. doi: 10.1038-nature08250. Epub Aug. 16, 2009.
Nucleosome Position by MNase-seq from ENCODE-Stanford-BYU. track settings from the UC Santa Cruz Genome Browser. 2011-2012. http://hgdownload.cse.ucsc.edu-goldenPath-hg19-encodeDCC-wgEncodeSydhNsome.
Ochman, et al. Genetic applications of an inverse polymerase chain reaction. Genetics. Nov. 1988;120(3):621-3.
Ozsolak, et al. Direct RNA sequencing. Nature. Oct. 8, 2009;461(7265):814-8. doi: 10.1038-nature08390. Epub Sep. 23, 2009.
Park. Scientists Devise a Blood Test to Predict Heart Attack. Time Magazine. Mar. 22, 2012. 2 pages.
Pasaniuc, et al. Extremely low-coverage sequencing and imputation increases power for genome-wide association studies. Nat Genet. May 20, 2012;44(6):631-5. doi: 10.1038-ng.2283. With Supplementary Information.
Pierce, et al. Linear-after-the-exponential polymerase chain reaction and allied technologies. Real-time detection strategies for rapid, reliable diagnosis from single cells. Methods Mol Med. 2007;132:65-85.
Podlaha, Ondrej et al., "Evolution of the cancer genome", Trends Genet. Apr. 2012; 28(4): 155-163. doi:10.1016/j.tig.2012.01.003.
Pritchard et al., "ColoSeq Provides Comprehensive Lynch and Polyposis Syndrome Mutational Analysis Using Massively Parallel Sequencing", Journal of Molecular Diagnostics, vol. 14, No. 4, Jul. 2012.
Punnoose, et al. Molecular biomarker analyses using circulating tumor cells. PLoS One. Sep. 8, 2010;5(9):e12517.doi:10.1371-journal.pone.0012517.
Ralph, et al., Consistency of VDJ Rearrangement and Substitution Parameters Enables Accurate B Cell Receptor Sequence Annotation. PLOS computational biology, Jan. 11, 2016; 12(1): e1004409. https:--doi.org-10.1371-journal.1004409.
Richter. Fecal DNA screening in colorectal cancer. Can J Gastroenterol. Jul. 2008;22(7):631-3.

Robinson, et al. Strategies for exome and genome sequence data analysis in disease gene discovery projects. Clinical Genetics, vol. 80, No. 2, pp. 127-132 (2011) See the whole document.
Robinson; et al., "The Human Phenotype Ontology: A Tool for Annotating and Analyzing Human Hereditary Disease", The American Journal of Human Genetics, Nov. 7, 2008, 83, 610-615.
Rogozin, et al. Somatic mutation hotspots correlate with DNA polymerase eta error spectrum. Nat Immunol. Jun. 2001;2(6):530-6.
Rosenfeld, et al. Novel multi-nucleotide polymorphisms in the human genome characterized by whole genome and exome sequencing. Nucleic Acids Research, Article No. gkq408, pp. 1-10 (2010) See abstract; and pp. 8-9.
Ross, et al. Characterizing and measuring bias in sequence data. Genome Biology, vol. 14, No. 5, Article No. R51, pp. 1-20 (e-pub, May 29, 2013) See the whole document.
Ross. Introduction to Oncogenes and Molecular Cancer Medicine. Copyright 1998 Springer-Verlag New York, Inc. ISBN : 0-387-98392-9.
Esplin et al., Personalized sequencing and the future of medicine: discovery, diagnosis and defeat of disease. Pharmacogenomics. Nov. 2014. vol. 15, Nov. 14. pp. 1771-1790. Especially p. 1772 col. 2 para 3, p. 1773 col. 1 para 3, p. 1775 col. 1 para 2, p. 1776 fig 1, p. 1777 col. 1 para 1, p. 1777 col 2 para 2, p. 1783 col. 1 para 3, p. 1785 col. 1 para 1.
Fahy, et al. Self-sustained sequence replication (3SR): an isothermal transcription-based amplification system alternative to PCR. PCR Methods Appl. Aug. 1991;1 (1):25-33.
Fishel, et al. Meta-analysis of gene expression data: a predictor-based approach. Bioinformatics. Jul. 1, 2007;23(13):1599-606. Epub Apr. 26, 2007.
Forshew et al., "Noninvasive Identification and Monitoring of Cancer Mutations by Targeted Deep Sequencing of Plasma DNA", Science Translational Medicine, May 30, 2012, vol. 4, Issue 136, 136ra68; DOI: 10.1126/scitranslmed.3003726.
Forshew et al., "Noninvasive Identification and Monitoring of Cancer Mutations by Targeted Deep Sequencing of Plasma DNA", Supplementary Materials, Science Translational Medicine, May 30, 2012, vol. 4, Issue 136, 136ra68; DOI: 10.1126/scitranslmed. 3003726.
Fox, et al. Accuracy of Next Generation Sequencing Platforms. Next Gener Seq Appl. 2014;1. pii: 1000106.
Freed et al. Somatic mosaicism in the human genome. Genes 5.4 (Dec. 11, 2014): 1064-1094.
Frumkin, et al. Genomic variability within an organism exposes its cell lineage tree. PLoS Comput Biol. Oct. 2005;1 (5):e50. Epub Oct. 28, 2005.
Gilbert, Developmental Biology. 10th ed. Published by Sinauer Associates, Inc. (Sunderland, MA). Copyright 2014.
Golob, Mechanisms of cell fate acquisition in the differentiation of pluripotent stem cells. Dissertation. University of Washington. 2009; 110 pages.
Goris; et al., "The Immunogenetic Architecture of Autoimmune Disease", Cold Spring Harbor Perspectives in Biology, 2012, 4:a007260, 1-15.
Gottlieb, et al. The DiGeorge syndrome minimal critical region contains a goosecoid-like (GSCL) homeobox gene that is expressed early in human development. Am J Hum Genet. May 1997;60(5):1194-201.
Guo et al., "Exome sequencing generates high quality data in non-target regions", BMC Genomics 13(194), pp. 1-10, May 20, 2012. Main text.
Guo et al., "Exome sequencing generates high quality data in non-target regions", BMC Genomics 13(194), pp. 1-10, May 20, 2012. Supplementary Tables.
Guo et al., "Whole-genome and whole-exome sequencing of bladder cancer identifies frequent alterations in genes involved in sister chromatid cohesion and segregation", nature Genetics, Letters, vol. 45, No. 12, Dec. 2013. Published online Oct. 13, 2013.
Haferlach et al., "Mutations of the TP53 gene in acute myeloid leukemia are strongly associated with a complex aberrant karyotype", Leukemia. Aug. 2008;22(8):1539-41. doi: 10.1038/leu.2008. 143. Epub Jun. 5, 2008.

(56) References Cited

OTHER PUBLICATIONS

Hamfjord et al., Plos One at www.plosone.org Apr. 2012, vol. 7, Issue 4, e34150.

Hiratani, et al., Replication timing and transcriptional control: beyond cause and effect—part II. Curr Opin Genet Dev. Apr. 2009;19(2):142-9. doi: 10.1016-j.gde.2009.02.002. Epub Apr. 1, 2009.

Hirschhorn, et al. Human intersex with chromosome mosaicism of type XY-XO. Report of a case. N Engl J Med. Nov. 24, 1960;263:1044-8.

Holstege, et al. Somatic mutations found in the healthy blood compartment of a 115-yr-old woman demonstrate oligoclonal hematopoiesis. Genome Res. May 2014;24(5):733-42. doi: 10.1101 -gr.162131.113. Epub Apr. 23, 2014.

Hong, et al., Tracking the origins and drivers of subclonal metastatic expansion in prostate cancer. Nature Communications, Apr. 1, 2015; vol. 6, No. 1: pp. 1-12. XP055501144.

Huang, et al. Characterization of human plasma-derived exosomal RNAs by deep sequencing. BMC Genomics. May 10, 2013;14:319. doi: 10.1186-1471-2164-14-319.

Human Genome Overview GRCh37. Genome Reference Consortium, Feb. 27, 2009. 1 Page.

Human Genome Overview GRCh37.p13. Genome Reference Consortium, Jun. 28, 2013. 2 Pages.

Human Genome Overview GRCh38.p12. Genome Reference Consortium, Dec. 21, 2017. 2 Pages.

Illumina, "Coverage Depth Recommendations", Science and Education, 2018, Website, 1-3.

Illumina, "Interpreting Infinium Assay Data for Whole-Genome Structural Variation", Technical Note: DNA Analysis, 2010. Website, 1-8.

Illumina Technical Note: Informatics. Sequencing coverage information methods for human whole-genome sequencing. A overview of Illumina coverage calculation methods using BaseSpace or third party analysis tools. 2014. 2 pages.

Illumina Technical Note: Sequencing. Estimating sequencing coverage. Before starting a sequencing experiment, you should know the depth of sequencing you want to achieve. This technical note helps you estimate that coverage. 2014. 2 pages.

Ito et al., "Cancer Neoantigens: A Promising Source of Immunogens for Cancer Immunotherapy", Journal of Clinical & Cellular Immunology, Apr. 28, 2015, vol. 6, No. 2, 21559899.

Jenjaroenpun, et al. Characterization of RNA in exosomes secreted by human breast cancer cell lines using next-generation sequencing. PeerJ. Nov. 5, 2013;1 :e201. doi: 10.7717-peerj.201.eCollection 2013.

Jung et al., "Cell-free DNA in the blood as a solid tumor biomarker—A critical appraisal of the literature", Clinica Chimica Acta 411 :1611-1624 (Nov. 11, 2010).

Karam, et al. Apoptosis in Carcinogenesis and Chemotherapy. Published by Springer in 2009 ISBN: 978-1-4020-9596-2.

Kiialainen, et al. Performance of microarray and liquid based capture methods for target enrichment for massively parallel sequencing and SNP discovery. PLoS One. Feb. 9, 2011;6(2):e16486. doi: 10.1371-journal.pone.0016486.

Kinde, et al. Detection and quantification of rare mutations with massively parallel sequencing. Proc Natl Acad Sci US A. Jun. 7, 2011;108(23):9530-5. doi: 10.1073-pnas.1105422108. Epub May 17, 2011.

Koboldt et al., "VarScan: variant detection in massively parallel sequencing of individual and pooled samples", Bioinformatics, 25(17), pp. 2283-2285, Jun. 19, 2009.

Kokawa, et al. Apoptosis in the human uterine endometrium during the menstrual cycle. J Clin Endocrinol Metab. Nov. 1996;81(11):4144-7.

Koren, et al. Differential relationship of DNA replication timing to different forms of human mutation and variation. Am J Hum Genet. Dec. 7, 2012;91(6):1033-40. doi: 10.1016-j.ajhg.2012.10.018. Epub Nov. 21, 2012.

Kosuri and Church, "Large-scale de novo DNA synthesis: technologies and applications," Nature Methods, 11:499-507, May 2014. Available at: http:-www.nature.com-nmeth-journal-v11-n5-full-nmeth.2918.html.

Kothari, et al., "Emerging Technologies for Rapid Identification of Bloodstream Pathogens", Clinical Infectious Diseases, Apr. 24, 2014:59(2);272-8).

Krumm et al., "Copy number variation detection and genotyping from exome sequence data", Genome Research, 22(8), pp. 1525-1532, May 14, 2012.

Kuchler, et al. Buccal cells DNA extraction to obtain high quality human genomic DNA suitable for polymorphism genotyping by PCR-RFLP and Real-Time PCR. J Appl Oral Sci. Jul.-Aug. 2012;20(4):467-71.

Laktionov et al. "Cell-surface-bound nucleic acids: Free and cell-surface-bound nucleic acids in blood of healthy donors and breast cancer patients", Ann. NY Acad Sci 1022:221-227 (2004).

Lam, et al. Time course of early and late changes in plasma DNA in trauma patients. Clin Chem. Aug. 2003:49(8):1286-91.

Larson et al., "SomaticSniper: identification of somatic point mutations in whole genome sequencing data", Bioinformatics, 28(3), pp. 311-317, Dec. 6, 2011.

Lathe, R., Synthetic oligonucleotide probes deduced from amino acid sequence data: Theoretical and practical considerations. Journal of Molecular Biology, May 5, 1985; 183(1): 1-12.

Leamon, et al. A massively parallel PicoTiterPlate based platform for discrete picoliter-scale polymerase chain reactions. Electrophoresis. Nov. 2003; 24(21):3769-77.

Leary et al., "Development of Personalized Tumor Biomarkers Using Massively Parallel Sequencing", Science Translational Medicine, Feb. 24, 2010; 2(20): 20ra14.

Leary, et al. Detection of chromosomal alterations in the circulation of cancer patients with whole-genome sequencing. Sci Transl Med. Nov. 28, 2012;4(162):162ra154. doi: 10.1126-scitranslmed.3004742.

Levin, et al., Targeted next-generation sequencing of a cancer transcriptome enhances detection of sequence variants and novel fusion transcripts. Genome Biology, 2009. 10:R115.

Office Action for Japanese Patent Application No. 2020-566295 with English Translation, 6 pages, dated Jun. 2, 2023.

Colella et al., "QuantiSNP: an Objective Bayes Hidden-Markov Model to detect and accurately map copy number variation using SNP genotyping data", Nucleic Acids Research, 2007, vol. 35, No. 6, 2013-2025; published online Mar. 6, 2007.

Maguerat et al., "RNA Seq: from technology to biology", Cellular and Molecular Life Sciences, vol. 67, pp. 569-579; published online Oct. 27, 2009.

Pathak et al., "Circulating Cell-Free DNA in Plasma/Serum of Lung Cancer Patients as a Potential Screening and Prognostic Tool", Clinical Chemistry 52:10, 1833-1842 (2006).

COMPOSITIONS, METHODS AND SYSTEMS FOR PROCESSING OR ANALYZING MULTI-SPECIES NUCLEIC ACID SAMPLES

CROSS REFERENCE

This application is a continuation application of International Application No. PCT/US2019/034023, filed May 24, 2019, which is a continuation-in-part of U.S. patent application Ser. No. 16/056,982, filed Aug. 7, 2018, now U.S. Pat. No. 10,801,064, which claims priority to U.S. Provisional Patent Application No. 62/678,475, filed May 31, 2018, which are entirely incorporated herein by reference.

BACKGROUND

Current methods for whole genome and/or exome sequencing may be costly and fail to capture many biomedically important variants. For example, commercially available exome enrichment kits (e.g., Illumina's TruSeq exome enrichment and Agilent's SureSelect exome enrichment), may fail to target biomedically interesting non-exomic and exomic regions. Often, whole genome and/or exome sequencing using standard sequencing methods performs poorly in content regions having very high CG content (>70%). Furthermore, whole genome and/or exome sequencing also fail to provide adequate and/or cost-effective sequencing of repetitive elements in the genome.

The methods disclosed herein provide specialized sequencing protocols or technologies to address these issues and extend analysis to human and non-human genomes in a single sample.

SUMMARY

Disclosed herein is a method for processing a biological sample obtained from a subject, comprising (a) generating a subset of nucleic acid molecules from the biological sample using a pool of nucleic acid probes, wherein the probes comprise (i) a first plurality of nucleic acid probes configured to target elements of a human genome and (ii) a second plurality of nucleic acid probes configured to target elements of one or more non-human genome(s); and (b) subjecting the subset of nucleic acid molecules to an assay to yield sequence information comprising sequences of (i) human nucleic acids from the biological sample from the subject and (ii) non-human nucleic acids from the biological sample of the subject. In some cases, the first plurality of nucleic acid probes of (i) are configured to target elements derived from the human genome. In some cases, the subject can be human. In some cases, the second plurality of nucleic acid probes are configured to target elements from non-human genome sequences of one or more species selected from the group consisting of viruses, bacteria, bacterial phages, fungi, protists, archaea, amoeba, helminths, algae, genetically modified cells, and genetically modified vectors. In an aspect, generating the subset of nucleic acid molecules from the biological sample comprises conducting one or more hybridization reactions. In some cases, a method further comprising obtaining the biological sample from the subject. In some cases, the biological sample of the subject can be derived from a tumor biopsy, whole blood, or blood plasma. In some aspects, a method further comprises aligning the sequences of the subset of nucleic acid molecules to one or more reference sequences. In some cases, the one or more references sequences comprise a plurality of reference sequences. In some cases, the plurality of references sequences corresponds to two or more different species. A method can further comprise identifying sources of the nucleic acid molecules in the subset based on the alignment. In some cases, a method can further comprise generating an output comprising the identified sources of nucleic acid molecules in the biological sample. In some cases, a concentration of the second plurality of nucleic acid probes is greater than a concentration of the first plurality of nucleic acid probes in the pool of nucleic acid probes. In an aspect, a relative concentration of the second plurality of nucleic acid probes in the pool of probes is greater than a relative concentration of the first plurality of nucleic acid probes in the pool of nucleic acid probes. In an aspect, the first plurality of nucleic acid probes comprises a human exome capture probe set. In some cases, the first plurality of nucleic acid probes comprises probes configured to target junction sequences created by human V(D)J rearrangement or recombination. In some cases, the second plurality of nucleic acid probes comprises one or more probes configured to target human papilloma virus E6 gene and/or E7 gene. In some cases, the second plurality of nucleic acid probes comprises probes configured to target one or more elements of a bacterial 16S ribosomal RNA gene. In an aspect, the assay of (b) comprises performing sequencing to generate paired-end read sequences of lengths from 130 based to 280 bases. In an aspect, a method can further comprise producing one or more biomedical reports comprising one or more sets of data selected from the group consisting of: (i) candidate tumor neoantigens, (ii) detected non-human species, (iii) detected CDR3 sequences, and any combination thereof. In an aspect, the detected non-human species are antigens. In some cases, the CDR3 sequences are generated by V(D)J rearrangement or recombination. In some cases, the CDR3 sequences correspond to an immune response to an antigen. In some cases, the one or more biomedical reports comprises (i)-(iii).

Disclosed herein is a method for processing a biological sample obtained from a subject, comprising (a) generating a subset of nucleic acid molecules from the biological sample, wherein the subset of nucleic acid molecules comprises (i) a first plurality of nucleic acid molecules from the subject and (ii) a second plurality of nucleic acid molecules that are not from the subject, and wherein an abundance of the first plurality of nucleic acid molecules is greater than an abundance of the second plurality of nucleic acid molecules in the biological sample; and (b) subjecting the subset of nucleic acid molecules to an assay to yield sequence information comprising sequences of (i) the first plurality of nucleic acid molecules and (ii) the second plurality of nucleic acid molecules. In some cases, the nucleic acid molecules of (i) are derived from a genome of the subject. In some cases, the subject is human. In some cases, the second plurality of nucleic acid molecules that are not from the subject comprise one or more members selected from the group consisting of viruses, bacteria, bacterial phages, fungi, protists, archaea, amoeba, helminths, algae, genetically modified cells, and genetically modified vectors. In an aspect, generating the subset of nucleic acid molecules from the biological sample comprises conducting one or more hybridization reactions. In an aspect, a method further comprising obtaining the biological sample from the subject. In some cases, the biological sample of the subject is derived from a tumor biopsy, whole blood, or blood plasma. In an aspect, a method further comprises aligning the sequences of the subset of nucleic acid molecules to one or more reference sequences. In an aspect, the one or more references sequences comprise a plurality of reference sequences. In an aspect, the plurality of references sequences correspond to two more different species. A method can further comprise identifying sources of the nucleic acid molecules in the subset based on the alignment. In an aspect, a method further comprises generating an output comprising the identified sources of nucleic acid molecules in the biological sample. In some cases, an abundance of the first plurality of nucleic acid molecules is greater than an abundance of the first plurality of nucleic acid molecules in the biological sample. In some cases, a relative abundance of the second plurality of nucleic acid molecules in the subset is greater than a relative abundance of the first plurality of nucleic acid molecules in the subset.

Disclosed herein is a composition comprising a pool of probes configured to hybridize with (i) a one or more human sequences from a subject and (ii) one or more non-human sequences from the subject. In an aspect, the pool of probes is a plurality of capture probes. In an aspect, the pool of probes is a plurality of amplification probes.

Disclosed herein is a system for processing a biological sample of a subject, comprising: a processing unit comprising one or more computer processors that are individually or collectively programmed to subject a subset of nucleic acid molecules to an assay to yield sequence information comprising sequences of (i) human nucleic acids from the biological sample from the subject and (ii) non-human nucleic acids from the biological sample of the subject, which subset of nucleic acid molecules is generated from the biological sample using a pool of nucleic acid probes, wherein the probes comprise (i) a first plurality of nucleic acid probes configured to target elements of a human genome and (ii) a second plurality of nucleic acid probes configured to target elements of one or more non-human genome(s); and computer memory configured to store the sequence information. In some embodiments, the one or more computer processors are programmed to generate an alignment of the sequences to one or more reference sequences. In some embodiments, the one or more references sequences comprise a plurality of reference sequences, and wherein the plurality of references sequences correspond to two or more different species. In some embodiments, the one or more computer processors are programmed to identify sources of the nucleic acid molecules in the subset based on the alignment. In some embodiments, the one or more computer processors are programmed to produce one or more biomedical reports comprising information selected from the group consisting of: (i) candidate tumor neoantigens, (ii) detected non-human species, (iii) detected complementarity-determining region 3 (CDR3) sequences, and any combination thereof.

Disclosed herein is a system for processing a biological sample of a subject, comprising: a processing unit comprising one or more computer processors that are individually or collectively programmed to subject a subset of nucleic acid molecules to an assay to yield sequence information comprising sequences of (i) the first plurality of nucleic acid molecules and (ii) the second plurality of nucleic acid molecules, which subset of nucleic acid molecules is generated from the biological sample, wherein the subset of nucleic acid molecules comprises (i) a first plurality of nucleic acid molecules from the subject and (ii) a second plurality of nucleic acid molecules that are not from the subject, and wherein an abundance of the first plurality of nucleic acid molecules is greater than an abundance of the second plurality of nucleic acid molecules in the biological sample; and computer memory configured to store the sequence information. In some embodiments, the one or more computer processors are programmed to generate an alignment of the sequences to one or more reference sequences. In some embodiments, the one or more references sequences comprise a plurality of reference sequences, and wherein the plurality of references sequences correspond to two or more different species. In some embodiments, the one or more computer processors are programmed to identify sources of the nucleic acid molecules in the subset based on the alignment. In some embodiments, the one or more computer processors are programmed to produce one or more biomedical reports comprising information selected from the group consisting of: (i) candidate tumor neoantigens, (ii) detected non-human species, (iii) detected complementarity-determining region 3 (CDR3) sequences, and any combination thereof.

Another aspect of the present disclosure provides a non-transitory computer readable medium comprising machine executable code that, upon execution by one or more computer processors, implements any of the methods above or elsewhere herein.

Another aspect of the present disclosure provides a system comprising one or more computer processors and computer memory coupled thereto. The computer memory comprises machine executable code that, upon execution by the one or more computer processors, implements any of the methods above or elsewhere herein.

Additional aspects and advantages of the present disclosure will become readily apparent to those skilled in this art from the following detailed description, wherein only illustrative embodiments of the present disclosure are shown and described. As will be realized, the present disclosure is capable of other and different embodiments, and its several details are capable of modifications in various obvious respects, all without departing from the disclosure. Accordingly, the drawings and description are to be regarded as illustrative in nature, and not as restrictive.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings (also "Figure" and "FIG." herein), of which:

DETAILED DESCRIPTION

Figure 1:
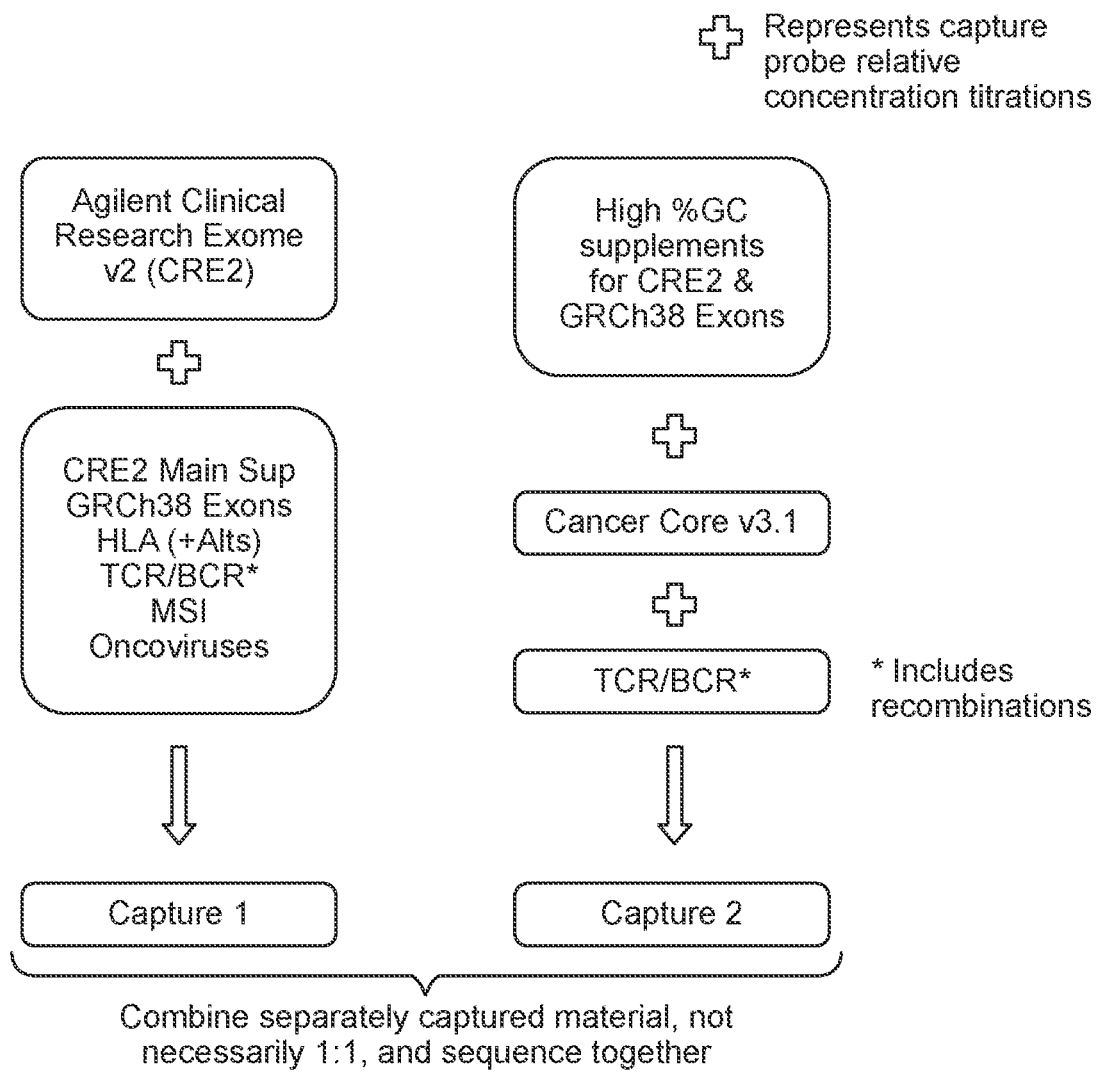
FIG. 1 schematically illustrates a method for generating a subset of nucleic acid molecules using a first plurality of nucleic acid probes and a second plurality of nucleic acid probes.

While various embodiments of the invention have been shown and described herein, it will be obvious to those skilled in the art that such embodiments are provided by way of example only. Numerous variations, changes, and substitutions may occur to those skilled in the art without departing from the invention. It should be understood that various alternatives to the embodiments of the invention described herein may be employed.

The human body frequently harbors a large number of microbial species, over 1,000 in some cases. These have been documented by the Human Microbiome Project and other studies, and can include numerous viruses, bacteria, bacterial phage, fungi, protists, archaea, and some amoeba, helminths and algae. These non-human species can be beneficial, but they can also cause or modulate diseases, including cancer. Their effects can be direct (e.g. causing mutations in human cells thus leading to cancer) or indirect (e.g. stimulating the immune system which influences its ability to fight disease). The microbial species in an individual can be identified and characterized by sequencing nucleic acids extracted from samples of the person. Many of these microbes live at the interfaces of the body with its surrounding environment (e.g. the skin, saliva, nasal passages, gut, intestine, genitals). These can be sampled from those interfaces either by swabbing, biopsy, stool or urine, saliva or similar methods. Multiple methods have been developed for sequence analysis of microbial nucleic acids from these samples. These include both targeted PCR amplification (e.g. of subsections of the 16S ribosomal RNA gene) and untargeted (metagenomic) methods that use deep sequencing. Many of these methods involve sample types and/or enrichment methods which seek to minimize the amount of human DNA, so as to optimize sensitivity to the intended microbial target. The human genome (about 3 billion bases) is about 1,000 times larger than a typical bacterial genome (less than a million bases up to a few million) and many thousands of times the size of most viral genomes (typically a few thousand up to a few tens of thousands of bases). Thus without a sampling method or assay technology to avoid or reduce it, the human DNA content can take up most of an assay's capacity.

Progression of many diseases is also influenced by genetics of human cells. This can include inherited genetic variants, somatic variants in cancer, VDJ recombination in immune cells, differential gene expression in different cell types, and other properties. These can also be assayed by sequencing of nucleic acids, typically either from the blood (most commonly PBMC's or cell-free DNA) or from diseased tissue (e.g. a tumor biopsy). Multiple methods have been developed for sequence analysis of nucleic acids from these samples, including amplicon panels (typically for up to a few hundred genes), hybrid capture (typically for large numbers of genes, including exomes) and untargeted methods (whole genome sequencing). Many of these methods involve sample types and/or enrichment methods optimized for their intended human nucleic acid target.

The sample types for microbial analysis may be different from those used for human genetic analysis. While a stool sample may be used for analysis of the gut microbiome, for example, it may be a poor sample in testing for inherited human genetic disease such as cystic fibrosis. White cells from the blood (PBMCs) may be sequenced to look for inherited genetic disease causes, but may usually be a poor choice for bacterial analysis, since the immune system largely excludes bacteria from the blood. Assay methods for human and microbial analysis also differ. Either may use PCR, for example, but since PCR yields very narrowly focused results (i.e. the amplicons each generally represent a tiny portion of the target species' genome) human and microbial targets are generally not combined in a single PCR-based assay. Untargeted assays can be used for both human genetics (i.e. whole human genome sequencing) and microbial metagenomics, but because of the huge differences in genome sizes mentioned above, it is generally optimal to assay each separately, with source material and assay optimized for each. For the same reason, hybrid capture assay technologies (e.g. exomes) have been developed for specific (generally mammalian) species (e.g. a human exome, or a bovine exome).

Cancer can be a special case. Many tumors use checkpoint genes and other methods to partially or fully exclude the immune system. Thus microbes which manage to infiltrate a tumor may be able to survive and even prosper there. Whole live bacteria (e.g. *Fusobacterium*) have been may cancer cells and live entirely within them, including through cycles of cell division and through metastasis. Bacteria may cause cancer (e.g. *Helicobacter pylori* is a cause of gastric cancer) and they can impact the progression of cancer and the response to cancer therapeutics (e.g. immune checkpoint inhibitors). Viruses may also enter cells and in some cases are the cause of cancer, and/or may integrate their genomes into the human chromosomes. Thus tumor biopsies may contain both human and microbiome species, and their nucleic acids. When these cells die, their multi-species nucleic acids may be shed into their surroundings and eventually be detectable as cell-free nucleic acids in the blood plasma.

Sample amounts from tumor biopsies are often very limited, making it more difficult to conduct multiple different assays for human vs microbial genetic targets from the same sample. An integrated assay which can provide sequence data from both human and microbiome species concurrently may be advantageous when sample amounts are limited. Cell-free DNA and RNA from blood plasma is also often quite limited in quantity. An integrated assay which can provide sequence data from both human and microbiome species concurrently from a single small plasma sample may also be advantageous.

Figure 2:
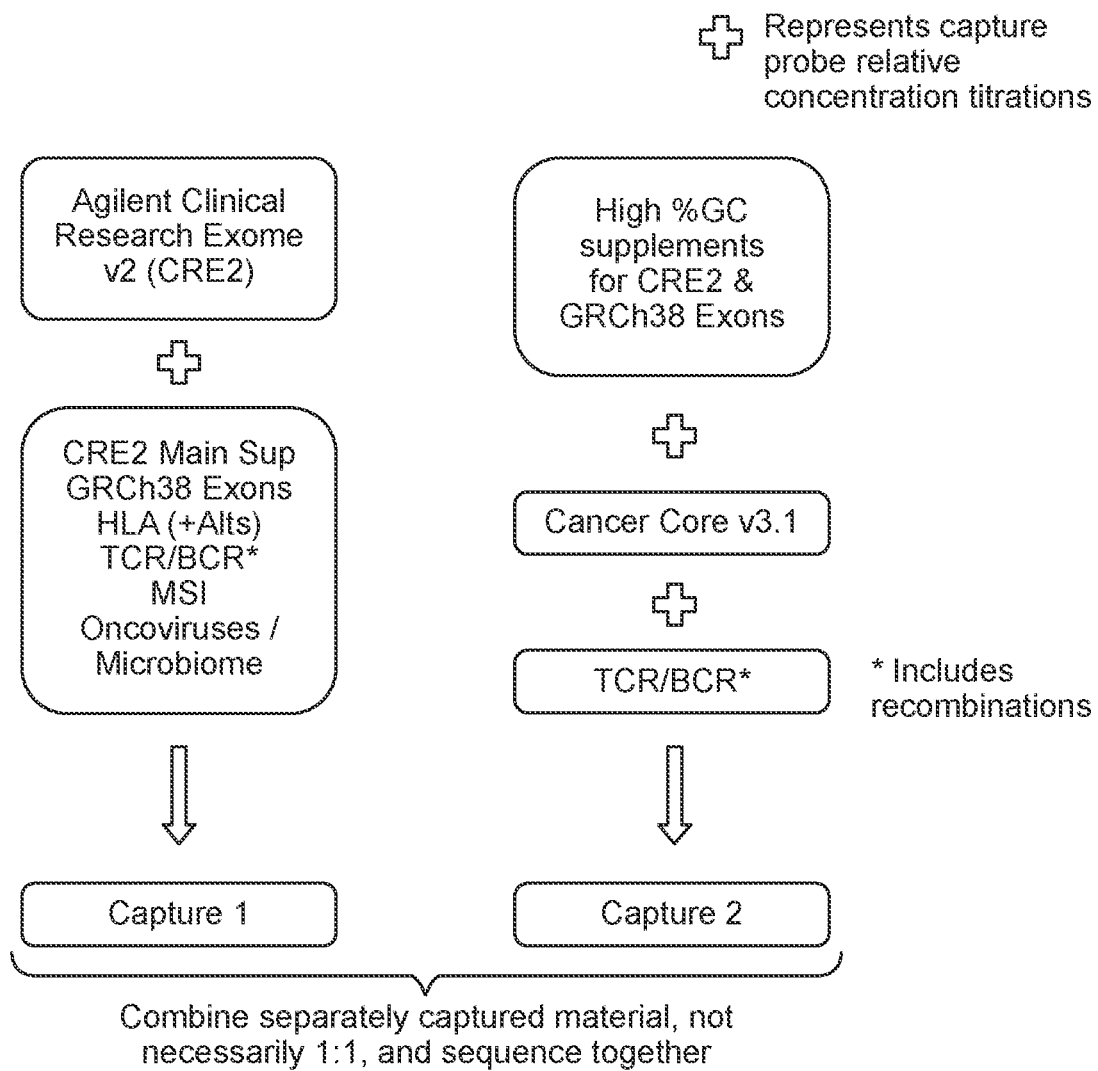
FIG. 2 schematically illustrates a method for generating a subset of nucleic acid molecules using a first plurality of nucleic acid probes and a second plurality of nucleic acid probes. The first plurality of nucleic acid probes may bind a non-human genome.

Disclosed herein is an assay which supports concurrent detection of broad human genetic data, with microbiome data from the same sample at the same time. A single assay may be performed that does not require any more sample than may be required for an equivalent human-only assay. This assay can use a human exome capture kit (e.g. Agilent Clinical Research Exome v2). A kit or composition of a pool of probes can employ hybridization probes which are complementary to the human sequences it targets. By using over 50,000 capture probes, a method, kit or composition may target the exons of a majority of predetermined human genes. For example, prior to conducting the hybridization reaction of nucleic acids from a cancer sample with the probes of this kit, we add an additional set of capture probes that we have designed to target non-human sequences. Non-human sequences can be from viral, bacterial, fungal or archeal genomes, i.e. from the human microbiome. Once human exome probes are combined with the non-human microbiome probes, that probe-mixture can be used for a single hybridization-based capture reaction with nucleic acids extracted from a patient sample (FIG. 2). After that, the nucleic acids which have been captured can be sequenced. In our laboratory, this sequencing is performed using Illumina NovaSeq-6000 DNA sequencing instruments.

Mixed (human and non-human) DNA sequences resulting from such a process can be separated out by alignment with the human and microbiome-species reference sequences. Separation of sequences by alignment is possible because the human genome has diverged very substantially from the microbial genomes over the course of evolution.

Using capture probes may be advantageous over polymerase chain reaction (PCR)-based assays to enrich and target sequences of interest due to the difficulty of PCR to target multiple genes simultaneously. To target multiple genes, PCR may require a large number of primers, for example, up to potentially 100,000 primers to amplify and target 50,000 sequences, and require enzymatic operations in order to generate nucleic acid molecules for identification. Optimizing the ratio of the PCR primers of multiple genes may also be difficult and may result in biased amplification and results that may not represent the relative amounts of target nucleic acids in a nucleic acid sample.

As used in the specification and claims, the singular forms "a," "an," and "the" include plural references unless the context clearly dictates otherwise. For example, the term "a chimeric transmembrane receptor polypeptide" includes a plurality of chimeric transmembrane receptor polypeptides.

The term "about" or "approximately" means within an acceptable error range for the particular value as determined by one of ordinary skill in the art, which will depend in part on how the value is measured or determined, i.e., the limitations of the measurement system. For example, "about" can mean within 1 or more than 1 standard deviation, per the practice in the art. Alternatively, "about" can mean a range of up to 20%, up to 10%, up to 5%, or up to 1% of a given value. Alternatively, such as with respect to biological systems or processes, the term can mean within an order of magnitude, or within 5-fold, or within 2-fold, of a value. Where particular values are described in the application and claims, unless otherwise stated, the term "about" meaning within an acceptable error range for the particular value should be assumed.

As used herein, a "cell" generally refers to a biological cell. A cell can be the basic structural, functional and/or biological unit of a living organism. A cell can originate from any organism having one or more cells. Some non-limiting examples include: a prokaryotic cell, eukaryotic cell, a bacterial cell, an archaeal cell, a cell of a single-cell eukaryotic organism, a protozoa cell, a cell from a plant (e.g. cells from plant crops, fruits, vegetables, grains, soy bean, corn, maize, wheat, seeds, tomatoes, rice, cassava, sugarcane, pumpkin, hay, potatoes, cotton, *cannabis*, tobacco, flowering plants, conifers, gymnosperms, ferns, clubmosses, hornworts, liverworts, mosses), an algal cell, (e.g., *Botryococcus braunii, Chlamydomonas reinhardtii, Nannochloropsis gaditana, Chlorella pyrenoidosa, Sargassum patens* C. Agardh, and the like), seaweeds (e.g. kelp), a fungal cell (e.g., a yeast cell, a cell from a mushroom), an animal cell, a cell from an invertebrate animal (e.g. fruit fly, cnidarian, echinoderm, nematode, etc.), a cell from a vertebrate animal (e.g., fish, amphibian, reptile, bird, mammal), a cell from a mammal (e.g., a pig, a cow, a goat, a sheep, a rodent, a rat, a mouse, a non-human primate, a human, etc.), and etcetera. Sometimes a cell is not orginating from a natural organism (e.g. a cell can be a synthetically made, sometimes termed an artificial cell).

The term "nucleotide," as used herein, generally refers to a base-sugar-phosphate combination. A nucleotide can comprise a synthetic nucleotide. A nucleotide can comprise a synthetic nucleotide analog. Nucleotides can be monomeric units of a nucleic acid sequence (e.g. deoxyribonucleic acid (DNA) and ribonucleic acid (RNA)). The term nucleotide can include ribonucleoside triphosphates adenosine triphosphate (ATP), uridine triphosphate (UTP), cytosine triphosphate (CTP), guanosine triphosphate (GTP) and deoxyribonucleoside triphosphates such as dATP, dCTP, dITP, dUTP, dGTP, dTTP, or derivatives thereof. Such derivatives can include, for example, [αS]dATP, 7-deaza-dGTP and 7-deaza-dATP, and nucleotide derivatives that confer nuclease resistance on the nucleic acid molecule containing them. The term nucleotide as used herein can refer to dideoxyribonucleoside triphosphates (ddNTPs) and their derivatives. Illustrative examples of dideoxyribonucleoside triphosphates can include, but are not limited to, ddATP, ddCTP, ddGTP, ddITP, and ddTTP. A nucleotide can be unlabeled or detectably labeled. Labeling can also be carried out with quantum dots. Detectable labels can include, for example, radioactive isotopes, fluorescent labels, chemiluminescent labels, bioluminescent labels and enzyme labels. Fluorescent labels of nucleotides can include but are not limited fluorescein, 5-carboxyfluorescein (FAM), 2'7'-dimethoxy-4'5-dichloro-6-carboxyfluorescein (JOE), rhodamine, 6-carboxyrhodamine (R6G), N,N,N',N'-tetramethyl-6-carboxyrhodamine (TAMRA), 6-carboxy-X-rhodamine (ROX), 4-(4'dimethylaminophenylazo) benzoic acid (DABCYL), Cascade Blue, Oregon Green, Texas Red, Cyanine and 5-(2'-aminoethyl)aminonaphthalene-1-sulfonic acid (EDANS). Specific examples of fluorescently labeled nucleotides can include [R6G]dUTP, [TAMRA]dUTP, [R110]dCTP, [R6G]dCTP, [TAMRA]dCTP, [JOE]ddATP, [R6G]ddATP, [FAM]ddCTP, [R110]ddCTP, [TAMRA]ddGTP, [ROX]ddTTP, [dR6G]ddATP, [dR110]ddCTP, [dTAMRA]ddGTP, and [dROX]ddTTP available from Perkin Elmer, Foster City, Calif.; FluoroLink DeoxyNucleotides, FluoroLink Cy3-dCTP, FluoroLink Cy5-dCTP, FluoroLink Fluor X-dCTP, FluoroLink Cy3-dUTP, and FluoroLink Cy5-dUTP available from Amersham, Arlington Heights, Ill.; Fluorescein-15-dATP, Fluorescein-12-dUTP, Tetramethyl-rodamine-6-dUTP, IR770-9-dATP, Fluorescein-12-ddUTP, Fluorescein-12-UTP, and Fluorescein-15-2'-dATP available from Boehringer Mannheim, Indianapolis, Ind.; and Chromosome Labeled Nucleotides, BODIPY-FL-14-UTP, BODIPY-FL-4-UTP, BODIPY-TMR-14-UTP, BODIPY-TMR-14-dUTP, BODIPY-TR-14-UTP, BODIPY-TR-14-dUTP, Cascade Blue-7-UTP, Cascade Blue-7-dUTP, fluorescein-12-UTP, fluorescein-12-dUTP, Oregon Green 488-5-dUTP, Rhodamine Green-5-UTP, Rhodamine Green-5-dUTP, tetramethylrhodamine-6-UTP, tetramethylrhodamine-6-dUTP, Texas Red-5-UTP, Texas Red-5-dUTP, and Texas Red-12-dUTP available from Molecular Probes, Eugene, Oreg. Nucleotides can also be labeled or marked by chemical modification. A chemically-modified single nucleotide can be biotin-dNTP. Some non-limiting examples of biotinylated dNTPs can include, biotin-dATP (e.g., bio-N6-ddATP, biotin-14-dATP), biotin-dCTP (e.g., biotin-11-dCTP, biotin-14-dCTP), and biotin-dUTP (e.g. biotin-11-dUTP, biotin-16-dUTP, biotin-20-dUTP).

The terms "genome" and "genomes," as used herein, are used to generally refer to a portion of a genome of a subject or the entirety of a genome of a subject. For instance, a genome may refer to a gene sequence of a subject. A genome may refer to a whole genome sequence of a subject.

The terms "polynucleotide," "oligonucleotide," and "nucleic acid" are used interchangeably to refer to a polymeric form of nucleotides of any length, either deoxyribonucleotides or ribonucleotides, or analogs thereof, either in single-, double-, or multi-stranded form. A polynucleotide can be exogenous or endogenous to a cell. A polynucleotide can exist in a cell-free environment. A polynucleotide can be a gene or fragment thereof. A polynucleotide can be DNA. A polynucleotide can be RNA. A polynucleotide can have any three dimensional structure, and can perform any function. A polynucleotide can comprise one or more analogs (e.g. altered backbone, sugar, or nucleobase). If present, modifications to the nucleotide structure can be imparted before or after assembly of the polymer. Some non-limiting examples of analogs include: 5-bromouracil, peptide nucleic acid, xeno nucleic acid, morpholinos, locked nucleic acids, glycol nucleic acids, threose nucleic acids, dideoxynucleotides, cordycepin, 7-deaza-GTP, fluorophores (e.g. rhodamine or fluorescein linked to the sugar), thiol containing nucleotides, biotin linked nucleotides, fluorescent base analogs, CpG islands, methyl-7-guanosine, methylated nucleotides, inosine, thiouridine, pseudourdine, dihydrouridine, queuosine, and wyosine. Non-limiting examples of polynucleotides include coding or non-coding regions of a gene or gene fragment, loci (locus) defined from linkage analysis, exons, introns, messenger RNA (mRNA), transfer RNA (tRNA), ribosomal RNA (rRNA), short interfering RNA (siRNA), short-hairpin RNA (shRNA), micro-RNA (miRNA), ribozymes, cDNA, recombinant polynucleotides, branched polynucleotides, plasmids, vectors, isolated DNA of any sequence, isolated RNA of any sequence, cell-free polynucleotides including cell-free DNA (cfDNA) and cell-free RNA (cfRNA), nucleic acid probes, and primers. The sequence of nucleotides can be interrupted by non-nucleotide components. Any of the foregoing nucleic acid molecules may be engineered or synthesized.

The term "gene," as used herein, refers to a nucleic acid (e.g., DNA such as genomic DNA and cDNA) and its corresponding nucleotide sequence that is involved in encoding an RNA transcript. The term as used herein with reference to genomic DNA includes intervening, non-coding regions as well as regulatory regions and can include 5' and 3' ends. In some uses, the term encompasses the transcribed sequences, including 5' and 3' untranslated regions (5'-UTR and 3'-UTR), exons and introns. In some genes, the transcribed region will contain "open reading frames" that encode polypeptides. In some uses of the term, a "gene" comprises only the coding sequences (e.g., an "open reading frame" or "coding region") necessary for encoding a polypeptide. In some cases, genes do not encode a polypeptide, for example, ribosomal RNA genes (rRNA) and transfer RNA (tRNA) genes. In some cases, the term "gene" includes not only the transcribed sequences, but in addition, also includes non-transcribed regions including upstream and downstream regulatory regions, enhancers and promoters. A gene can refer to an "endogenous gene" or a native gene in its natural location in the genome of an organism. A gene can refer to an "exogenous gene" or a non-native gene. A non-native gene can refer to a gene not normally found in the host organism but which is introduced into the host organism by gene transfer. A non-native gene can also refer to a gene not in its natural location in the genome of an organism such as a genetically modified organism. A non-native gene can also refer to a naturally occurring nucleic acid or polypeptide sequence that comprises mutations, insertions and/or deletions (e.g., non-native sequence).

The term "percent (%) identity," as used herein, refers to the percentage of amino acid or nucleic acid residues of a candidate sequence that are identical to the amino acid or nucleic acid residues of a reference sequence after aligning the sequences and introducing gaps, if necessary, to achieve the maximum percent identity (i.e., gaps can be introduced in one or both of the candidate and reference sequences for optimal alignment and non-homologous sequences can be disregarded for comparison purposes). Alignment, for purposes of determining percent identity, can be achieved in various ways, such as, for example, using computer software such as BLAST, ALIGN, or Megalign (DNASTAR) software. Percent identity of two sequences can be calculated by aligning a test sequence with a comparison sequence using BLAST, determining the number of amino acids or nucleotides in the aligned test sequence that are identical to amino acids or nucleotides in the same position of the comparison sequence, and dividing the number of identical amino acids or nucleotides by the number of amino acids or nucleotides in the comparison sequence.

The term "subject," as used herein, generally refers to any animal, e.g., a mammal or marsupial. A subject may be a patient. A subject may be symptomatic or asymptomatic with respect to a disease or ailment. A subject may be primate (e.g., a human), non-human primate (e.g., rhesus or other types of macaques), dog, cat, mouse, pig, horse, donkey, cow, sheep, rat, and fowl. Mammals include, but are not limited to, murines, simians, humans, farm animals, sport animals, and pets. Tissues, cells and their progeny of a biological entity obtained in vivo or cultured in vitro are also encompassed. A host is an organism that can harbor a non-host. The subject may be asymptomatic with respect to a disease. As an alternative, the subject is not asymptomatic with respect to the disease.

The terms "treatment" and "treating," as used herein, refer to an approach for obtaining beneficial or desired results including but not limited to a therapeutic benefit and/or a prophylactic benefit. For example, a treatment can comprise administering a system or cell population disclosed herein. By therapeutic benefit is meant any therapeutically relevant improvement in or effect on one or more diseases, conditions, or symptoms under treatment. For prophylactic benefit, a composition can be administered to a subject at risk of developing a particular disease, condition, or symptom, or to a subject reporting one or more of the physiological symptoms of a disease, even though the disease, condition, or symptom may not have yet been manifested.

In some cases, the present disclosure also provides compositions and methods for processing and analyzing biological samples. In some cases, a biological sample from a subject can comprise nucleic acids from the subject and nucleic acid molecules that are not from the subject. In some cases, a biological sample can comprise nucleic acids from a human and non-human genome. In some cases, a non-human genome can be from viruses, bacteria, bacterial phage, fungi, protists, archaea, amoeba, helminths, algae, or a combination thereof. In some cases, a source of a non-human genome can be beneficial to a human host. In some cases, a source of a non-human genome can be involved in modulating a disease, such as cancer. In some cases, a source of a non-human organism comprising non-human genome can behave directly by causing mutations in human cells thereby causing cancer in a subject. In some cases, a source of a non-human genome can behave indirectly for instance by stimulating the immune system of a human host which influences its ability to fight disease. In some cases, the present disclosure also provides a method comprising identifying the presence of non-human genomes and human genomes in a sample.

A sample can be from skin, saliva, nasal passages, gut, intestine, genitals, or a combination thereof. In some cases, a sample can be acquired by swabbing, biopsy, collecting stool, collecting urine, collecting saliva, and the like.

The human genome (about 3 billion bases) is about 1,000 times larger than a non-human genome, for example a bacterial genome, and many thousands of times the size of most viral genomes. In some cases, a method can comprise a sampling method to enrich a non-human genome in a mixed sample.

The present disclosure also provides a method comprising sequence (or sequencing) analysis of microbial nucleic acids from a sample. Sequencing analysis can comprise PCR amplification, for instance subsections of the 16S ribosomal RNA gene, and untargeted, metagenomics methods that use deep sequencing. The method can involve selection of sample types and/or enrichment methods which may seek to minimize the amount a human genome, so as to optimize sensitivity to a non-human genome.

In one aspect, a first plurality of nucleic acid molecules can be from a subject. A subject can be human and hence the present disclosure also provides human nucleic acid molecules. The present disclosure also provides a first subset or product using a plurality of nucleic acid probes that can be from a human genome. The present disclosure also provides a human genome. In some cases, a human genome may include, for example, inherited genetic variants, somatic variants, VDJ recombination in immune cells, differential gene expression in different cell types, and other properties. At least some of the foregoing may contribute to, or be associated with disease in a subject (e.g., somatic variants in cancer). A genome may comprise genes, exons, UTRs, regulatory regions, splice sites, reassembly genes, alternate sequence, reassembly genes, gene phasing, exogenous sequences, and the like.

In some cases, a nucleic acid in a biological sample can be analyzed by sequencing. In some cases, sequencing of nucleic acids, typically from a blood or diseased tissue can be performed. In some cases, a blood sample can comprise peripheral blood mononuclear cells, cell free DNA, or a combination thereof. In some cases, a diseased tissue can comprise cancer. In some cases, sequence analysis of nucleic acids from a blood sample or a diseased tissue sample can comprise generation of amplicon panels, hybrid capture, and untargeted methods such as whole genome sequencing. In some cases, a method can involve selecting of a sample types, human-genome enrichment methods, and a combination thereof.

In some cases, a biological sample can comprise subject nucleic acids, non-subject nucleic acids, and combinations thereof. In some cases, a biological sample can comprise host nucleic acids, non-host nucleic acids, and combinations thereof. In some cases, a biological sample can comprise a genome that encodes a receptor. In some cases, a receptor can be from an immune cell. In some cases, a receptor from an immune cell can be a T cell receptor (TCR), B cell receptor (BCR), chimeric antigen receptor (CAR), and the like.

In some cases, a method provided herein comprises subjecting nucleic acid molecules to an assay to yield sequence information. The assay can comprise sequencing nucleic acid comprising a VDJ rearrangement or VDJ recombination. In some cases, a VDJ rearrangement or recombination can refer to a cellular receptor. For example, a somatic hypermutation can produce antibody-coding B cell receptor (BCR) sequences for a remarkable diversity of antigens. In some cases, a BCR can be sequenced. A method provided herein can comprise sequencing a BCR to elucidate how antibodies develop. For example, a method can comprise a sequence analysis to annotate each base as coming from a specific one of the V, D, or J genes, or from an N-addition (a.k.a. non-templated insertion). In some cases, a VDJ recombination may generate CDR3 sequence. In some cases, a CDR3 sequence may generate a polypeptide that binds an antigen, for instance a tumor antigen. In some cases, a CDR3 sequence may generate a polypeptide that binds an antigen, for instance a neoantigen.

In some cases, a method provided herein can comprise sequencing nucleic acids encoding or associated with candidate tumor neoantigens. In some cases, a method provided herein can comprise sequencing detected CDR3 sequences. In some aspects, a subject TCR can be identified using a variety of methods. In some cases a TCR can be identified using whole-exomic sequencing. For example, a TCR can target a neoantigen or neoepitope that is identified by whole-exomic sequencing of a target cell. Alternatively, a TCR can be identified from autologous, allogenic, or xenogeneic repertoires. In some cases, a gene that can comprise a mutation that gives rise to a neoantigen or neoepitope can be ABL1, ACOl 1997, ACVR2A, AFP, AKT1, ALK, ALPPL2, ANAPC1, APC, ARID1A, AR, AR-v7, ASCL2, β2M, BRAF, BTK, C15ORF40, CDH1, CLDN6, CNOT1, CT45A5, CTAG1B, DCT, DKK4, EEF1B2, EEF1DP3, EGFR, EIF2B3, env, EPHB2, ERBB3, ESR1, ESRP1, FAM11 IB, FGFR3, FRG1B, GAGE1, GAGE 10, GATA3, GBP3, HER2, IDH1, JAK1, KIT, KRAS, LMAN1, MABEB 16, MAGEA1, MAGEA10, MAGEA4, MAGEA8, MAGEB 17, MAGEB4, MAGEC1, MEK, MLANA, MLL2, MMP13, MSH3, MSH6, MYC, NDUFC2, NRAS, NY-ESO, PAGE2, PAGE5, PDGFRa, PIK3CA, PMEL, pol protein, POLE, PTEN, RAC1, RBM27, RNF43, RPL22, RUNX1, SEC31A, SEC63, SF3B 1, SLC35F5, SLC45A2, SMAP1, SMAP1, SPOP, TFAM, TGFBR2, THAP5, TP53, TTK, TYR, UBR5, VHL, XPOT.

The present disclosure also provides methods comprising obtaining or providing nucleic acid samples or subsets of nucleic acid molecules comprising one or more genomes. The methods disclosed herein may analyze nucleic subsets of nucleic acid molecules generated from a biological sample. A subset may comprise nucleic acid molecules from a subject and nucleic acid molecules that are not from the subject. For instance, human and microbial sequences may be enriched using target capture and sequence. The one or more genomes may comprise one or more genome features.

Genome features may comprise an entire genome or a portion thereof. Genome features may comprise an entire exome or a portion thereof. Genome features may comprise one or more sets of genes. Genome features may comprise one or more genes. Genome features may comprise one or more sets of regulatory elements. Genome features may comprise one or more regulatory elements. Genome features may comprise a set of polymorphisms. Genome features may comprise one or more polymorphisms. In some cases, a polymorphism refers to a mutation in a genotype. A polymorphism may comprise one or more base changes, an insertion, a repeat, or a deletion of one or more bases. Genome features can comprise copy number variants (CNVs), transversions, other rearrangements, and other forms of genetic variation. In some cases, one or more features of a subset of a nucleic acid sample can be polymorphic markers including restriction fragment length polymorphisms, variable number of tandem repeats (VNTR's), hypervariable regions, mini satellites, dinucleotide repeats, trinucleotide repeats, tetranucleotide repeats, simple sequence repeats, and insertion elements such as Alu. In some cases, a difference between a first subset of nucleic acid molecules and a second subset of nucleic acid molecules can be polymorphic markers including restriction fragment length polymorphisms, variable number of tandem repeats (VNTR's), hypervariable regions, minisatellites, dinucleotide repeats, trinucleotide repeats, tetranucleotide repeats, simple sequence repeats, and insertion elements such as Alu. The allelic form occurring most frequently in a selected population is sometimes referred to as the wildtype form. Diploid organisms may be homozygous or heterozygous for allelic forms. A diallelic polymorphism has two forms. A triallelic polymorphism has three forms. Polymorphisms can include Single nucleotide polymorphisms (SNPs). In some aspects of the disclosure, one or more polymorphisms comprise one or more single nucleotide variations, inDels, small insertions, small deletions, structural variant junctions, variable length tandem repeats, flanking sequences, or a combination thereof. One or more polymorphisms may be located within a coding and/or non-coding region. One or more polymorphisms may be located within, around, or near a gene, exon, intron, splice site, untranslated region, or a combination thereof. One or more polymorphisms may be may span at least a portion of a gene, exon, intron, untranslated region. In some cases, a genome feature may relate to the GC content, complexity, and/or mappablity of one or more nucleic acid molecules. Genome features may comprise one or more simple tandem repeats (STRs), unstable expanding repeats, segmental duplications, single and paired read degenerative mapping scores, GRCh38 or GRCh37 patches, or a combination thereof. Genome features may comprise one or more low mean coverage regions from whole genome sequencing (WGS), zero mean coverage regions from WGS, validated compressions, or a combination thereof. Genome features may comprise one or more alternate or non-reference sequences.

Genome features may comprise one or more gene phasing and reassembly genes. Examples of phasing and reassembly genes include, but are not limited to, one or more major histocompatibility complexes, blood typing, and amaylase gene family. In some cases, gene phasing and/or reassembly genes may comprise a gene associated with blood typing. The blood typing genes may comprise ABO, RHD, RHCE, or a combination thereof.

In some cases, a genome feature may comprise a reassembly gene. A reassembly gene can comprise a gene involved in an immune response. Genes involved in immune responses can comprise a gene involved in a major histocompatibility complex, immune receptors, and cellular functions. The one or more major histocompatibility complexes may comprise one or more HLA Class I, HLA Class II, or a combination thereof. HLA class I can be any one of HLA-A, HLA-B, HLA-C, or a combination thereof. HLA class II can be anyone of HLA-DP, HLA-DM, HLA-DOA, HLA-DOB, HLA-DQ, HLA-DR, or a combination thereof. A gene involved in an immune response can be RAG1, RAG2, and combinations thereof. In some cases, a reassembly gene may comprise a gene involved in VDJ recombination. For example, to establish diversity in B cell and T cell receptors (BCR and TCRs), genes can be created by recombining preexisting gene segments. In some cases, different combinations of a finite set of gene segments can give rise to receptors that can recognize unlimited numbers of foreign genomes or non-human genomes. VDJ recombination can comprise cleaving DNA comprising recombination signal sequences (RSSs). In some cases, fragmented sequences can be reassembled using cellular repair mechanisms. The present disclosure also provides methods comprising sequencing fragmented sections of genomes from a VDJ recombination. For example, the present disclosure provides methods that comprise sequencing at a site of VDJ recombination.

In some aspects of the disclosure, the one or more genome features may not be mutually exclusive. For example, a genome feature comprising an entire genome or a portion thereof can overlap with an additional genome feature such as an entire exome or a portion thereof, one or more genes, one or more regulatory elements, and the like. Alternatively, the one or more genome features may be mutually exclusive. For example, a genome comprising the noncoding portion of an entire genome may not overlap with a genome feature such as an exome or portion thereof or the coding portion of a gene. Alternatively, or additionally, the one or more genome features are partially exclusive or partially inclusive. For example, a genome comprising an entire exome or a portion thereof can partially overlap with a genome comprising an exon portion of a gene. However, the genome comprising the entire exome or portion thereof may not overlap with the genome comprising the intron portion of the gene. Thus, a genome feature comprising a gene or portion thereof may partially exclude and/or partially include a genome feature comprising an entire exome or portion thereof. In some cases, a gene feature can be species related such that more than one species can be distinguished. In some cases, a gene feature can be species related such that a human gene feature and a bacterial gene feature can be distinguished. In some cases, a first subset of nucleic acid molecules are specific to one species and a second subset of nucleic acid molecules are specific to a second species.

A biological sample can comprise a human genome, a non-human genome, or a combination thereof. In some cases, a biological sample can be processed. In some cases, a biological sample can under enrichment for nucleic acid sequences of a subject, e.g. a human, or for a nucleic acid sequences not from a subject (e.g. non-human) concurrent detection of a human genome and a non-human genome from the sample can be performed. The biological sample may comprise a cell-free nucleic acid molecule, such as cell-free DNA (cfDNA) or cell-free RNA. The cell-free nucleic acid molecule may be a circulating tumor nucleic acid molecule (e.g., circulating tumor DNA). The cell-free DNA may comprise mutations that may be indicative of, related to, or associated with a disease, such as cancer.

A biological sample may have nucleic acid molecules comprising engineered sequences. For example, nucleic acids in a biological sample may comprise exogenous or alternate sequences such as tags, exogenous receptors such as chimeric antigen receptor (CAR) receptors, plasmid sequences, and neo-antigen specific sequences to name a few. In some cases, engineered sequence may be utilized as diagnostic markers. In some cases, an engineered sequence may be utilized to determine if a therapeutic trafficked to a target, such as a tumor target. An alternate sequence may be exogenous or endogenous. In some cases, an alternate sequence may include be from a plasmid sequence. A plasmid sequence can be DNA or RNA. In some cases, a plasmid sequence can also be a DNA minicircle sequence or a doggy bone sequence.

The present disclosure also provides methods comprising obtaining or providing nucleic acid samples or subsets of nucleic acid molecules comprising one or more transcriptomes. Nucleic acid samples may comprise mRNA. The mRNA may be from different tissues in the subject. Amounts of mRNA in the sample may be used to analyze the expression levels of mRNA or proteins in tissue and subject specific manners. For example, an amount of mRNA in a sample may be related to a specific feature or disease (e.g., cancer) in a subject. Additionally, an amount of mRNA in a sample may indicate a change or relative difference in expression in a specific tissue type in a subject. In some cases the mRNA may be processed to form cDNA. For example, the mRNA may be subjected to reverse transcription using a reverse transcriptase to synthesize a cDNA molecule. The cDNA molecule may be subjected to capture, isolation, enrichment, amplification, sequencing, or other reactions that may be performed on nucleic acids as described elsewhere herein.

Nucleic acids from a biologic sample containing subject and non-subject sequences may be enriched and sequenced in a single pool and separated in silico. For example, a mixed human genome and non-human genome can be separated out by alignment with the human and non-human-species reference sequences. A separation of sequences by alignment can be possible because the human genome has diverged from the microbial genomes over the course of evolution. A genome, for instance DNA from a non-human genome such as a microbial species generally does not align to the human genome and vice versa. A non-human genome, such as a microbial genome, may have segments in common with, or similar to other non-human genomes. More than one non-human genome in a mixture of human genome and non-human genome may need additional alignment to identify a non-human species.

In some cases, a method can comprise generating a subset of nucleic acid molecules from a biological sample. In some cases, a method can comprise generating a subset of nucleic acid molecules from a biological sample by conducting one or more hybridization reactions. A hybridization reaction can comprise an enrichment. In some cases, enrichment can be performed. Enrichment can be performed by various methods. In some cases, enrichment can be performed by hybrid capture, array capture, bead capture, and the like. In some cases, hybrid capture can be in-solution or on a solid support, such as on an array. In some cases, enrichment can be performed by molecular inversion probes (MIP). Enrichment can be performed by amplification, for example using PCR. In some cases, a method can comprise generating a subset of nucleic acids by amplification of a human genome or a non-human genome for the purposes of an enrichment. In some cases, amplification can include one of: polymerase chain reaction (PCR)-based techniques (e.g., solid-phase PCR, RT-PCR, qPCR, multiplex PCR, touchdown PCR, nanoPCR, nested PCR, hot start PCR, etc.), helicase-dependent amplification (HDA), loop mediated isothermal amplification (LAMP), self-sustained sequence replication (3SR), nucleic acid sequence based amplification (NASBA), strand displacement amplification (SDA), rolling circle amplification (RCA), ligase chain reaction (LCR), and any other suitable amplification technique.

Figure 3:
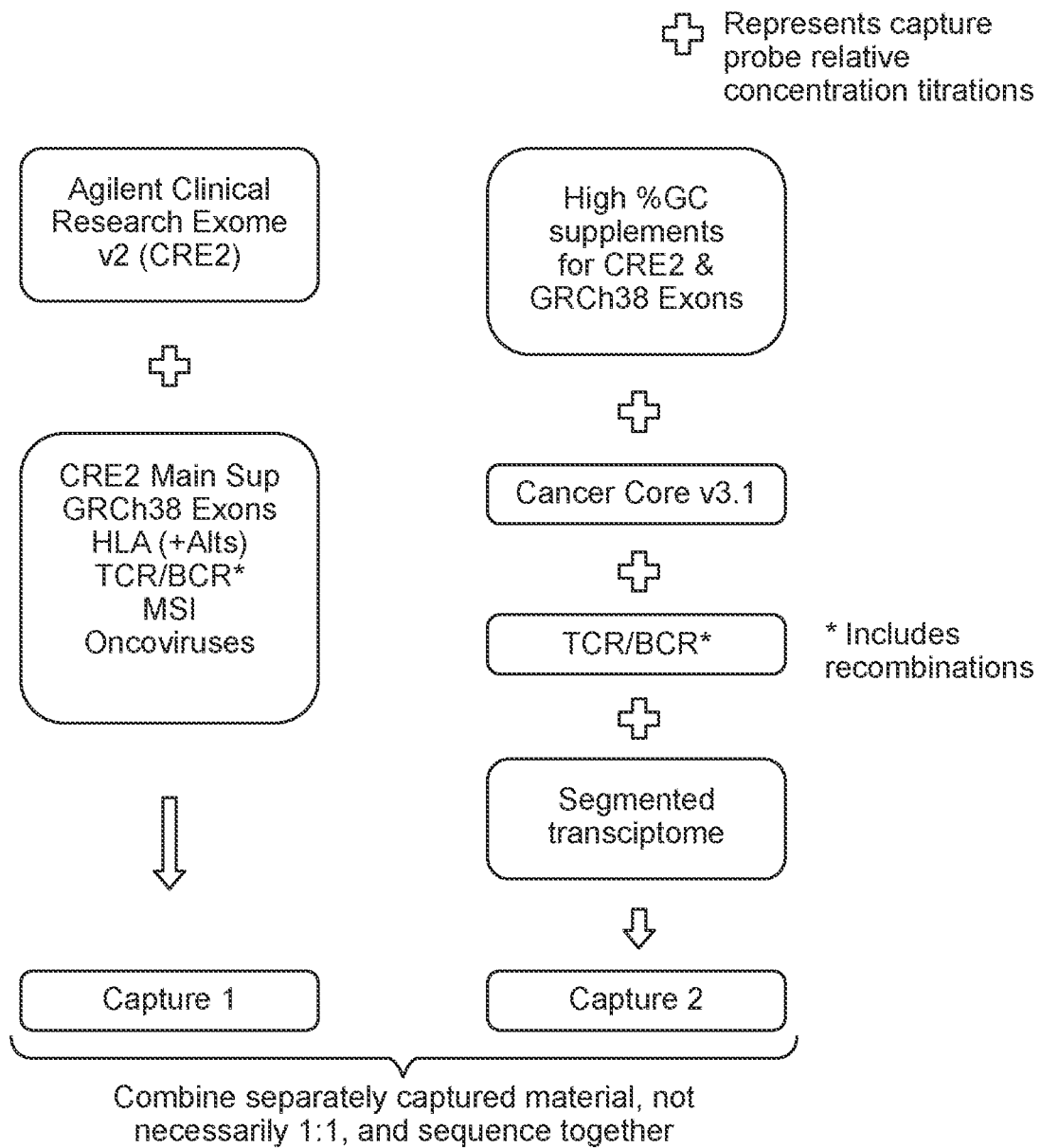
FIG. 3 schematically illustrates a method for generating a subset of nucleic acid molecules using a first plurality of nucleic acid probes and a second plurality of nucleic acid probes. The first plurality of nucleic acid probes may bind a segmented transcriptome.
Figure 4:
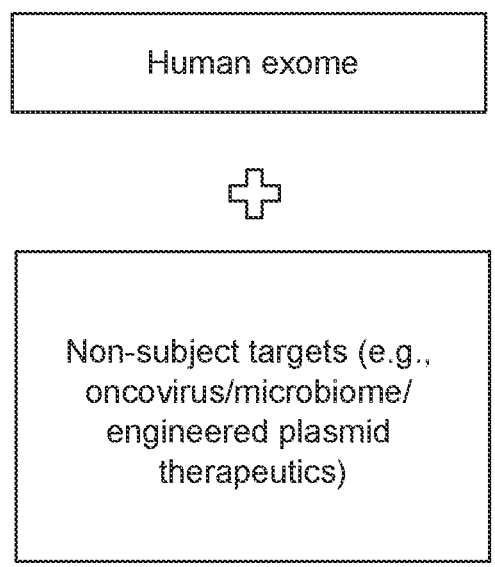
FIG. 4 schematically illustrates a method for generating a subset of nucleic acid molecules using a plurality of nucleic acid probes. The plurality of nucleic acid probes may comprise a probe set targeting an exome of a subject and a probe set targeting non-subject nucleic acid sequences.

A pool of nucleic acid probes can comprise a human exome capture kit, for instance Agilent Clinical Research Exome v2 (FIG. 1). A pool of nucleic acid probes can comprise hybridization probes which are complementary to the human sequences it targets. A pool of nucleic acid probes can comprise from about 50,000 capture probes, so as to target the genome of a majority of predetermined human genes and the like. A capture probe can be designed to target genes, exons, UTRs, regulatory regions, splice sites, reassembly genes, alternate sequence, and additional genome content. In some cases, a method can comprise a pool of nucleic acid probes that are designed to target non-human sequences. In some cases, a pool of nucleic acid probes can be specific to non-human genomes such from viral, bacterial, fungal or archaeal genomes, i.e. from the human microbiome. In some cases, a pool of nucleic acid probes can be combined with a second pool of nucleic acid probes which may be specific to a second species as compared to the first pool of nucleic acid probes (FIG. 2). A pool of nucleic acid probes can be configured to bind human sequences and non-human sequences, and a pool of nucleic acid probes can bind sequences from a segmented transcriptome (FIG. 3). In some cases, a pool of nucleic acid probes can bind human sequences and a pool of nucleic acid probes can bind non-human sequences (FIG. 4). In some cases a pool of nucleic acid probes can be used for a single hybridization-based capture reaction with nucleic acids extracted from a patient sample. In some cases, a method can comprise sequencing a pool of nucleic acids which have been captured. Captured or enriched nucleic acids can be human, non-human, or human and non-human sequences, sequencing can comprise Illumina NovaSeq-6000 DNA sequencing instruments. In some cases, capture probes targeting microbial species, may be designed to target regions of a microbial species sequence where one or more species differ, or immediately adjacent to regions where one or more species differ, for example non-human or human. In some cases, a method comprises targeting regions of dissimilarity between non-human sequences, such as microbial sequences, thereby allowing for the capture of nucleic acids from a large number of potential non-human, microbiome species with a small number of capture probes. By using capture probes which may comprise shared sequence regions, but are adjacent to variable regions, many of the non-human sequences that can be captured can span both.

In some cases, sequences from non-human genomes can then be assigned to their source species by one or more species-unique regions. For example, a 16S ribosomal RNA gene, present in almost all bacteria has about nine regions where the sequence varies from species to species, interleaved with regions of shared sequence. In some cases, captured molecules whose sequences extend from these shared regions into the variable regions, can then be assigned to their source species based on the sequence from the variable region part. Fungal nucleic acid sequences can similarly be assessed by using the partially conserved D2 region of large-subunit ribosomal RNA gene of fungal genomes. A exome of a genome can be analyzed. An intronic region of a genome can be analyzed. An exome primarily targets the coding regions of the human genome and may represent less than 2% of the full human genome. By excluding most of the intronic and intergenic portion of the human genome, the amount of human sequence can be reduced by about 98%. An exomes may be augmented to include non-coding content. Sequencing of an exome, such as in cancer, can allow for deep sequencing and thereby improving the detection of somatic variants with low allele frequencies, and also improving the detection of non-human sequences co-captured from a sample.

The present disclosure also provides compositions and methods for processing a biological sample. A biological sample can be obtained from a subject, such as an adult or child. In some cases a method for processing a biological sample can comprise (a) generating a subset of nucleic acid molecules from the biological sample using a pool of nucleic acid probes wherein the probes comprise (i) a first plurality of nucleic acid probes configured to target elements of a human genome and (ii) a second plurality of nucleic acid probes configured to target elements of one or more non-human genome(s); and (b) subjecting the subset of nucleic acid molecules to an assay to yield sequence information comprising sequences of (i) human nucleic acids from the biological sample from the subject and (ii) non-human nucleic acids from the biological sample of the subject.

The methods disclosed may comprise detecting, monitoring, quantitating, or evaluating one or more non-human nucleic acid molecules or one or more diseases or conditions caused by one or more non-human genomes or non-host genomes. In some cases, a capture probe can target between different genuses. In some cases, a capture probe can target between different species. In some aspects, a capture probe can target between different orders of more than one organism. In some cases, a capture probe can target a plantae, Animalia, fungi, protest, eubacteria, and/or archaebacterial. In some cases, a capture probe can target viruses, bacteria, bacterial phages, fungi, protists, archea, amoeba, helminths, algae, genetically modified cells, genetically modified vectors, and combinations thereof. In some cases, a non-human sequence can be bacterial. For example, a bacterial sequence can be from acidiobacteria, actiniobacteria, Aquificae, armatimonadetes, Bacteroidetes, caldiserica, chlamydiae, Chlorobi, chloroflexi, chrysiogenetes, cyanobacteria, deferribacteres, deinococcus-thermus, dictyoglomi, elusimicrobia, fibrobacteres, firmicutes, fusobacteria, gemmatimonadetes, lentisphaerae, Nitrospirae, planctomycetes, Proteobacteria, spirochaetes, synergistetes, tenericutes, thermodesulfobacteria, thermomicrobia, thermotogae, and/or verrucomicrobia. In some cases, a non-human sequence can be from, but are not limited to, *Bordetella, Borrelia, Brucella, Campylobacter, Chlamydia, Chlamydophila, Clostridium, Corynebacterium, Enterococcus, Escherichia, Francisella, Haemophilus, Helicobacter, Legionella, Leptospira, Listeria, Mycobacterium, Mycoplasma, Neisseria, Pseudomonas, Rickettsia, Salmonella, Shigella, Staphylococcus, Streptococcus, Treponema, Vibrio,* or *Yersinia*. Additional pathogens include, but are not limited to, *Mycobacterium tuberculosis, Streptococcus, Pseudomonas, Shigella, Campylobacter,* and *Salmonella*. In some cases, a capture probe can target a Fungi such as blastocladiomycota, chytridiomycota, Glomeromycota, Microsporidia, Neocallimastigomycota, Deuteromycota, Ascomycota, Pezizomycotina, Saccharomycotina, Taphrinomycotina, Basidiomycota, Agaricomycotina, Pucciniomycotina, Ustilaginomycotina, Entomophthoromycotina, Kickxellomycotina, Mucoromycotina, Zoopagomycotina, and the like. In some cases, a non-human or non-host can be from a cow, horse, fish, donkey, rabbit, rat, mouse, hamster, dog, cat, pig, snake, sheep, goat, and the like.

Disease or conditions caused by or associated with one or more non-human genomes may comprise tuberculosis, pneumonia, foodborne illnesses, tetanus, typhoid fever, diphtheria, syphilis, leprosy, bacterial vaginosis, bacterial meningitis, bacterial pneumonia, a urinary tract infection, bacterial gastroenteritis, bacterial skin infections, or any combination thereof. Examples of bacterial skin infections include, but are not limited to, impetigo which may be caused by *Staphylococcus aureus* or *Streptococcus pyogenes*; erysipelas which may be caused by a *streptococcus* bacterial infection of the deep epidermis with lymphatic spread; and cellulitis which may be caused by normal skin flora or by exogenous bacteria.

Non-subject nucleic acid sequence may be derived from a fungus, such as, *Candida, Aspergillus, Cryptococcus, Histoplasma, Pneumocystis*, and Stachybotrys. Examples of diseases or conditions caused by a fungus include, but are not limited to, jock itch, yeast infection, ringworm, and athlete's foot.

In some cases, a non-subject or non-host, nucleic acid sequence can be from a protist. A protist can comprise protozoa, protophyta, molds, and combinations thereof. A protist can be an archaeplastida. An archaeplastida can be Rhodophyta or Glaucophyta. A protist can be a Sar or a Harosa. A SAR can be a clade that includes stramenopiles, alveolates, and Rhizaria (SAR). Additionally, the clade SAR can include Stramenopiles, Alveolata, Apicomplexa, Ciliophora, Dinoflagellata, Rhizaria, Cercozoa, Foraminifera, Radiolaria, and combinations thereof. In some cases, a protist can be an Excavata. An Excavata can be Euglenozoa, Percolozoa, Metamonada, and combinations thereof. In some cases, a non-host can be an Amoebozoa, Hacrobia, Apusozoa, Opisthokonta, and/or Choanozoa.

The non-subject nucleic acid sequence may be derived from a virus. Examples of viruses include, but are not limited to, adenovirus, coxsackievirus, Epstein-Barr virus, Hepatitis virus (e.g., Hepatitis A, B, and C), herpes simplex virus (type 1 and 2), cytomegalovirus, herpes virus, HIV, influenza virus, measles virus, mumps virus, papillomavirus, parainfluenza virus, poliovirus, respiratory syncytial virus, rubella virus, and varicella-zoster virus. Examples of diseases or conditions caused by viruses include, but are not limited to, cold, flu, hepatitis, AIDS, chicken pox, rubella, mumps, measles, warts, and poliomyelitis.

The non-subject nucleic acid may be derived from a protozoan, such as *Acanthamoeba* (e.g., *A. astronyxis, A. castellanii, A. culbertsoni, A. hatchetti, A. polyphaga, A. rhysodes, A. healyi, A. divionensis*), *Brachiola* (e.g., *B. connori, B. vesicularum*), *Cryptosporidium* (e.g., *C. parvum*), *Cyclospora* (e.g., *C. cayetanensis*), *Encephalitozoon* (e.g., *E. cuniculi, E. hellem, E. intestinalis*), *Entamoeba* (e.g., *E. histolytica*), *Enterocytozoon* (e.g., *E. bieneusi*), Giardia (e.g., *G. lamblia*), *Isospora* (e.g., *I. belli*), *Microsporidium* (e.g., *M. africanum, M. ceylonensis*), *Naegleria* (e.g., *N. fowleri*), *Nosema* (e.g., *N. algerae, N. ocularum*), *Pleistophora, Trachipleistophora* (e.g., *T. anthropophthera, T. hominis*), and *Vittaforma* (e.g., *V. corneae*).

Nucleic acids can be extracted and/or isolated from a biological sample from a subject for instance by performing an isolation of a cellular fraction. In variations, sample processing can thus include any one or more of: lysing a sample, disrupting membranes in cells of a sample, separation of undesired elements (e.g., RNA, proteins) from the sample, purification of nucleic acids (e.g., DNA) in a sample to generate a nucleic acid sample comprising nucleic acid content of a non-human, microbiome, of a sample and nucleic acid content of a human genome, amplification of nucleic acids from the nucleic acid sample, further purification of amplified nucleic acids of the nucleic acid sample, sequencing of amplified nucleic acids of the nucleic acid sample, and any combination thereof. In variations, lysing a sample and/or disrupting membranes in cells of a sample can includes physical methods (e.g., bead beating, nitrogen decompression, homogenization, sonication) of cell lysing/membrane disruption, which omit certain reagents that produce bias in representation of certain microorganism groups upon sequencing. Additionally or alternatively, lysing or disrupting in can involve chemical methods (e.g., using a detergent, using a solvent, using a surfactant, etc.).

In variations, separation of undesired elements from the sample can include removal of RNA using RNases and/or removal of proteins using proteases. In variations, purification of nucleic acids in a sample to generate a nucleic acid sample can include one or more of: precipitation of nucleic acids from the biological samples (e.g., using alcohol-based precipitation methods), liquid-liquid based purification techniques (e.g., phenol-chloroform extraction), chromatography-based purification techniques (e.g., column adsorption), purification techniques involving use of binding moiety-bound particles (e.g., magnetic beads, buoyant beads, beads with size distributions, ultrasonically responsive beads, etc.) configured to bind nucleic acids and configured to release nucleic acids in the presence of an elution environment (e.g., having an elution solution, providing a pH shift, providing a temperature shift, etc.), and any other suitable purification techniques.

Nucleic acids can be extracted and/or isolated from a biological sample to extract and isolate and/or isolate can be conducted, in an environment (e.g., sterilized laboratory hood, sterilized room) sterilized of any contaminating substances (e.g., substances that may affect nucleic acids in a sample or contribute to contaminant nucleic acids), an environment can be temperature controlled, controlled for oxygen content, controlled for carbon dioxide content, and/or controlled for light exposure (e.g., exposure to ultraviolet light). Extraction can include lysing to disrupt cellular membranes and facilitate nucleic acid release from cells in a biological sample. In one non-limiting example, lysing can include a bead milling apparatus (e.g., a Tissue Lyser) configured for use with beads that are mixed with a sample and function to agitate biological content of the sample. In some cases, processing of a biological sample can comprise a combination of one or more of: lysing reagents (e.g., proteinases), heating modules, and any other suitable apparatus(es) for lysing.

For isolation of nucleic acids from a lysed sample, non-nucleic acid content of a sample is separation from nucleic acid content of a sample. A purification module of the sample processing method can comprise force-based separation, sized-based separation, binding-moiety-based separation (e.g., with magnetic binding moieties, with buoyant binding moieties, etc.), and/or any other suitable form of separation. For instance, a purification operation of a method can include one or more of: a centrifuge to facilitate extraction of a supernatant, a filter (e.g., a filtration plate), a fluid delivery module configured to combine a lysed sample with moieties that bind to nucleic acid content and/or waste material of a sample, a wash reagent delivery system, an elution reagent delivery system, and any other suitable apparatus for purification of nucleic acid content from a sample.

A subset of nucleic acid molecules can be subject to an assay to yield sequence information. An assay that yields sequence information can induce sequencing reactions. In some cases, sequencing can be of RNA. For example sequencing can be of RNA transcription. Sequencing of RNA can comprise any one of: Chromatin Isolation by RNA Purification (ChIRP-Seq), Global Run-on Sequencing (GRO-Seq), Ribosome Profiling Sequencing (Ribo-Seq)/ARTseq™, RNA Immunoprecipitation Sequencing (RIP-Seq), High-Throughput Sequencing of CLIP cDNA library (HITS-CLIP), Crosslinking and Immunoprecipitation Sequencing (CLIP-Seq), Photoactivatable Ribonucleoside-Enhanced Crosslinking and Immunoprecipitation (PAR-CLIP), Individual Nucleotide Resolution CLIP (iCLIP), Native Elongating Transcript Sequencing (NET-Seq), Targeted Purification of Polysomal mRNA (TRAP-Seq), Crosslinking, Ligation, and Sequencing of Hybrids (CLASH-Seq), Parallel Analysis of RNA Ends Sequencing (PARE-Seq), Genome-Wide Mapping of Uncapped Transcripts (GMUCT), Transcript Isoform Sequencing (TIF-Seq), Paired-End Analysis of TSSs (PEAT), and any combinations thereof. In some cases, sequencing can comprise RNA structure. Sequencing of RNA structure can comprise any one of: Selective 2'-Hydroxyl Acylation Analyzed by Primer Extension Sequencing (SHAPE-Seq), Parallel Analysis of RNA Structure (PARS-Seq) Fragmentation Sequencing (FRAG-Seq), CXXC Affinity Purification Sequencing (CAP-Seq), Alkaline Phosphatase, Calf Intestine-Tobacco Acid Pyrophosphatase Sequencing (CIP-TAP), Inosine Chemical Erasing Sequencing (ICE), m6A-Specific Methylated RNA Immunoprecipitation Sequencing (MeRIP-Seq), and any combinations thereof. In some cases, sequencing can comprise Low-Level RNA Detection. Low-level RNA detection can comprise: Digital RNA Sequencing, Whole-Transcript Amplification for Single Cells (Quartz-Seq), Designed Primer-Based RNA Sequencing (DP-Seq), Switch Mechanism at the 5' End of RNA Templates (Smart-Seq), Switch Mechanism at the 5' End of RNA Templates Version 2 (Smart-Seq2), Unique Molecular Identifiers (UMI), Cell Expression by Linear Amplification Sequencing (CEL-Seq), Single-Cell Tagged Reverse Transcription Sequencing (STRT-Seq), and any combination thereof. In some cases, sequencing can be of DNA. DNA sequencing can comprise low-level DNA detection. DNA sequencing that comprises low-level DNA detection can comprise at least one of Single-Molecule Molecular Inversion Probes (smMIP), Multiple Displacement Amplification (MDA), Multiple Annealing and Looping-Based Amplification Cycles (MALBAC), Oligonucleotide-Selective Sequencing (OS-Seq), Duplex Sequencing (Duplex-Seq), and any combinations thereof. In some aspects, sequencing can comprise DNA methylation. DNA methylation can comprise at least one of: Bisulfite Sequencing (BS-Seq), Post-Bisulfite Adapter Tagging (PBAT), Tagmentation-Based Whole Genome Bisulfite Sequencing (T-WGBS), Oxidative Bisulfite Sequencing (oxBS-Seq), Tet-Assisted Bisulfite Sequencing (TAB-Seq), Methylated DNA Immunoprecipitation Sequencing (MeDIP-Seq), Methylation-Capture (MethylCap) Sequencing, Methyl-Binding-Domain-Capture (MBDCap) Sequencing, Reduced-Representation Bisulfite Sequencing (RRBS-Seq), and an combination thereof. In some cases, sequencing can comprise DNA-protein interactions. For example sequencing comprising DNA-protein interactions can comprise: DNase 1 Hypersensitive Sites Sequencing (DNase-Seq), MNase-Assisted Isolation of Nucleosomes Sequencing (MAINE-Seq), Chromatin Immunoprecipitation Sequencing (ChIP-Seq), Formaldehyde-Assisted Isolation of Regulatory Elements (FAIRE-Seq), Assay for Transposase-Accessible Chromatin Sequencing (ATAC-Seq), Chromatin Interaction Analysis by Paired-End Tag Sequencing (ChIA-PET), Chromatin Conformation Capture (Hi-C/3C-Seq), Circular Chromatin Conformation Capture (4-C or 4C-Seq), Chromatin Conformation Capture Carbon Copy (5-C), and combinations thereof. In some cases, sequencing can comprise rearrangements. Sequencing of sequence rearrangements can comprise at least one of: Retrotransposon Capture Sequencing (RC-Seq), Transposon Sequencing (Tn-Seq) or Insertion Sequencing (INSeq), Translocation-Capture Sequencing (TC-Seq), and combinations thereof.

A sequencing analysis can comprise PCR amplification, for instance subsections of the 16S ribosomal RNA gene, and untargeted, metagenomics, methods that use deep sequencing. In some embodiments, a method can comprise, a process for next generation amplification and sequencing can include simultaneously amplifying an entire 16S region for each of a set of microorganisms, fragmenting amplicons of the entire 16S region for each of the set of microorganisms to generate a set of amplicon fragments, and generating an analysis based upon the set of amplicon fragments wherein the analysis includes at least one of microorganism population characteristics, microorganism species identifications, and identified target microorganism sequences. In some cases, whole exomic sequencing can be utilized.

In some cases, a method can comprise an alignment at the genetic level of a non-human genome. For example, an alignment can comprise aligning 16S sequences, in relation to 18S sequences, in relation to ITS sequences, and the like. Outputs can thus be used to identify features of interest which can be used to characterize the microbiomes of a biological sample wherein the features can be non-human (e.g., presence of a genus of bacteria), genetic-based (e.g., based upon representation of specific genetic regions and/or sequences), and/or based at any other suitable scale.

In variations, alignment and mapping to reference non-human genome, for instance a bacterial genomes (e.g., provided by the National Center for Biotechnology Information), can be performed using an alignment algorithm including one or more of: a Needleman-Wunsch algorithm that performs a global alignment of two reads (e.g., a sequencing read and a reference read) with a stopping condition based upon scoring of the global alignment (e.g., in terms of insertions, deletions, matches, mismatches); a Smith-waterman algorithm that performs a local alignment of two reads (e.g., a sequencing read and a reference read) with scoring of the local alignment (e.g., in terms of insertions, deletions, matches, mismatches); a Basic Local Alignment Search Tool (BLAST) that identifies regions of local similarity between sequences (e.g., a sequencing read and a reference read); a FPGA accelerated alignment tool; a BWT-indexing with BWA tool; a BWT-indexing with SOAP tool; a BWT-indexing with Bowtie tool; Sequence Search and Alignment by Hashing Algorithm (SSAHA2) that maps nucleic acid sequencing reads onto a genomic reference sequence using word hashing and dynamic programming; and any other suitable alignment algorithm. Mapping of unidentified sequences in can further include mapping to reference viral genomes and/or fungal genomes, in order to further identify viral and/or fungal components of the microbiome of an individual. For instance, PCR can be performed with multiple markers (e.g., a first marker, a second marker, a third marker, an Nth marker) in parallel or in series, and associated with one or more of bacterial markers, fungal markers, and eukaryotic markers. Furthermore, overlapping reads (e.g., generated by paired end sequencing) can be assembled based upon outputs of the alignment algorithm, or aligned sequence reads can be merged with reference sequences (e.g., using a hidden Markov model banding technique, using a Durbin-Holmes technique). Alignment and mapping in can, however, implement any other suitable algorithm or technique. In some cases, sequence reads can be encoded to facilitate alignment and mapping operations performed. In one example, each base of a sequence can be encoded as a byte according to the arrangement 0000TGCA, whereby the least significant bit is 1 if the base is sequenced as possibly containing the base A (e.g., A is represented as 00000001), the next significant bit is 1 if the base is sequenced as possibly containing the base C (e.g., C is represented as 00000010), the next significant bit is 1 if the base is sequenced as possibly containing the base G (e.g., G is represented as 00000100), and the next significant bit is 1 if the base is sequenced as possibly containing the base T (e.g., T is represented as 00001000). In the example, the four most significant bits are set to zero. However, alternative variations of the example can encode bases in any other suitable manner. Furthermore, predetermined sequences of primers used during amplification can be used to trim sequence reads to omit primer sequences to increase the efficiency of alignment and mapping.

Figure 6A:
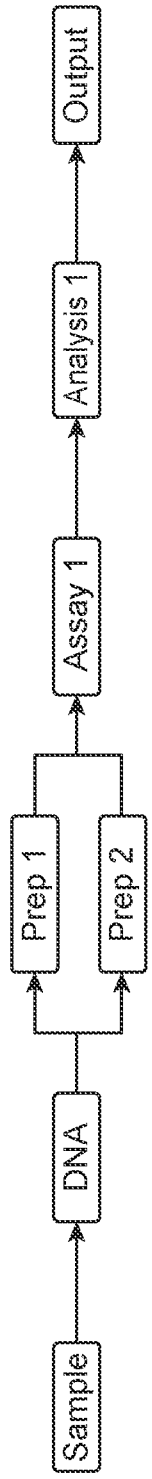
FIG. 6A shows a schematic of a workflow. Prep 1 and Prep 2 refer to subsets of nucleic acids. Assay 1, Analysis 1, and Output refer to any assay, analysis, and output described herein.

Subsets of nucleic acid molecules may comprise one or more genomes as disclosed herein. Subsets of nucleic acid molecules may comprise 1 or more, 2 or more, 3 or more, 4 or more, 5 or more, 6 or more, 7 or more, 8 or more, 9 or more, 10 or more, 11 or more, 12 or more, 13 or more, 14 or more, 15 or more, 20 or more, 25 or more, 30 or more, 35 or more, 40 or more, 50 or more, 60 or more, 70 or more, 80 or more, 90 or more, or 100 or more genomes. The one or more genomes may be identical, similar, different, or a combination thereof. In some cases, there are two subsets of nucleic acids, FIG. 6A.

Subsets of nucleic acid molecules may comprise one or more genome features as disclosed herein. Subsets of nucleic acid molecules may comprise 1 or more, 2 or more, 3 or more, 4 or more, 5 or more, 6 or more, 7 or more, 8 or more, 9 or more, 10 or more, 11 or more, 12 or more, 13 or more, 14 or more, 15 or more, 20 or more, 25 or more, 30 or more, 35 or more, 40 or more, 50 or more, 60 or more, 70 or more, 80 or more, 90 or more, or 100 or more genome features. The one or more genome features may be identical, similar, different, or a combination thereof.

Subsets of nucleic acid molecules may comprise nucleic acid molecules of different sizes. The length of a nucleic acid molecule in a subset of nucleic acid molecules may be referred to as the size of the nucleic acid molecule. The average length of the nucleic acid molecules in a subset of nucleic acid molecules may be referred to as the mean size of nucleic acid molecules. As used herein, the terms "size of a nucleic acid molecule", "mean size of nucleic acid molecules", "molecular size" and "mean molecular size" may be used interchangeably. The size of a nucleic acid molecule may be used to differentiate two or more subsets of nucleic acid molecules. The difference in the mean size of nucleic acid molecules in a subset of nucleic acid molecules and the mean size of nucleic acid molecules in another subset of nucleic acid molecules may be used to differentiate the two subsets of nucleic acid molecules. The mean size of nucleic acid molecules in one subset of nucleic acid molecules may be greater than the mean size of nucleic acid molecules in at least one other subset of nucleic acid molecules. The mean size of nucleic acid molecules in one subset of nucleic acid molecules may be less than the mean size of nucleic acid molecules in at least one other subset of nucleic acid molecules. The difference in mean molecular size between two or more subsets of nucleic acid molecules may be at least about 50; 75; 100; 125; 150; 175; 200; 225; 250; 275; 300; 350; 400; 450; 500; 550; 600; 650; 700; 750; 800; 850; 900; 950; 1,000; 1100; 1200; 1300; 1400; 1500; 1600; 1700; 1800; 1900; 2,000; 3,000; 4,000; 5,000; 6,000; 7,000; 8,000; 9,000; 10,000; 15,000; 20,000; 30,000; 40,000; 50,000; 60,000; 70,000; 80,000; 90,000; 100,000 or more bases or base pairs. In some aspects of the disclosure, the difference in mean molecular size between two or more subsets of nucleic acid molecules is at least about 200 bases or bases pairs. Alternatively, the difference in mean molecular size between two or more subsets of nucleic acid molecules is at least about 300 bases or bases pairs.

Subsets of nucleic acid molecules may comprise nucleic acid molecules of different sequencing sizes. The length of a nucleic acid molecule in a subset of nucleic acid molecules to be sequenced may be referred to as the sequencing size of the nucleic acid molecule. The average length of the nucleic acid molecules in a subset of nucleic acid molecules may be referred to as the mean sequencing size of nucleic acid molecules. As used herein, the terms "sequencing size of a nucleic acid molecule", "mean sequencing size of nucleic acid molecules", "molecular sequencing size" and "mean molecular sequencing size" may be used interchangeably. The mean molecular sequencing size of one or more subsets of nucleic acid molecules may be at least about 50; 75; 100; 125; 150; 175; 200; 225; 250; 275; 300; 350; 400; 450; 500; 550; 600; 650; 700; 750; 800; 850; 900; 950; 1,000; 1100; 1200; 1300; 1400; 1500; 1600; 1700; 1800; 1900; 2,000; 3,000; 4,000; 5,000; 6,000; 7,000; 8,000; 9,000; 10,000; 15,000; 20,000; 30,000; 40,000; 50,000; 60,000; 70,000; 80,000; 90,000; 100,000 or more bases or base pairs. The sequencing size of a nucleic acid molecule may be used to differentiate two or more subsets of nucleic acid molecules. The difference in the mean sequencing size of nucleic acid molecules in a subset of nucleic acid molecules and the mean sequencing size of nucleic acid molecules in another subset of nucleic acid molecules may be used to differentiate the two subsets of nucleic acid molecules. The mean sequencing size of nucleic acid molecules in one subset of nucleic acid molecules may be greater than the mean sequencing size of nucleic acid molecules in at least one other subset of nucleic acid molecules. The mean sequencing size of nucleic acid molecules in one subset of nucleic acid molecules may be less than the mean sequencing size of nucleic acid molecules in at least one other subset of nucleic acid molecules. The difference in mean molecular sequencing size between two or more subsets of nucleic acid molecules may be at least about 50; 75; 100; 125; 150; 175; 200; 225; 250; 275; 300; 350; 400; 450; 500; 550; 600; 650; 700; 750; 800; 850; 900; 950; 1,000; 1100; 1200; 1300; 1400; 1500; 1600; 1700; 1800; 1900; 2,000; 3,000; 4,000; 5,000; 6,000; 7,000; 8,000; 9,000; 10,000; 15,000; 20,000; 30,000; 40,000; 50,000; 60,000; 70,000; 80,000; 90,000; 100,000 or more bases or base pairs. In some aspects of the disclosure, the difference in mean molecular sequencing size between two or more subsets of nucleic acid molecules is at least about 200 bases or bases pairs. Alternatively, the difference in mean molecular sequencing size between two or more subsets of nucleic acid molecules is at least about 300 bases or bases pairs.

The methods disclosed herein may comprise one or more capture probes, a plurality of capture probes, or one or more capture probe sets. Typically, the capture probe comprises a nucleic acid binding site. The capture probes may hybridize to the captured nucleic acid. The capture probes may comprise a nucleic acid sequence that is complementary to the captured nucleic acid. In some cases, the capture probes may comprise a nucleic acid sequence that is completely complementary to a portion of the captured nucleic acid. For example, each nucleic acid in a capture probe may be complementary to a base in the captured nucleic acid. The capture probe may be longer than the capture nucleic acid. For example, each of the bases in the captured nucleic acid may be complementary to a base in the capture probe, but not all bases in the capture probe are complementary to a base in the captured nucleic acid. The capture probes may be shorter than the captured nucleic acid. For example, each of the bases of the capture probe may be complementary to a base of the captured nucleic acid, but not all bases in captured nucleic acid may be complementary to the capture probe.

The capture probes may perform a capture reaction in solution. The capture probes may be in solution and capture a nucleic acid in solution. Captured nucleic acids may be subsequently isolated and/or eluted, as described elsewhere herein. The capture probe may capture a nucleic acid in solution and then the capture probe may be subsequently attached to a support, such as a solid support (e.g., an array or bead). In some situations, the support may be formed of a semi-solid material (e.g., a gel).

Attachment to a support may be a non-covalent attachment. For example, a nucleic acid may be captured by a biotinylated probe which is subsequently bound to an avidin/streptavidin bead, thereby attaching the captured nucleic acid complex to an avidin/streptavidin bead. Other binding pairs may be used to attach the capture probe to the surface. Capture probes can be covalently attached to the support. For example the support may have chemically reactive linkers that may react with the capture probes such that the capture probes are covalently linked to the support.

The capture probes may be attached to a support and perform a capture reaction. For example the capture probes may be coupled to the support and subsequently capture a nucleic acid molecule. The support may be a solid or semi-solid (e.g., a gel) material. Examples of supports include, without limitation, beads, slides, and chips. A support can be, for example, glass, silica, silicon, plastic (such as polysterene), agar or agarose.

The capture probe may further comprise one or more linkers. The capture probes may further comprise one or more labels. The one or more linkers may attach the one or more labels to the nucleic acid binding site. In some cases, capture probes may be designed to hybridize to the shared regions of a 16S gene sequence. A capture probe that can be designed to target a shared region of a 16S gene sequence can be used to capture nucleic acid molecules from a wide variety of species, even species which have yet to be identified and characterized. In some cases, a method can comprise a first plurality of nucleic acid probes configured to target elements of a human genome sequence. In some cases, a method can comprise a second plurality of nucleic acid probes that are configured to target elements from genome sequences of a non-human species.

The methods disclosed herein may comprise 1 or more, 2 or more, 3 or more, 4 or more, 5 or more, 6 or more, 7 or more, 8 or more, 9 or more, 10 or more, 20 or more, 30 or more, 40 or more, 50 or more, 60 or more, 70 or more, 80 or more, 90 or more, 100 or more, 125 or more, 150 or more, 175 or more, 200 or more, 250 or more, 300 or more, 350 or more, 400 or more, 500 or more, 600 or more, 700 or more, 800 or more, 900 or more, 1000 or more, 5000 or more, 10,000 or more, 20,000 or more, 30,000 or more, 40,000 or more, 50,000 or more, 60,000 or more, 70,000 or more, 80,000 or more, 90,000 or more, 100,0000 or capture probes or capture probe sets. In some cases, a method can comprise from about 50,000 capture probes. The one or more capture probes or capture probe sets may be different, similar, identical, or a combination thereof. The one or more capture probes or capture probe sets may be in varying relative concentrations compared to other capture probes. For example, some capture probes may be in a greater concentration to capture nucleic acid that may be difficult to capture (e.g., sequences with high GC content, sequences that are the result of sequence recombination, sequences with high numbers of mutations, sequences that have high mutation rates), and thereby increase the probability of capturing a specific nucleic acid.

The one or more capture probe may comprise a nucleic acid binding site that hybridizes to at least a portion of the one or more nucleic acid molecules or variant or derivative thereof in the sample or subset of nucleic acid molecules. The capture probes may comprise a nucleic acid binding site that hybridizes to one or more genomes. The capture probes may hybridize to different, similar, and/or identical genomes. The one or more capture probes may be at least about 50%, 55%, 60%, 65%, 70%, 75%, 80%, 85%, 90%, 95%, 97%, 99% or more complementary to the one or more nucleic acid molecules or variant or derivative thereof.

The capture probes may comprise one or more nucleotides. The capture probes may comprise 1 or more, 2 or more, 3 or more, 4 or more, 5 or more, 6 or more, 7 or more, 8 or more, 9 or more, 10 or more, 20 or more, 30 or more, 40 or more, 50 or more, 60 or more, 70 or more, 80 or more, 90 or more, 100 or more, 125 or more, 150 or more, 175 or more, 200 or more, 250 or more, 300 or more, 350 or more, 400 or more, 500 or more, 600 or more, 700 or more, 800 or more, 900 or more, or 1000 or more nucleotides. The capture probes may comprise about 100 nucleotides. The capture probes may comprise between about 10 to about 500 nucleotides, between about 20 to about 450 nucleotides, between about 30 to about 400 nucleotides, between about 40 to about 350 nucleotides, between about 50 to about 300 nucleotides, between about 60 to about 250 nucleotides, between about 70 to about 200 nucleotides, or between about 80 to about 150 nucleotides. In some aspects of the disclosure, the capture probes comprise between about 80 nucleotides to about 100 nucleotides.

The plurality of capture probes or the capture probe sets may comprise two or more capture probes with identical, similar, and/or different nucleic acid binding site sequences, linkers, and/or labels. For example, two or more capture probes comprise identical nucleic acid binding sites. In another example, two or more capture probes comprise similar nucleic acid binding sites. In yet another example, two or more capture probes comprise different nucleic acid binding sites. The two or more capture probes may further comprise one or more linkers. The two or more capture probes may further comprise different linkers. The two or more capture probes may further comprise similar linkers. The two or more capture probes may further comprise identical linkers. The two or more capture probes may further comprise one or more labels. The two or more capture probes may further comprise different labels. The two or more capture probes may further comprise similar labels. The two or more capture probes may further comprise identical labels.

Figure 6B:
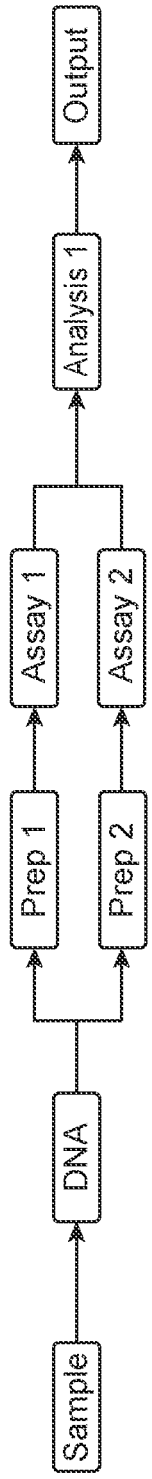
FIG. 6B shows a schematic of a workflow. Prep 1 and Prep 2 refer to subsets of nucleic acids. Assay 1, Assay 2, Analysis 1, and Output refer to any assay, analysis, and output described herein.
Figure 6C:
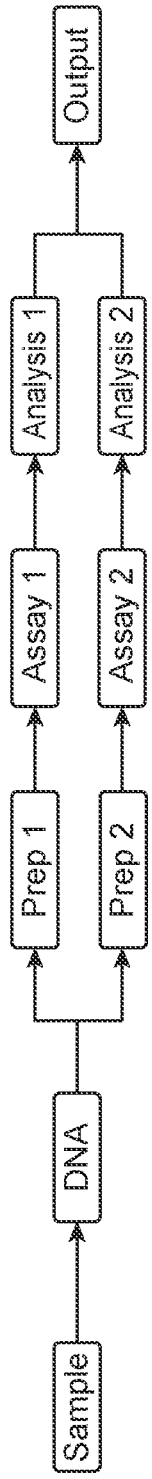
FIG. 6C shows a schematic of a workflow. Prep 1 and Prep 2 refer to subsets of nucleic acids. Assay 1, Assay 2, Analysis 1, Analysis 2, and Output refer to any assay, analysis, and output described herein.
Figure 6D:
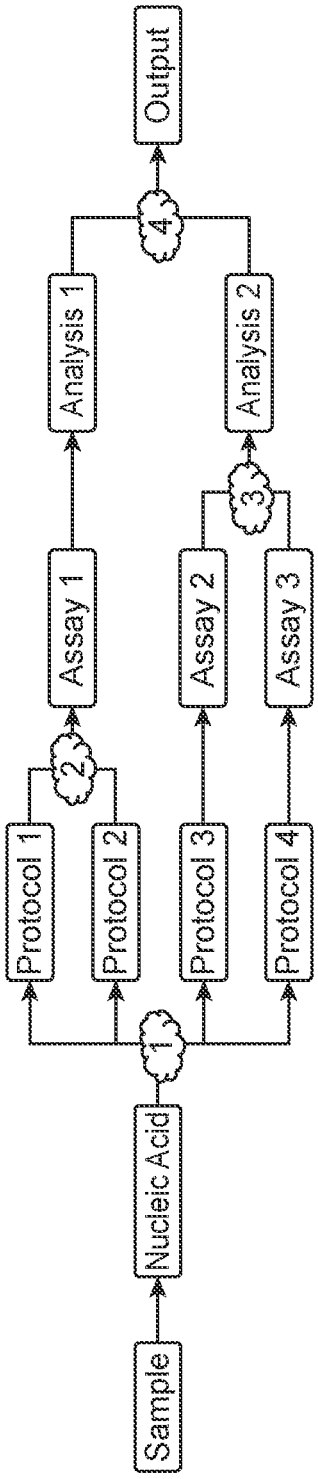
FIG. 6D shows a schematic of a workflow comprising (1) separation of the nucleic acid sample into several subsets processed with several protocols. These protocols may involve enrichment for different genomic or non-genomic regions and comprise one or more different amplification operations to prepare libraries of nucleic acid molecules for an assay. Some of these libraries may combined (2) for assay. Results of some assays may be combined (3) for subsequent analysis. Variant calls or other assessments of sequence or genetic state may be further combined (4) to produce a combined assessment at east locus addressed by the assay. Protocols 1-4 refer to any method described herein. Assay 1, Assay 2, Assay 3, Analysis 1, Analysis 2, and Output refer to any assay, analysis, and output described herein.
Figure 8:
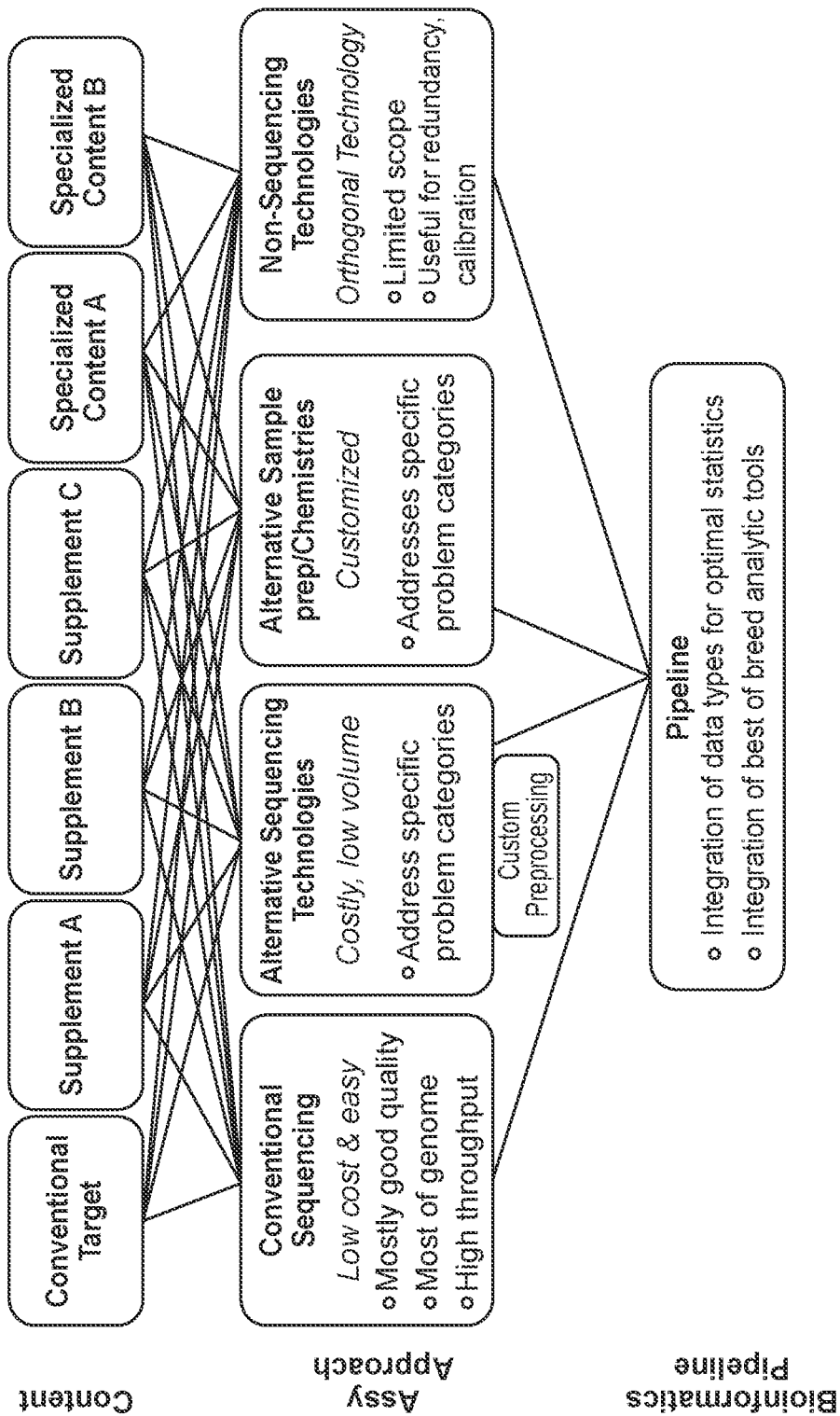
FIG. 8 shows a schematic of a workflow of the present disclosure.
Figure 9:
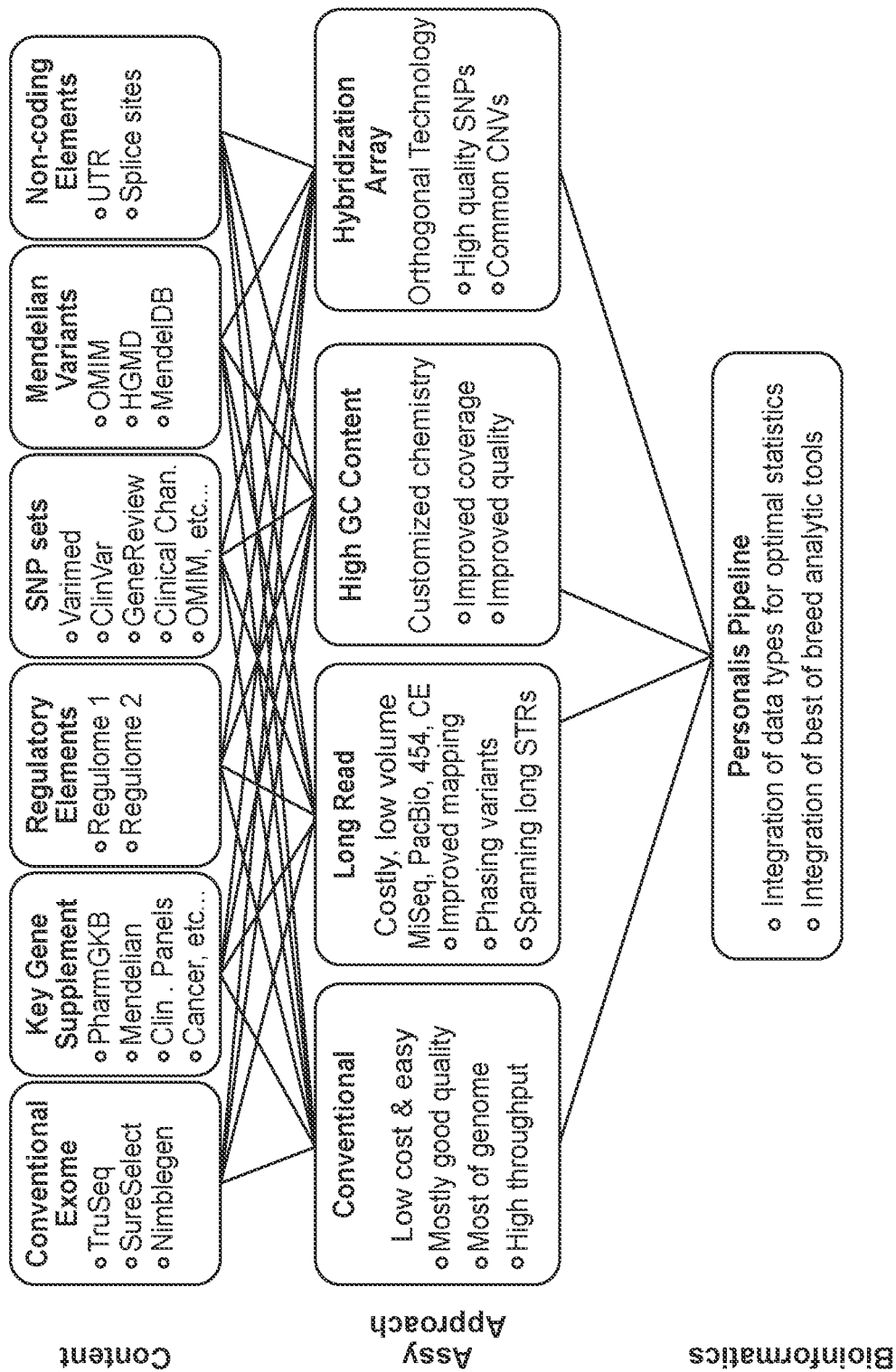
FIG. 9 shows a schematic of a workflow of the present disclosure.

Assays may include, but are not limited to, sequencing, amplification, hybridization, enrichment, isolation, elution, fragmentation, detection, quantification of one or more nucleic acid molecules. Assays may include methods for preparing one or more nucleic acid molecules. Assays may comprise conventional assays, long read, high GC content, and hybridization assays, FIG. 9. Any number of assays may be performed. A number of assays may be 1, 2, 3, 4, 5, 6, 7, 8, 9, or up to 10 assays. For example, FIG. 6B illustrates a schematic showing utilization of two assays. Similarly, any number of analysis of data from one or more assays may be performed. A number of analysis may be 1, 2, 3, 4, 5, 6, 7, 8, 9, or up to 10 analysis of data from one or more assays. For example, FIG. 6C illustrates two different analysis being performed. In some cases, an analysis is a bioinformatics analysis, FIG. 8. An assay may be performed using any number of protocols. For example, from 1, 2, 3, 4, 5, 6, 7, 8, 9, or up to 10 protocols may be utilized. FIG. 6D provides a schematic utilizing 4 protocols.

The methods disclosed herein may comprise conducting one or more sequencing reactions on one or more nucleic acid molecules in a sample. The methods disclosed herein may comprise conducting 1 or more, 2 or more, 3 or more, 4 or more, 5 or more, 6 or more, 7 or more, 8 or more, 9 or more, 10 or more, 15 or more, 20 or more, 30 or more, 40 or more, 50 or more, 60 or more, 70 or more, 80 or more, 90 or more, 100 or more, 200 or more, 300 or more, 400 or more, 500 or more, 600 or more, 700 or more, 800 or more, 900 or more, or 1000 or more sequencing reactions on one or more nucleic acid molecules in a sample. Sequencing reactions may be run simultaneously, sequentially, or a combination thereof. Sequencing reactions may comprise whole genome sequencing or exome sequencing. Sequencing reactions may comprise Maxim-Gilbert, chain-termination or high-throughput systems. Alternatively, or additionally, sequencing reactions may comprise Helioscope™ single molecule sequencing, Nanopore DNA sequencing, Lynx Therapeutics' Massively Parallel Signature Sequencing (MPSS), 454 pyrosequencing, Single Molecule real time (RNAP) sequencing, Illumina (Solexa) sequencing, SOLiD sequencing, Ion Torrent™, Ion semiconductor sequencing, Single Molecule SMRT™ sequencing, Polony sequencing, DNA nanoball sequencing, VisiGen Biotechnologies approach, or a combination thereof. Alternatively, or additionally, sequencing reactions can comprise one or more sequencing platforms, including, but not limited to, Genome Analyzer IIx, HiSeq, and MiSeq offered by Illumina, Single Molecule Real Time (SMRT™) technology, such as the PacBio RS system offered by Pacific Biosciences (California) and the Solexa Sequencer, True Single Molecule Sequencing (tSMS™) technology such as the HeliScope™ Sequencer offered by Helicos Inc. (Cambridge, Mass.). Sequencing reactions may also comprise electron microscopy or a chemical-sensitive field effect transistor (chemFET) array. In some aspects of the disclosure, sequencing reactions comprise capillary sequencing, next generation sequencing, Sanger sequencing, sequencing by synthesis, sequencing by ligation, sequencing by hybridization, single molecule sequencing, or a combination thereof. Sequencing by synthesis may comprise reversible terminator sequencing, processive single molecule sequencing, sequential flow sequencing, or a combination thereof. Sequential flow sequencing may comprise pyrosequencing, pH-mediated sequencing, semiconductor sequencing, or a combination thereof.

Figure 18:
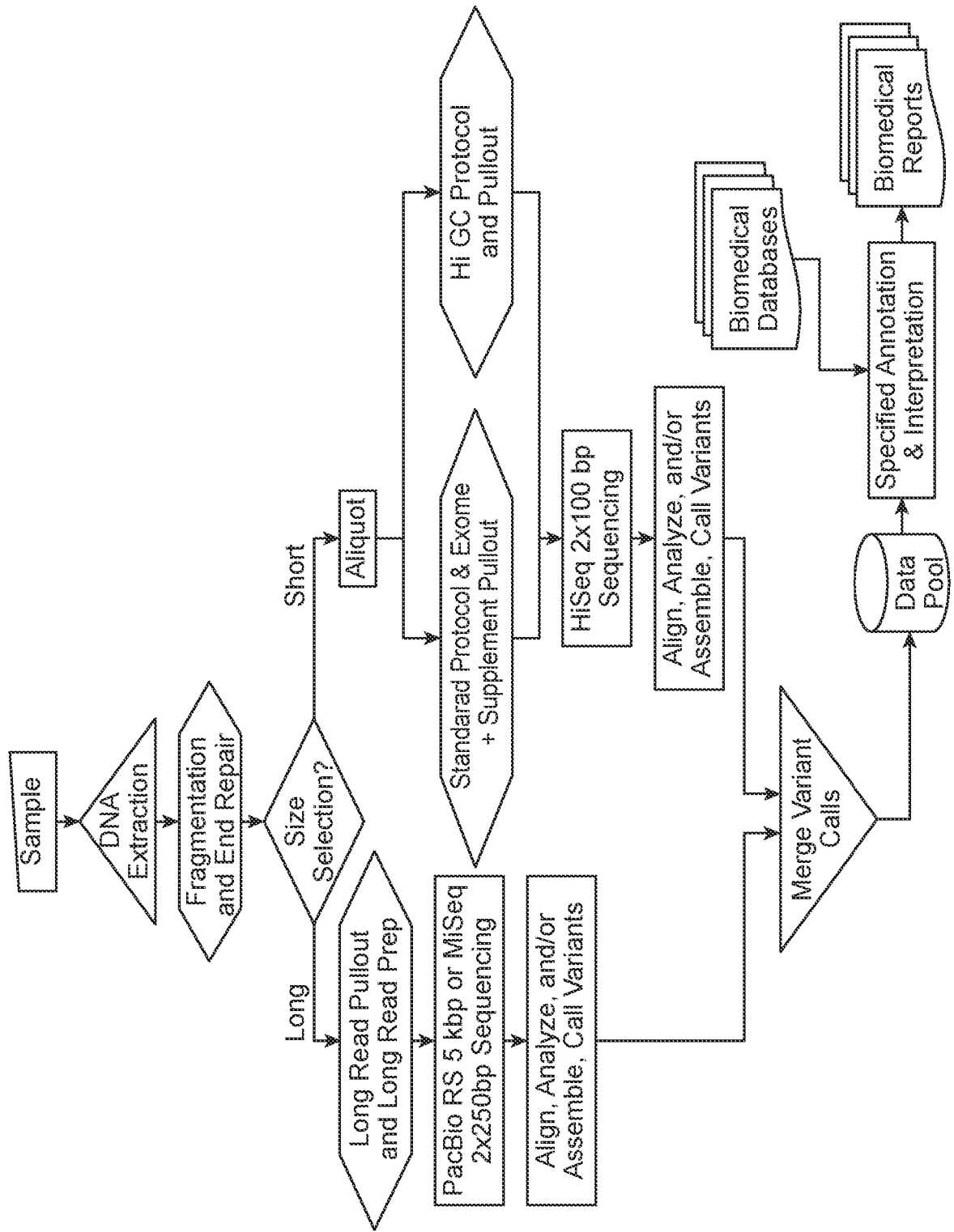
FIG. 18 depicts a multi-threaded assay comprising two subsets of DNA produced by size selection and further divided into two subsets of DNA enriched for different genomic regions based on GC content. The longer molecules may undergo sequencing using a technology appropriate for longer molecules. The two shorter molecule subsets may be further prepared and amplified based on protocols appropriate to the $T_m$ of the subsets then pooled for sequencing on a high throughput short read sequencer, the HiSeq. Primary data from the sequencing may be merged and analyzed (e.g., by one or more software programs or algorithms) to produce a single best result for all of the regions addressed by the subsets and resulting in a data pool that may be used for one or more biomedical reports. A supplement pullout may include human target sequences and non-human target sequences.

The methods disclosed herein may comprise conducting at least one long read sequencing reaction and at least one short read sequencing reaction. An example of a method comprising long and short read sequencing is illustrated in FIG. 18. The long read sequencing reaction and/or short read sequencing reaction may be conducted on at least a portion of a subset of nucleic acid molecules. The long read sequencing reaction and/or short read sequencing reaction may be conducted on at least a portion of two or more subsets of nucleic acid molecules. Both a long read sequencing reaction and a short read sequencing reaction may be conducted on at least a portion of one or more subsets of nucleic acid molecules.

Sequencing of the one or more nucleic acid molecules or subsets thereof may comprise at least about 5; 10; 15; 20; 25; 30; 35; 40; 45; 50; 60; 70; 80; 90; 100; 200; 300; 400; 500; 600; 700; 800; 900; 1,000; 1500; 2,000; 2500; 3,000; 3500; 4,000; 4500; 5,000; 5500; 6,000; 6500; 7,000; 7500; 8,000; 8500; 9,000; 10,000; 25,000; 50,000; 75,000; 100,000; 250,000; 500,000; 750,000; 10,000,000; 25,000,000; 50,000,000; 100,000,000; 250,000,000; 500,000,000; 750,000,000; 1,000,000,000 or more sequencing reads.

Sequencing reactions may comprise sequencing at least about 50; 60; 70; 80; 90; 100; 110; 120; 130; 140; 150; 160; 170; 180; 190; 200; 210; 220; 230; 240; 250; 260; 270; 280; 290; 300; 325; 350; 375; 400; 425; 450; 475; 500; 600; 700; 800; 900; 1,000; 1500; 2,000; 2500; 3,000; 3500; 4,000; 4500; 5,000; 5500; 6,000; 6500; 7,000; 7500; 8,000; 8500; 9,000; 10,000; 20,000; 30,000; 40,000; 50,000; 60,000; 70,000; 80,000; 90,000; 100,000 or more bases or base pairs of one or more nucleic acid molecules. Sequencing reactions may comprise sequencing at least about 50; 60; 70; 80; 90; 100; 110; 120; 130; 140; 150; 160; 170; 180; 190; 200; 210; 220; 230; 240; 250; 260; 270; 280; 290; 300; 325; 350; 375; 400; 425; 450; 475; 500; 600; 700; 800; 900; 1,000; 1500; 2,000; 2500; 3,000; 3500; 4,000; 4500; 5,000; 5500; 6,000; 6500; 7,000; 7500; 8,000; 8500; 9,000; 10,000; 20,000; 30,000; 40,000; 50,000; 60,000; 70,000; 80,000; 90,000; 100,000 or more consecutive bases or base pairs of one or more nucleic acid molecules.

The sequencing techniques used in methods of the present disclosure may generate at least 100 reads per run, at least 200 reads per run, at least 300 reads per run, at least 400 reads per run, at least 500 reads per run, at least 600 reads per run, at least 700 reads per run, at least 800 reads per run, at least 900 reads per run, at least 1000 reads per run, at least 5,000 reads per run, at least 10,000 reads per run, at least 50,000 reads per run, at least 100,000 reads per run, at least 500,000 reads per run, or at least 1,000,000 reads per run. Alternatively, the sequencing technique used in the methods of the present disclosure may generate at least 1,500,000 reads per run, at least 2,000,000 reads per run, at least 2,500,000 reads per run, at least 3,000,000 reads per run, at least 3,500,000 reads per run, at least 4,000,000 reads per run, at least 4,500,000 reads per run, or at least 5,000,000 reads per run.

The sequencing techniques used in the methods of the present disclosure may generate can generate at least about 30 base pairs, at least about 40 base pairs, at least about 50 base pairs, at least about 60 base pairs, at least about 70 base pairs, at least about 80 base pairs, at least about 90 base pairs, at least about 100 base pairs, at least about 110, at least about 120 base pairs per read, at least about 150 base pairs, at least about 200 base pairs, at least about 250 base pairs, at least about 300 base pairs, at least about 350 base pairs, at least about 400 base pairs, at least about 450 base pairs, at least about 500 base pairs, at least about 550 base pairs, at least about 600 base pairs, at least about 700 base pairs, at least about 800 base pairs, at least about 900 base pairs, or at least about 1,000 base pairs per read. Alternatively, the sequencing technique used in the methods of the present disclosure may generate long sequencing reads. In some instances, the sequencing technique used in the methods of the present disclosure may generate at least about 1,200 base pairs per read, at least about 1,500 base pairs per read, at least about 1,800 base pairs per read, at least about 2,000 base pairs per read, at least about 2,500 base pairs per read, at least about 3,000 base pairs per read, at least about 3,500 base pairs per read, at least about 4,000 base pairs per read, at least about 4,500 base pairs per read, at least about 5,000 base pairs per read, at least about 6,000 base pairs per read, at least about 7,000 base pairs per read, at least about 8,000 base pairs per read, at least about 9,000 base pairs per read, at least about 10,000 base pairs per read, 20,000 base pairs per read, 30,000 base pairs per read, 40,000 base pairs per read, 50,000 base pairs per read, 60,000 base pairs per read, 70,000 base pairs per read, 80,000 base pairs per read, 90,000 base pairs per read, or 100,000 base pairs per read.

High-throughput sequencing systems may allow detection of a sequenced nucleotide immediately after or upon its incorporation into a growing strand, i.e., detection of sequence in real time or substantially real time. In some cases, high throughput sequencing generates at least 1,000, at least 5,000, at least 10,000, at least 20,000, at least 30,000, at least 40,000, at least 50,000, at least 100,000 or at least 500,000 sequence reads per hour; with each read being at least 50, at least 60, at least 70, at least 80, at least 90, at least 100, at least 120, at least 150, at least 200, at least 250, at least 300, at least 350, at least 400, at least 450, or at least 500 bases per read. Sequencing can be performed using nucleic acids described herein such as genomic DNA, cDNA derived from RNA transcripts or RNA as a template.

The methods disclosed herein may comprise conducting one or more amplification reactions on one or more nucleic acid molecules in a sample. The term "amplification" refers to any process of producing at least one copy of a nucleic acid molecule. The terms "amplicons" and "amplified nucleic acid molecule" refer to a copy of a nucleic acid molecule and can be used interchangeably. The amplification reactions can comprise PCR-based methods, non-PCR based methods, or a combination thereof. Examples of non-PCR based methods include, but are not limited to, multiple displacement amplification (MDA), transcription-mediated amplification (TMA), nucleic acid sequence-based amplification (NASBA), strand displacement amplification (SDA), real-time SDA, rolling circle amplification, or circle-to-circle amplification. PCR-based methods may include, but are not limited to, PCR, HD-PCR, Next Gen PCR, digital RTA, or any combination thereof. Additional PCR methods include, but are not limited to, linear amplification, allele-specific PCR, Alu PCR, assembly PCR, asymmetric PCR, droplet PCR, emulsion PCR, helicase dependent amplification HDA, hot start PCR, inverse PCR, linear-after-the-exponential (LATE)-PCR, long PCR, multiplex PCR, nested PCR, hemi-nested PCR, quantitative PCR, RT-PCR, real time PCR, single cell PCR, and touchdown PCR.

The methods disclosed herein may comprise conducting one or more hybridization reactions on one or more nucleic acid molecules in a sample. The hybridization reactions may comprise the hybridization of one or more capture probes to one or more nucleic acid molecules in a sample or subset of nucleic acid molecules. The hybridization reactions may comprise hybridizing one or more capture probe sets to one or more nucleic acid molecules in a sample or subset of nucleic acid molecules. The hybridization reactions may comprise one or more hybridization arrays, multiplex hybridization reactions, hybridization chain reactions, isothermal hybridization reactions, nucleic acid hybridization reactions, or a combination thereof. The one or more hybridization arrays may comprise hybridization array genotyping, hybridization array proportional sensing, DNA hybridization arrays, macroarrays, microarrays, high-density oligonucleotide arrays, genomic hybridization arrays, comparative hybridization arrays, or a combination thereof. The hybridization reaction may comprise one or more capture probes, one or more beads, one or more labels, one or more subsets of nucleic acid molecules, one or more nucleic acid samples, one or more reagents, one or more wash buffers, one or more elution buffers, one or more hybridization buffers, one or more hybridization chambers, one or more incubators, one or more separators, or a combination thereof.

The methods disclosed herein may comprise conducting one or more enrichment reactions on one or more nucleic acid molecules in a sample. The enrichment reactions may comprise contacting a sample with one or more beads or bead sets. The enrichment reaction may comprise differential amplification of two or more subsets of nucleic acid molecules based on one or more genome features. For example, the enrichment reaction comprises differential amplification of two or more subsets of nucleic acid molecules based on GC content. Alternatively, or additionally, the enrichment reaction comprises differential amplification of two or more subsets of nucleic acid molecules based on methylation state. The enrichment reactions may comprise one or more hybridization reactions. The enrichment reactions may further comprise isolation and/or purification of one or more hybridized nucleic acid molecules, one or more bead bound nucleic acid molecules, one or more free nucleic acid molecules (e.g., capture probe free nucleic acid molecules, bead free nucleic acid molecules), one or more labeled nucleic acid molecules, one or more non-labeled nucleic acid molecules, one or more amplicons, one or more non-amplified nucleic acid molecules, or a combination thereof. Alternatively, or additionally, the enrichment reaction may comprise enriching for one or more cell types in the sample. The one or more cell types may be enriched by flow cytometry.

The one or more enrichment reactions may produce one or more enriched nucleic acid molecules. The enriched nucleic acid molecules may comprise a nucleic acid molecule or variant or derivative thereof. For example, the enriched nucleic acid molecules comprise one or more hybridized nucleic acid molecules, one or more bead bound nucleic acid molecules, one or more free nucleic acid molecules (e.g., capture probe free nucleic acid molecules, bead free nucleic acid molecules), one or more labeled nucleic acid molecules, one or more non-labeled nucleic acid molecules, one or more amplicons, one or more non-amplified nucleic acid molecules, or a combination thereof. The enriched nucleic acid molecules may be differentiated from non-enriched nucleic acid molecules by GC content, molecular size, genomes, genome features, or a combination thereof. The enriched nucleic acid molecules may be derived from one or more assays, supernatants, eluants, or a combination thereof. The enriched nucleic acid molecules may differ from the non-enriched nucleic acid molecules by mean size, mean GC content, genomes, or a combination thereof. In some cases, an enrichment may comprise multiple subsets of DNA enriched for different genomic regions, undergoing independent processing operations prior to being combined for a sequencing assay, FIG. 15. In some cases, an enrichment may comprise multiple subsets of DNA enriched for different genomic regions, undergoing independent processing operations prior to being independently sequenced and analyzed, FIG. 16.

The methods disclosed herein may comprise conducting one or more isolation or purification reactions on one or more nucleic acid molecules in a sample. The isolation or purification reactions may comprise contacting a sample with one or more beads or bead sets. The isolation or purification reaction may comprise one or more hybridization reactions, enrichment reactions, amplification reactions, sequencing reactions, or a combination thereof. The isolation or purification reaction may comprise the use of one or more separators. The one or more separators may comprise a magnetic separator. The isolation or purification reaction may comprise separating bead bound nucleic acid molecules from bead free nucleic acid molecules. The isolation or purification reaction may comprise separating capture probe hybridized nucleic acid molecules from capture probe free nucleic acid molecules. The isolation or purification reaction may comprise separating a first subset of nucleic acid molecules from a second subset of nucleic acid molecules, wherein the first subset of nucleic acid molecules differ from the second subset on nucleic acid molecules by mean size, mean GC content, genomes, or a combination thereof.

The methods disclosed herein may comprise conducting one or more elution reactions on one or more nucleic acid molecules in a sample. The elution reactions may comprise contacting a sample with one or more beads or bead sets. The elution reaction may comprise separating bead bound nucleic acid molecules from bead free nucleic acid molecules. The elution reaction may comprise separating capture probe hybridized nucleic acid molecules from capture probe free nucleic acid molecules. The elution reaction may comprise separating a first subset of nucleic acid molecules from a second subset of nucleic acid molecules, wherein the first subset of nucleic acid molecules differ from the second subset on nucleic acid molecules by mean size, mean GC content, genomes, or a combination thereof.

The methods disclosed herein may comprise one or more fragmentation reactions. The fragmentation reactions may comprise fragmenting one or more nucleic acid molecules in a sample or subset of nucleic acid molecules to produce one or more fragmented nucleic acid molecules. The one or more nucleic acid molecules may be fragmented by sonication, needle shear, nebulisation, shearing (e.g., acoustic shearing, mechanical shearing, point-sink shearing), passage through a French pressure cell, or enzymatic digestion. Enzymatic digestion may occur by nuclease digestion (e.g., micrococcal nuclease digestion, endonucleases, exonucleases, RNAse H or DNase I). Fragmentation of the one or more nucleic acid molecules may result in fragment sized of about 100 base pairs to about 2000 base pairs, about 200 base pairs to about 1500 base pairs, about 200 base pairs to about 1000 base pairs, about 200 base pairs to about 500 base pairs, about 500 base pairs to about 1500 base pairs, and about 500 base pairs to about 1000 base pairs. The one or more fragmentation reactions may result in fragment sized of about 50 base pairs to about 1000 base pairs. The one or more fragmentation reactions may result in fragment sized of about 100 base pairs, 150 base pairs, 200 base pairs, 250 base pairs, 300 base pairs, 350 base pairs, 400 base pairs, 450 base pairs, 500 base pairs, 550 base pairs, 600 base pairs, 650 base pairs, 700 base pairs, 750 base pairs, 800 base pairs, 850 base pairs, 900 base pairs, 950 base pairs, 1000 base pairs or more.

Fragmenting the one or more nucleic acid molecules may comprise mechanical shearing of the one or more nucleic acid molecules in the sample for a period of time. The fragmentation reaction may occur for at least about 10, 15, 20, 25, 30, 35, 40, 45, 50, 55, 60, 65, 70, 75, 80, 85, 90, 95, 100, 125, 150, 175, 200, 225, 250, 275, 300, 325, 350, 375, 400, 425, 450, 475, 500 or more seconds.

Fragmenting the one or more nucleic acid molecules may comprise contacting a nucleic acid sample with one or more beads. Fragmenting the one or more nucleic acid molecules may comprise contacting the nucleic acid sample with a plurality of beads, wherein the ratio of the volume of the plurality of beads to the volume of nucleic acid sample is about 0.10, 0.20, 0.30, 0.40, 0.50, 0.60, 0.70, 0.80, 0.90, 1.00, 1.10, 1.20, 1.30, 1.40, 1.50, 1.60, 1.70, 1.80, 1.90, 2.00 or more. Fragmenting the one or more nucleic acid molecules may comprise contacting the nucleic acid sample with a plurality of beads, wherein the ratio of the volume of the plurality of beads to the volume of nucleic acid is about 2.00, 1.90, 1.80, 1.70, 1.60, 1.50, 1.40, 1.30, 1.20, 1.10, 1.00, 0.90, 0.80, 0.70, 0.60, 0.50, 0.40, 0.30, 0.20, 0.10, 0.05, 0.04, 0.03, 0.02, 0.01 or less.

The methods disclosed herein may comprise conducting one or more detection reactions on one or more nucleic acid molecules in a sample. Detection reactions may comprise one or more sequencing reactions. Alternatively, conducting a detection reaction comprises optical sensing, electrical sensing, or a combination thereof. Optical sensing may comprise optical sensing of a photoilluminscence photon emission, fluorescence photon emission, pyrophosphate photon emission, chemiluminescence photon emission, or a combination thereof. Electrical sensing may comprise electrical sensing of an ion concentration, ion current modulation, nucleotide electrical field, nucleotide tunneling current, or a combination thereof.

The methods disclosed herein may comprise conducting one or more quantification reactions on one or more nucleic acid molecules in a sample. Quantification reactions may comprise sequencing, PCR, qPCR, digital PCR, or a combination thereof.

The methods disclosed herein may comprise one or more samples. The methods disclosed herein may comprise 1, 2, 3, 4, 5, 6, 7, 8, 9, 10, 11, 12, 13, 14, 15, 20, 25, 30, 35, 40, 45, 50, 55, 60, 65, 70, 75, 80, 85, 90, 95, 100 or more samples. The sample may be derived from a subject. The two or more samples may be derived from a single subject. The two or more samples may be derived from t2, 3, 4, 5, 6, 7, 8, 9, 10, 11, 12, 13, 14, 15, 20, 25, 30, 35, 40, 45, 50, 55, 60, 65, 70, 75, 80, 85, 90, 95, 100 or more different subjects. The subject may be a mammal, reptiles, amphibians, avians, and fish. The mammal may be a human, ape, orangutan, monkey, chimpanzee, cow, pig, horse, rodent, dog, cat, or other animal. A reptile may be a lizard, snake, alligator, turtle, crocodile, and tortoise. An amphibian may be a toad, frog, newt, and salamander. Examples of avians include, but are not limited to, ducks, geese, penguins, ostriches, and owls. Examples of fish include, but are not limited to, catfish, eels, sharks, and swordfish. The subject may be a human. The subject may suffer from a disease or condition.

The two or more samples may be collected over 1, 2, 3, 4, 5, 6, 7, 8, 9, 10, 11, 12, 15, 20, 30, 40, 50, 60, 70, 80, 90, 100, 200, 300, 400, 500, 600, 700, 800, 900, 1000 or time points. The time points may occur over a 1, 2, 3, 4, 5, 6, 7, 8, 9, 10, 11, 12, 13, 14, 15, 16, 17, 18, 19, 20, 21, 22, 23, 24, 25, 30, 35, 40, 45, 50, 55, 60 or more hour period. The time points may occur over a 1, 2, 3, 4, 5, 6, 7, 8, 9, 10, 11, 12, 13, 14, 15, 16, 17, 18, 19, 20, 21, 22, 23, 24, 25, 30, 35, 40, 45, 50, 55, 60 or more day period. The time points may occur over a 1, 2, 3, 4, 5, 6, 7, 8, 9, 10, 11, 12, 13, 14, 15, 16, 17, 18, 19, 20, 21, 22, 23, 24, 25, 30, 35, 40, 45, 50, 55, 60 or more week period. The time points may occur over a 1, 2, 3, 4, 5, 6, 7, 8, 9, 10, 11, 12, 13, 14, 15, 16, 17, 18, 19, 20, 21, 22, 23, 24, 25, 30, 35, 40, 45, 50, 55, 60 or more month period. The time points may occur over a 1, 2, 3, 4, 5, 6, 7, 8, 9, 10, 11, 12, 13, 14, 15, 16, 17, 18, 19, 20, 21, 22, 23, 24, 25, 30, 35, 40, 45, 50, 55, 60 or more year period.

In some cases, a method can comprise obtaining a biological sample from a subject. A subject can be human or non-human. A subject can be an adult or a child. In some cases, an adult subject can be 18 or over 18 years of age. In some cases, a biological sample of a subject can be derived from a tumor biopsy, whole blood, or blood plasma. In some cases, a biological sample may be from a body fluid, cell, skin, tissue, organ, or combination thereof. The sample may be a blood, plasma, a blood fraction, saliva, sputum, urine, semen, transvaginal fluid, cerebrospinal fluid, stool, a cell or a tissue biopsy. The sample may be from an adrenal gland, appendix, bladder, brain, ear, esophagus, eye, gall bladder, heart, kidney, large intestine, liver, lung, mouth, muscle, nose, pancreas, parathyroid gland, pineal gland, pituitary gland, skin, small intestine, spleen, stomach, thymus, thyroid gland, trachea, uterus, vermiform appendix, cornea, skin, heart valve, artery, or vein The samples may comprise one or more nucleic acid molecules. The nucleic acid molecule may be a DNA molecule, RNA molecule (e.g. mRNA, cRNA or miRNA), and DNA/RNA hybrids. Examples of DNA molecules include, but are not limited to, double-stranded DNA, single-stranded DNA, single-stranded DNA hairpins, cDNA, genomic DNA. The nucleic acid may be an RNA molecule, such as a double-stranded RNA, single-stranded RNA, ncRNA, RNA hairpin, and mRNA. Examples of ncRNA include, but are not limited to, siRNA, miRNA, snoRNA, piRNA, tiRNA, PASR, TASR, aTASR, TSSa-RNA, snRNA, RE-RNA, uaRNA, x-ncRNA, hY RNA, usRNA, snaR, and vtRNA.

The methods disclosed herein may comprise one or more containers. The methods disclosed herein may comprise 1 or more, 2 or more, 3 or more, 4 or more, 5 or more, 6 or more, 7 or more, 8 or more, 9 or more, 10 or more, 20 or more, 30 or more, 40 or more, 50 or more, 60 or more, 70 or more, 80 or more, 90 or more, 100 or more, 125 or more, 150 or more, 175 or more, 200 or more, 250 or more, 300 or more, 350 or more, 400 or more, 500 or more, 600 or more, 700 or more, 800 or more, 900 or more, or 1000 or more containers. The one or more containers may be different, similar, identical, or a combination thereof. Examples of containers include, but are not limited to, plates, microplates, PCR plates, wells, microwells, tubes, Eppendorf tubes, vials, arrays, microarrays, and chips.

The methods disclosed herein may comprise one or more reagents. The methods disclosed herein may comprise 1 or more, 2 or more, 3 or more, 4 or more, 5 or more, 6 or more, 7 or more, 8 or more, 9 or more, 10 or more, 20 or more, 30 or more, 40 or more, 50 or more, 60 or more, 70 or more, 80 or more, 90 or more, 100 or more, 125 or more, 150 or more, 175 or more, 200 or more, 250 or more, 300 or more, 350 or more, 400 or more, 500 or more, 600 or more, 700 or more, 800 or more, 900 or more, or 1000 or more reagents. The one or more reagents may be different, similar, identical, or a combination thereof. The reagents may improve the efficiency of the one or more assays. Reagents may improve the stability of the nucleic acid molecule or variant or derivative thereof. Reagents may include, but are not limited to, enzymes, proteases, nucleases, molecules, polymerases, reverse transcriptases, ligases, and chemical compounds. The methods disclosed herein may comprise conducting an assay comprising one or more antioxidants. Generally, antioxidants are molecules that inhibit oxidation of another molecule. Examples of antioxidants include, but are not limited to, ascorbic acid (e.g., vitamin C), glutathione, lipoic acid, uric acid, carotenes, α-tocopherol (e.g., vitamin E), ubiquinol (e.g., coenzyme Q), and vitamin A.

The methods disclosed herein may comprise one or more buffers or solutions. The methods disclosed herein may comprise 1 or more, 2 or more, 3 or more, 4 or more, 5 or more, 6 or more, 7 or more, 8 or more, 9 or more, 10 or more, 20 or more, 30 or more, 40 or more, 50 or more, 60 or more, 70 or more, 80 or more, 90 or more, 100 or more, 125 or more, 150 or more, 175 or more, 200 or more, 250 or more, 300 or more, 350 or more, 400 or more, 500 or more, 600 or more, 700 or more, 800 or more, 900 or more, or 1000 or more buffers or solutions. The one or more buffers or solutions may be different, similar, identical, or a combination thereof. The buffers or solutions may improve the efficiency of the one or more assays. Buffers or solutions may improve the stability of the nucleic acid molecule or variant or derivative thereof. Buffers or solutions may include, but are not limited to, wash buffers, elution buffers, and hybridization buffers.

The methods disclosed herein may comprise one or more beads, a plurality of beads, or one or more bead sets. The methods disclosed herein may comprise 1 or more, 2 or more, 3 or more, 4 or more, 5 or more, 6 or more, 7 or more, 8 or more, 9 or more, 10 or more, 20 or more, 30 or more, 40 or more, 50 or more, 60 or more, 70 or more, 80 or more, 90 or more, 100 or more, 125 or more, 150 or more, 175 or more, 200 or more, 250 or more, 300 or more, 350 or more, 400 or more, 500 or more, 600 or more, 700 or more, 800 or more, 900 or more, or 1000 or more one or more beads or bead sets. The one or more beads or bead sets may be different, similar, identical, or a combination thereof. The beads may be magnetic, antibody coated, protein A crosslinked, protein G crosslinked, streptavidin coated, oligonucleotide conjugated, silica coated, or a combination thereof. Examples of beads include, but are not limited to, Ampure beads, AMPure XP beads, streptavidin beads, agarose beads, magnetic beads, Dynabeads®, MACS® microbeads, antibody conjugated beads (e.g., anti-immunoglobulin microbead), protein A conjugated beads, protein G conjugated beads, protein A/G conjugated beads, protein L conjugated beads, oligo-dT conjugated beads, silica beads, silica-like beads, anti-biotin microbead, anti-fluorochrome microbead, and BcMag™ Carboxy-Terminated Magnetic Beads. In some aspects of the disclosure, the one or more beads comprise one or more Ampure beads. Alternatively, or additionally, the one or more beads comprise AMPure XP beads.

The methods disclosed herein may comprise one or more primers, a plurality of primers, or one or more primer sets. The primers may further comprise one or more linkers. The primers may further comprise one or more labels. The primers may be used in one or more assays. For example, the primers are used in one or more sequencing reactions, amplification reactions, or a combination thereof. The methods disclosed herein may comprise 1 or more, 2 or more, 3 or more, 4 or more, 5 or more, 6 or more, 7 or more, 8 or more, 9 or more, 10 or more, 20 or more, 30 or more, 40 or more, 50 or more, 60 or more, 70 or more, 80 or more, 90 or more, 100 or more, 125 or more, 150 or more, 175 or more, 200 or more, 250 or more, 300 or more, 350 or more, 400 or more, 500 or more, 600 or more, 700 or more, 800 or more, 900 or more, or 1000 or more one or more primers or primer sets. The primers may comprise about 100 nucleotides. The primers may comprise between about 10 to about 500 nucleotides, between about 20 to about 450 nucleotides, between about 30 to about 400 nucleotides, between about 40 to about 350 nucleotides, between about 50 to about 300 nucleotides, between about 60 to about 250 nucleotides, between about 70 to about 200 nucleotides, or between about 80 to about 150 nucleotides. In some aspects of the disclosure, the primers comprise between about 80 nucleotides to about 100 nucleotides. The one or more primers or primer sets may be different, similar, identical, or a combination thereof.

The primers may hybridize to at least a portion of the one or more nucleic acid molecules or variant or derivative thereof in the sample or subset of nucleic acid molecules. The primers may hybridize to one or more genomes. The primers may hybridize to different, similar, and/or identical genomes. The one or more primers may be at least about 50%, 55%, 60%, 65%, 70%, 75%, 80%, 85%, 90%, 95%, 97%, 99% or more complementary to the one or more nucleic acid molecules or variant or derivative thereof.

The primers may comprise one or more nucleotides. The primers may comprise 1 or more, 2 or more, 3 or more, 4 or more, 5 or more, 6 or more, 7 or more, 8 or more, 9 or more, 10 or more, 20 or more, 30 or more, 40 or more, 50 or more, 60 or more, 70 or more, 80 or more, 90 or more, 100 or more, 125 or more, 150 or more, 175 or more, 200 or more, 250 or more, 300 or more, 350 or more, 400 or more, 500 or more, 600 or more, 700 or more, 800 or more, 900 or more, or 1000 or more nucleotides. The primers may comprise about 100 nucleotides. The primers may comprise between about 10 to about 500 nucleotides, between about 20 to about 450 nucleotides, between about 30 to about 400 nucleotides, between about 40 to about 350 nucleotides, between about 50 to about 300 nucleotides, between about 60 to about 250 nucleotides, between about 70 to about 200 nucleotides, or between about 80 to about 150 nucleotides. In some aspects of the disclosure, the primers comprise between about 80 nucleotides to about 100 nucleotides.

The plurality of primers or the primer sets may comprise two or more primers with identical, similar, and/or different sequences, linkers, and/or labels. For example, two or more primers comprise identical sequences. In another example, two or more primers comprise similar sequences. In yet another example, two or more primers comprise different sequences. The two or more primers may further comprise one or more linkers. The two or more primers may further comprise different linkers. The two or more primers may further comprise similar linkers. The two or more primers may further comprise identical linkers. The two or more primers may further comprise one or more labels. The two or more primers may further comprise different labels. The two or more primers may further comprise similar labels. The two or more primers may further comprise identical labels.

In some cases, a universal primers can be utilized and can comprise one or more of: an 8F primer, a 27F primer, a CC[F] primer, a 357F primer, a 515F primer, a 533F primer, a 16S.1100.F16 primer, a 1237F primer, a 519R primer, a CD[R] primer, a 907R primer, a 1391R primer, a 1492R(I) primer, a 1492R(s) primer, a U1492R primer, a 928F primer, a 336R primer, an 1100F primer, an 1100R primer, a 337F primer, a 785F primer, an 805R primer, a 518R primer, and any other suitable universal primer. Alternatively, for samples in which specific primers may be appropriate, amplification can be performed with specific primers. In examples, specific primers can include: a CYA106 primer (for cyanobacteria), a CYA359F primer (for cyanobacteria), an 895F primer (for bacteria excluding plastids and cyanobacteria), a CYA781R primer (for cyanobacteria), a 902R primer (for bacteria excluding plastids and cyanobacteria), a 904R primer (for bacteria excluding plastids and cyanobacteria), an 1100R primer (for bacteria), an 1185mR primer (for bacteria excluding plastids and cyanobacteria), an 1185aR primer (for lichen-associated Rhizobiales), a 1381R primer (for bacteria excluding Asterochloris species plastids), or any other suitable specific primer.

The capture probes, primers, labels, and/or beads may comprise one or more nucleotides. The one or more nucleotides may comprise RNA, DNA, a mix of DNA and RNA residues or their modified analogs such as 2'-OMe, or 2'-fluoro (2'-F), locked nucleic acid (LNA), or abasic sites.

The methods disclosed herein may comprise one or more labels. The methods disclosed herein may comprise 1 or more, 2 or more, 3 or more, 4 or more, 5 or more, 6 or more, 7 or more, 8 or more, 9 or more, 10 or more, 20 or more, 30 or more, 40 or more, 50 or more, 60 or more, 70 or more, 80 or more, 90 or more, 100 or more, 125 or more, 150 or more, 175 or more, 200 or more, 250 or more, 300 or more, 350 or more, 400 or more, 500 or more, 600 or more, 700 or more, 800 or more, 900 or more, or 1000 or more one or more labels. The one or more labels may be different, similar, identical, or a combination thereof.

Examples of labels include, but are not limited to, chemical, biochemical, biological, colorimetric, enzymatic, fluorescent, and luminescent labels. The label comprise a dye, a photocrosslinker, a cytotoxic compound, a drug, an affinity label, a photoaffinity label, a reactive compound, an antibody or antibody fragment, a biomaterial, a nanoparticle, a spin label, a fluorophore, a metal-containing moiety, a radioactive moiety, a novel functional group, a group that covalently or noncovalently interacts with other molecules, a photocaged moiety, an actinic radiation excitable moiety, a ligand, a photoisomerizable moiety, biotin, a biotin analogue, a moiety incorporating a heavy atom, a chemically cleavable group, a photocleavable group, a redox-active agent, an isotopically labeled moiety, a biophysical probe, a phosphorescent group, a chemiluminescent group, an electron dense group, a magnetic group, an intercalating group, a chromophore, an energy transfer agent, a biologically active agent, a detectable label, or a combination thereof.

The label may be a chemical label. Examples of chemical labels can include, but are not limited to, biotin and radioisotopes (e.g., iodine, carbon, phosphate, hydrogen).

The methods, kits, and compositions disclosed herein may comprise a biological label. The biological labels may comprise metabolic labels, including, but not limited to, bioorthogonal azide-modified amino acids, sugars, and other compounds.

The methods, kits, and compositions disclosed herein may comprise an enzymatic label. Enzymatic labels can include, but are not limited to horseradish peroxidase (HRP), alkaline phosphatase (AP), glucose oxidase, and β-galactosidase. The enzymatic label may be luciferase.

The methods, kits, and compositions disclosed herein may comprise a fluorescent label. The fluorescent label may be an organic dye (e.g., FITC), biological fluorophore (e.g., green fluorescent protein), or quantum dot. A non-limiting list of fluorescent labels includes fluorescein isothicyante (FITC), DyLight Fluors, fluorescein, rhodamine (tetramethyl rhodamine isothiocyanate, TRITC), coumarin, Lucifer Yellow, and BODIPY. The label may be a fluorophore. Examples of fluorophores include, but are not limited to, indocarbocyanine (C3), indodicarbocyanine (C5), Cy3, Cy3.5, Cy5, Cy5.5, Cy7, Texas Red, Pacific Blue, Oregon Green 488, Alexa Fluor®-355, Alexa Fluor 488, Alexa Fluor 532, Alexa Fluor 546, Alexa Fluor-555, Alexa Fluor 568, Alexa Fluor 594, Alexa Fluor 647, Alexa Fluor 660, Alexa Fluor 680, JOE, Lissamine, Rhodamine Green, BODIPY, fluorescein isothiocyanate (FITC), carboxy-fluorescein (FAM), phycoerythrin, rhodamine, dichlororhodamine (dRhodamine), carboxy tetramethylrhodamine (TAMRA), carboxy-X-rhodamine (ROX™), LIZ™, VIC™ NED™ PET™, SYBR, PicoGreen, RiboGreen, and the like. The fluorescent label may be a green fluorescent protein (GFP), red fluorescent protein (RFP), yellow fluorescent protein, phycobiliproteins (e.g., allophycocyanin, phycocyanin, phycoerythrin, and phycoerythrocyanin).

The methods disclosed herein may comprise one or more linkers. The methods disclosed herein may comprise 1 or more, 2 or more, 3 or more, 4 or more, 5 or more, 6 or more, 7 or more, 8 or more, 9 or more, 10 or more, 20 or more, 30 or more, 40 or more, 50 or more, 60 or more, 70 or more, 80 or more, 90 or more, 100 or more, 125 or more, 150 or more, 175 or more, 200 or more, 250 or more, 300 or more, 350 or more, 400 or more, 500 or more, 600 or more, 700 or more, 800 or more, 900 or more, or 1000 or more one or more linkers. The one or more linkers may be different, similar, identical, or a combination thereof.

Suitable linkers comprise any chemical or biological compound capable of attaching to a label, primer, and/or capture probe disclosed herein. If the linker attaches to both the label and the primer or capture probe, then a suitable linker may be capable of sufficiently separating the label and the primer or capture probe. Suitable linkers may not significantly interfere with the ability of the primer and/or capture probe to hybridize to a nucleic acid molecule, portion thereof, or variant or derivative thereof. Suitable linkers may not significantly interfere with the ability of the label to be detected. The linker may be rigid. The linker may be flexible. The linker may be semi rigid. The linker may be proteolytically stable (e.g., resistant to proteolytic cleavage). The linker may be proteolytically unstable (e.g., sensitive to proteolytic cleavage). The linker may be helical. The linker may be non-helical. The linker may be coiled. The linker may be β-stranded. The linker may comprise a turn conformation. The linker may be a single chain. The linker may be a long chain. The linker may be a short chain. The linker may comprise at least about 5 residues, at least about 10 residues, at least about 15 residues, at least about 20 residues, at least about 25 residues, at least about 30 residues, or at least about 40 residues or more.

Examples of linkers include, but are not limited to, hydrazone, disulfide, thioether, and peptide linkers. The linker may be a peptide linker. The peptide linker may comprise a proline residue. The peptide linker may comprise an arginine, phenylalanine, threonine, glutamine, glutamate, or any combination thereof. The linker may be a heterobifunctional crosslinker.

The methods disclosed herein may comprise conducting 1 or more, 2 or more, 3 or more, 4 or more, 5 or more, 6 or more, 7 or more, 8 or more, 9 or more, 10 or more, 11 or more, 12 or more, 13 or more, 14 or more, 15 or more, 20 or more, 25 or more, 30 or more, 35 or more, 40 or more, 45 or more, or 50 or more assays on a sample comprising one or more nucleic acid molecules. The two or more assays may be different, similar, identical, or a combination thereof. For example, the methods disclosed herein comprise conducting two or more sequencing reactions. In another example, the methods disclosed herein comprise conducting two or more assays, wherein at least one of the two or more assays comprises a sequencing reaction. In yet another example, the methods disclosed herein comprise conducting two or more assays, wherein at least two of the two or more assays comprises a sequencing reaction and a hybridization reaction. The two or more assays may be performed sequentially, simultaneously, or a combination thereof. For example, the two or more sequencing reactions may be performed simultaneously. In another example, the methods disclosed herein comprise conducting a hybridization reaction, followed by a sequencing reaction. In yet another example, the methods disclosed herein comprise conducting two or more hybridization reactions simultaneously, followed by conducting two or more sequencing reactions simultaneously. The two or more assays may be performed by one or more devices. For example, two or more amplification reactions may be performed by a PCR machine. In another example, two or more sequencing reactions may be performed by two or more sequencers.

The methods disclosed herein may comprise one or more devices. The methods disclosed herein may comprise one or more assays comprising one or more devices. The methods disclosed herein may comprise the use of one or more devices to perform one or more operations or assays. The methods disclosed herein may comprise the use of one or more devices in one or more operations or assays. For example, conducting a sequencing reaction may comprise one or more sequencers. In another example, producing a subset of nucleic acid molecules may comprise the use of one or more magnetic separators. In yet another example, one or more processors may be used in the analysis of one or more nucleic acid samples. Examples of devices include, but are not limited to, sequencers, thermocyclers, real-time PCR instruments, magnetic separators, transmission devices, hybridization chambers, electrophoresis apparatus, centrifuges, microscopes, imagers, fluorimeters, luminometers, plate readers, computers, processors, and bioanalyzers.

The methods disclosed herein may comprise one or more sequencers. The one or more sequencers may comprise one or more HiSeq, MiSeq, HiScan, Genome Analyzer IIx, SOLiD Sequencer, Ion Torrent PGM, 454 GS Junior, Pac Bio RS, or a combination thereof. The one or more sequencers may comprise one or more sequencing platforms. The one or more sequencing platforms may comprise GS FLX by 454 Life Technologies/Roche, Genome Analyzer by Solexa/Illumina, SOLiD by Applied Biosystems, CGA Platform by Complete Genomics, PacBio RS by Pacific Biosciences, or a combination thereof.

The methods disclosed herein may comprise one or more thermocyclers. The one or more thermocyclers may be used to amplify one or more nucleic acid molecules. The methods disclosed herein may comprise one or more real-time PCR instruments. The one or more real-time PCR instruments may comprise a thermal cycler and a fluorimeter. The one or more thermocyclers may be used to amplify and detect one or more nucleic acid molecules.

The methods disclosed herein may comprise one or more magnetic separators. The one or more magnetic separators may be used for separation of paramagnetic and ferromagnetic particles from a suspension. The one or more magnetic separators may comprise one or more LifeStep™ biomagnetic separators, SPHERO™ FlexiMag separator, SPHERO™ MicroMag separator, SPHERO™ HandiMag separator, SPHERO™ MiniTube Mag separator, SPHERO™ UltraMag separator, DynaMag™ magnet, DynaMag™-2 Magnet, or a combination thereof.

The methods disclosed herein may comprise one or more bioanalyzers. In some cases, a bioanalyzer is a chip-based capillary electrophoresis machine that can analyze RNA, DNA, and proteins. The one or more bioanalyzers may comprise Agilent's 2100 bioanalyzer.

Figure 14:
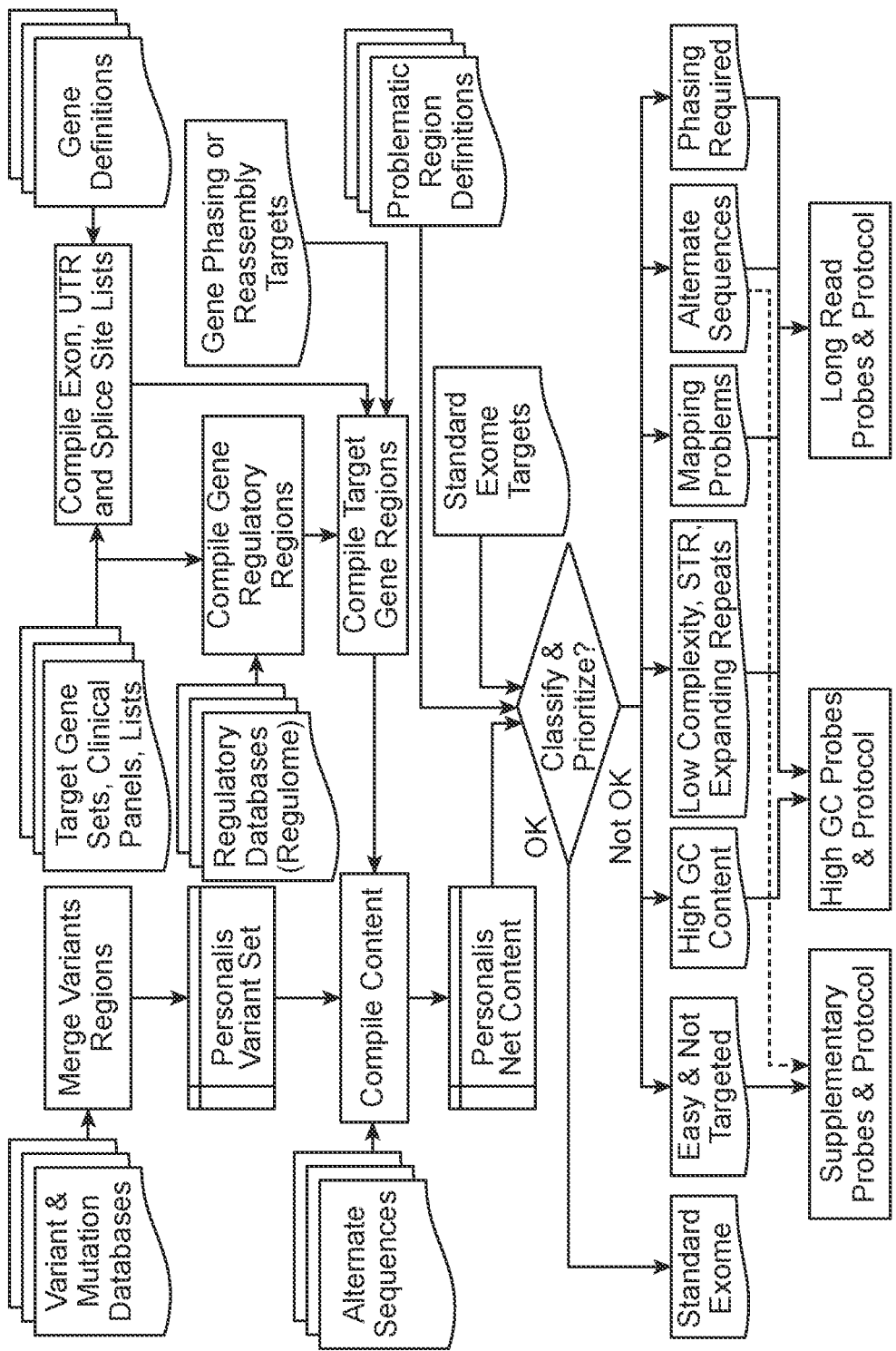
FIG. 14 shows a method for developing multithreaded assay addressing multiple biomedical applications.
Figure 15:
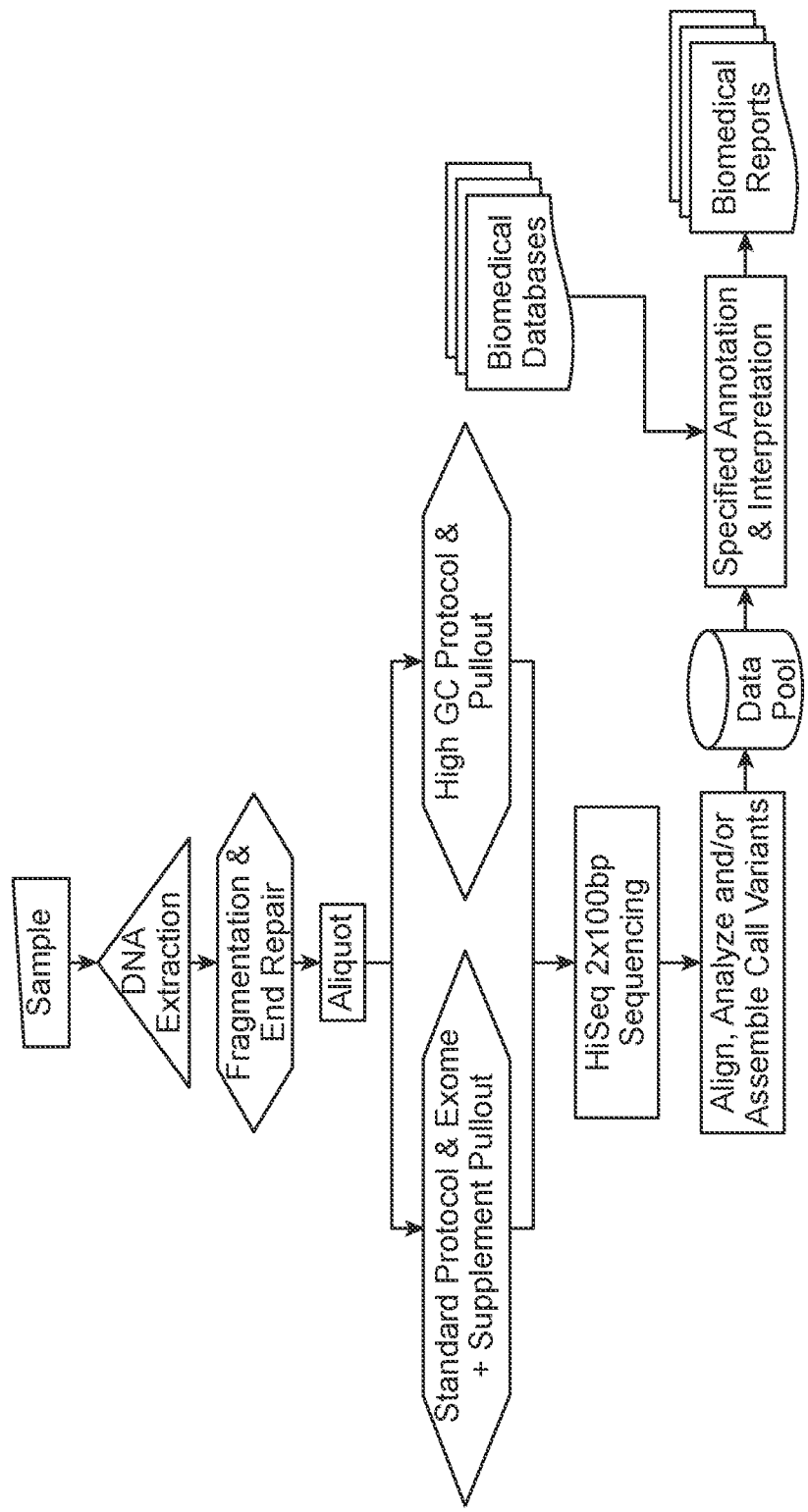
FIG. 15 depicts an example of an assay workflow comprising multiple subsets of DNA enriched for different genomic regions, undergoing some independent processing operations prior to being combined for a sequencing assay. Reads from the two or more subsets are combined either a) in the sequencing device b) subsequently in silico (e.g., using one or more algorithms) to produce a single test result for the regions addressed by the union of the two or more subsets and resulting in a data pool that may be used for one or more biomedical reports. A supplement pullout may include human target sequences and non-human target sequences.
Figure 16:
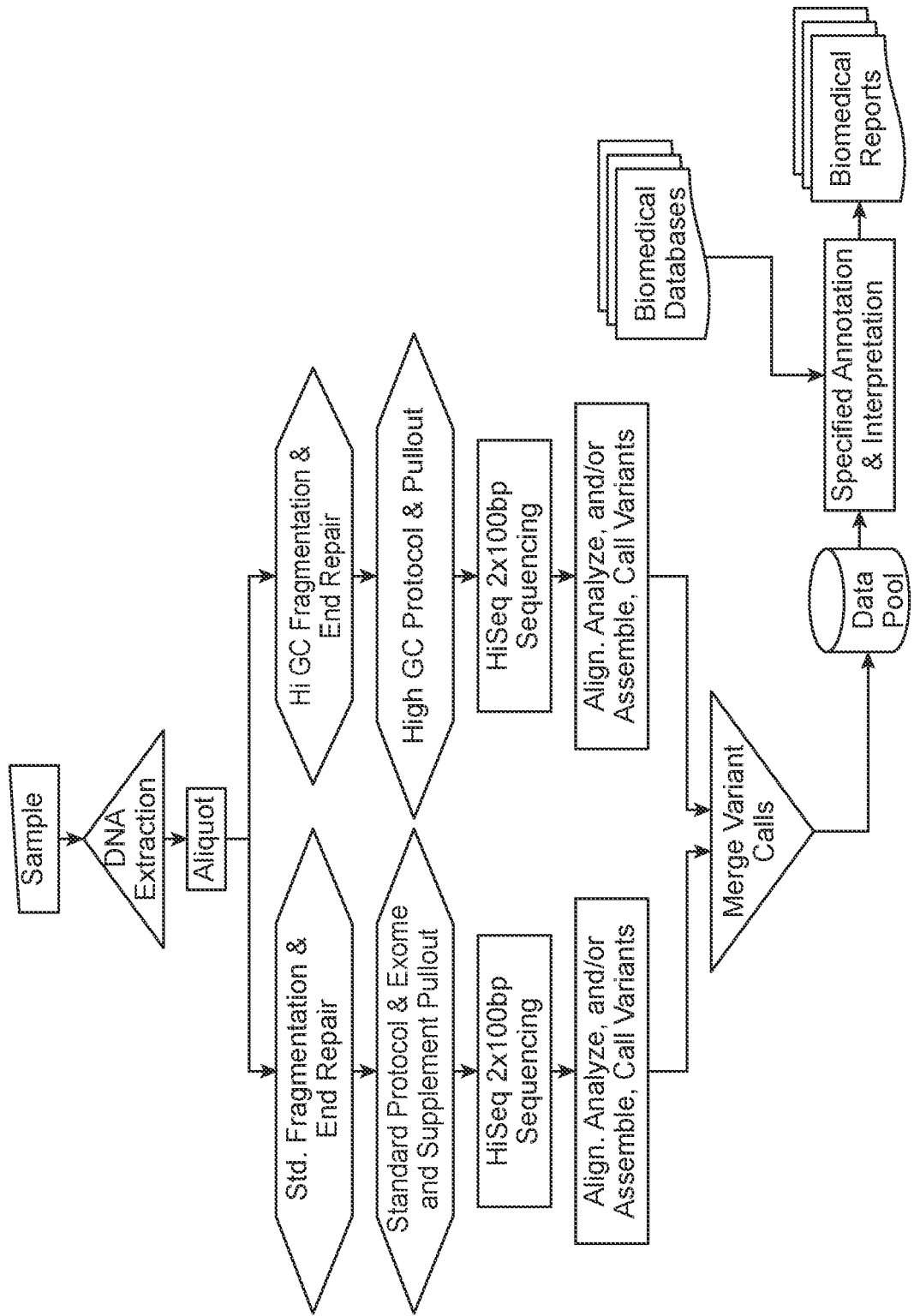
FIG. 16 depicts an example of an assay workflow comprising multiple subsets of DNA enriched for different genomic regions, undergoing some independent processing operations prior to being independently sequenced and analyzed for variants. Variants from the two subsets may be merged to produce a result for the regions addressed by the union of the two or more subsets and resulting in a data pool that may be used for one or more biomedical reports. A supplement pullout may include human target sequences and non-human target sequences.
Figure 17:
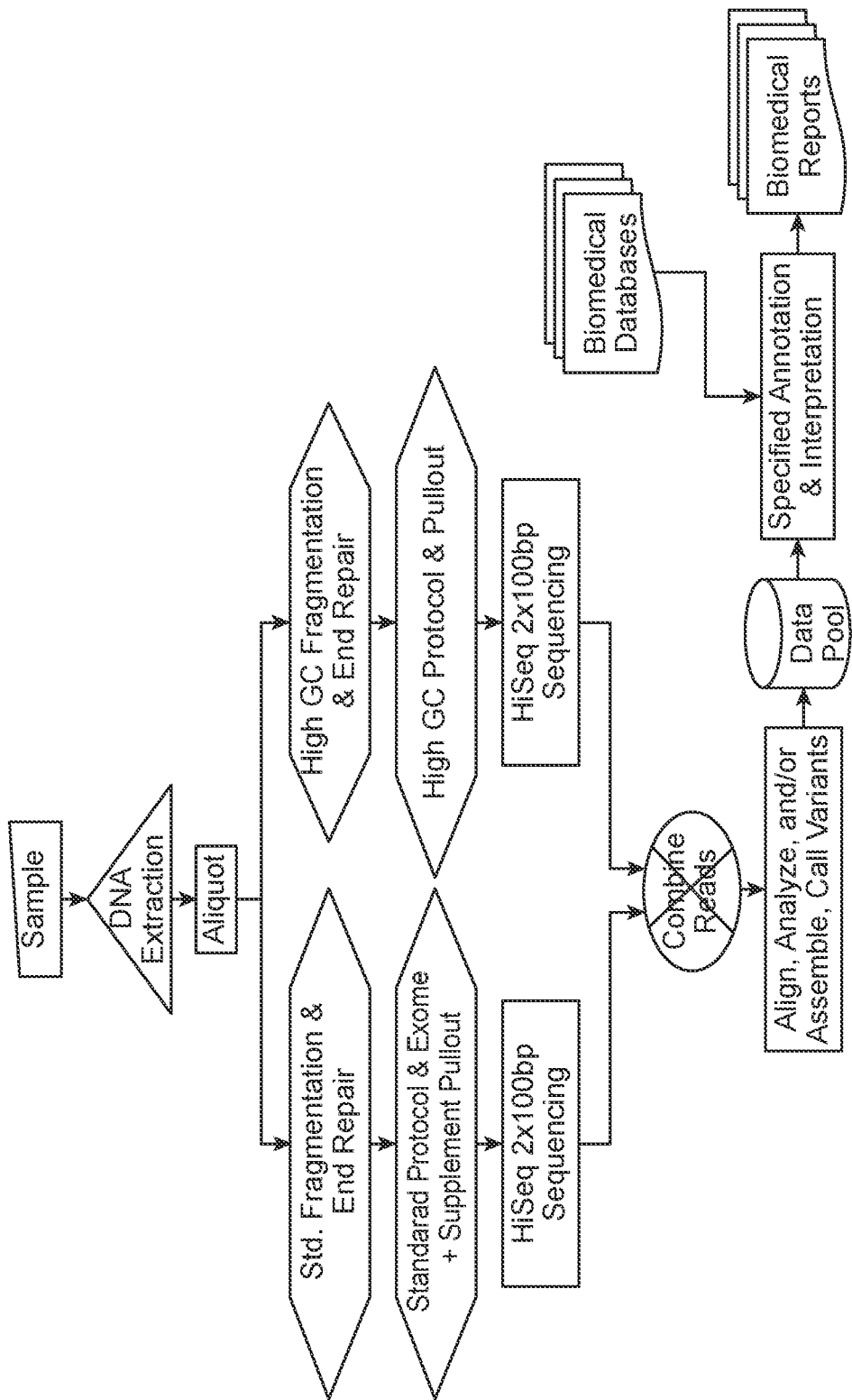
FIG. 17 depicts an example of an assay workflow comprising multiple subsets of DNA enriched for different genomic regions, undergoing some independent processing operations prior to being independently sequenced and producing primary data which may include sequence reads. Primary data from the two or more assays may be combined and analyzed (e.g., by one or more software programs or algorithms) to produce a result for all of the regions addressed by the union of the two or more subsets resulting in a data pool that may be used for one or more biomedical reports. A supplement pullout may include human target sequences and non-human target sequences.

The methods disclosed herein may comprise one or more processors. The one or more processors may analyze, compile, store, sort, combine, assess or otherwise process one or more data and/or results from one or more assays, one or more data and/or results based on or derived from one or more assays, one or more outputs from one or more assays, one or more outputs based on or derived from one or more assays, one or more outputs from one or data and/or results, one or more outputs based on or derived from one or more data and/or results, or a combination thereof. In some cases, a method disclosed herein can comprise combining data for analysis, as shown in FIG. 17. The one or more processors may transmit the one or more data, results, or outputs from one or more assays, one or more data, results, or outputs based on or derived from one or more assays, one or more outputs from one or more data or results, one or more outputs based on or derived from one or more data or results, or a combination thereof. The one or more processors may receive and/or store requests from a user. The one or more processors may produce or generate one or more data, results, outputs. The one or more processors may produce or generate one or more biomedical reports. The one or more processors may transmit one or more biomedical reports. The one or more processors may analyze, compile, store, sort, combine, assess or otherwise process information from one or more databases, one or more data or results, one or more outputs, or a combination thereof. The one or more processors may analyze, compile, store, sort, combine, assess or otherwise process information from 1, 2, 3, 4, 5, 6, 7, 8, 9, 10, 11, 12, 13, 14, 15, 16, 17, 18, 19, 20, 30 or more databases. The one or more processors may transmit one or more requests, data, results, outputs and/or information to one or more users, processors, computers, computer systems, memory locations, devices, databases, or a combination thereof. The one or more processors may receive one or more requests, data, results, outputs and/or information from one or more users, processors, computers, computer systems, memory locations, devices, databases or a combination thereof. The one or more processors may retrieve one or more requests, data, results, outputs and/or information from one or more users, processors, computers, computer systems, memory locations, devices, databases or a combination thereof. The present disclosure also provides a method that can be utilized for multiple biomedical applications. In some cases, variants, genes, reassembly genes, exons, UTRs, regulatory regions, splice sites, alternate sequences and other content of genome, human or non-human, interest can be combined from several databases to produce an aggregate set of content which is applicable to multiple biomedical reports. This content can then be categorized based on local or global genomic context, nucleotide content, sequencing performance and interpretation demands and then subsequently grouped into subsets for specialized protocol, assay development, and the like. In some cases, variants, genes, exons, UTRs, regulatory regions, splice sites, alternate sequences and other content of interest are combined from several databases to produce an aggregate set of content which is applicable to multiple biomedical reports. This content is then categorized based on local or global genomic context, nucleotide content, sequencing performance and interpretation demands and then subsequently grouped into subsets for specialized protocol and assay development, FIG. 14. In some cases, a protocol and/or assay may comprise a supplement pullout. A supplement pullout may comprise human target sequences, non-human target sequences, and a combination thereof. A supplement pullout may comprise a nucleic acid molecules from a subject (e.g., originating from cells derived from a tissue of the subject) and nucleic acid molecules that are not from the subject (e.g., from a microbe (commensal or parasitic), pathogen, or transplant). FIGS. 15-17 provide examples of assay workflows comprising a supplemental pullout for one or more of multiple subsets of DNA enriched for different genomic regions.

The methods disclosed herein may comprise one or more memory locations. The one or more memory locations may store information, data, results, outputs, requests, or a combination thereof. The one or more memory locations may receive information, data, results, outputs, requests, or a combination thereof from one or more users, processors, computers, computer systems, devices, or a combination thereof.

Methods described herein can be implemented with the aid of one or more computers and/or computer systems. A computer or computer system may comprise electronic storage locations (e.g., databases, memory) with machine-executable code for implementing the methods provided in the present disclosure, and one or more processors for executing the machine-executable code.

The methods disclosed herein may comprise treating and/or preventing a disease or condition in a subject based on one or more biomedical outputs. The one or more biomedical outputs may recommend one or more therapies. The one or more biomedical outputs may suggest, select, designate, recommend or otherwise determine a course of treatment and/or prevention of a disease or condition. The one or more biomedical outputs may recommend modifying or continuing one or more therapies. Modifying one or more therapies may comprise administering, initiating, reducing, increasing, and/or terminating one or more therapies. The one or more therapies comprise an anti-cancer, antiviral, antibacterial, antifungal, immunosuppressive therapy, or a combination thereof. The one or more therapies may treat, alleviate, or prevent one or more diseases or indications.

Examples of anti-cancer therapies include, but are not limited to, surgery, chemotherapy, radiation therapy, immunotherapy/biological therapy, photodynamic therapy. Anti-cancer therapies may comprise chemotherapeutics, monoclonal antibodies (e.g., rituximab, trastuzumab), cancer vaccines (e.g., therapeutic vaccines, prophylactic vaccines), gene therapy, or combination thereof.

The one or more therapies may comprise an antimicrobial. Generally, an antimicrobial refers to a substance that kills or inhibits the growth of microorganisms such as bacteria, fungi, virus, or protozoans. Antimicrobial drugs either kill microbes (microbicidal) or prevent the growth of microbes (microbiostatic). There are mainly two classes of antimicrobial drugs, those obtained from natural sources (e.g., antibiotics, protein synthesis inhibitors (such as aminoglycosides, macrolides, tetracyclines, chloramphenicol, polypeptides)) and synthetic agents (e.g., sulphonamides, cotrimoxazole, quinolones). In some instances, the antimicrobial drug is an antibiotic, anti-viral, anti-fungal, anti-malarial, anti-tuberculosis drug, anti-leprotic, or anti-protozoal.

Antibiotics are generally used to treat bacterial infections. Antibiotics may be divided into two categories: bactericidal antibiotics and bacteriostatic antibiotics. Generally, bactericidals may kill bacteria directly where bacteriostatics may prevent them from dividing. Antibiotics may be derived from living organisms or may include synthetic antimicrobials, such as the sulfonamides. Antibiotics may include aminoglycosides, such as amikacin, gentamicin, kanamycin, neomycin, netilmicin, tobramycin, and paromomycin. Alternatively, antibiotics may be ansamycins (e.g., geldanamycin, herbimycin), cabacephems (e.g., loracarbef), carbapenems (e.g., ertapenem, doripenem, imipenem, cilastatin, meropenem), glycopeptides (e.g., teicoplanin, vancomycin, telavancin), lincosamides (e.g., clindamycin, lincomycin, daptomycin), macrolides (e.g., azithromycin, clarithromycin, dirithromycin, erythromycin, roxithromycin, troleandomycin, telithromycin, spectinomycin, spiramycin), nitrofurans (e.g., furazolidone, nitrofurantoin), and polypeptides (e.g., bacitracin, colistin, polymyxin B).

In some instances, the antibiotic therapy includes cephalosporins such as cefadroxil, cefazolin, cefalotin, cefalexin, cefaclor, cefamandole, cefoxitin, cefprozil, cefuroxime, cefixime, cefdinir, cefditoren, cefoperazone, cefotaxime, cefpodoxime, ceftazidime, ceftibuten, ceftizoxime, ceftriaxone, cefepime, ceftaroline fosamil, and ceftobiprole.

The antibiotic therapy may also include penicillins. Examples of penicillins include amoxicillin, ampicillin, azlocillin, carbenicillin, cloxacillin, dicloxacillin, flucloxacillin, mezlocillin, methicillin, nafcillin, oxacillin, penicillin g, penicillin v, piperacillin, temocillin, and ticarcillin.

Alternatively, quinolines may be used to treat a bacterial infection. Examples of quinilones include ciprofloxacin, enoxacin, gatifloxacin, levofloxacin, lomefloxacin, moxifloxacin, nalidixic acid, norfloxacin, ofloxacin, trovafloxacin, grepafloxacin, sparfloxacin, and temafloxacin.

In some instances, the antibiotic therapy comprises a combination of two or more therapies. For example, amoxicillin and clavulanate, ampicillin and sulbactam, piperacillin and tazobactam, or ticarcillin and clavulanate may be used to treat a bacterial infection.

Sulfonamides may also be used to treat bacterial infections. Examples of sulfonamides include, but are not limited to, mafenide, sulfonamidochrysoidine, sulfacetamide, sulfadiazine, silver sulfadiazine, sulfamethizole, sulfamethoxazole, sulfanilimide, sulfasalazine, sulfisoxazole, trimethoprim, and trimethoprim-sulfamethoxazole (co-trimoxazole) (tmp-smx).

Tetracyclines are another example of antibiotics. Tetracyclines may inhibit the binding of aminoacyl-tRNA to the mRNA-ribosome complex by binding to the 30S ribosomal subunit in the mRNA translation complex. Tetracyclines include demeclocycline, doxycycline, minocycline, oxytetracycline, and tetracycline. Additional antibiotics that may be used to treat bacterial infections include arsphenamine, chloramphenicol, fosfomycin, fusidic acid, linezolid, metronidazole, mupirocin, platensimycin, quinupristin/dalfopristin, rifaximin, thiamphenicol, tigecycline, tinidazole, clofazimine, dapsone, capreomycin, cycloserine, ethambutol, ethionamide, isoniazid, pyrazinamide, rifampicin, rifamycin, rifabutin, rifapentine, and streptomycin.

Antiviral therapies are a class of medication used specifically for treating viral infections. Like antibiotics, specific antivirals are used for specific viruses. They are relatively harmless to the host, and therefore can be used to treat infections. Antiviral therapies may inhibit various stages of the viral life cycle. For example, an antiviral therapy may inhibit attachment of the virus to a cellular receptor. Such antiviral therapies may include agents that mimic the virus associated protein (VAP and bind to the cellular receptors. Other antiviral therapies may inhibit viral entry, viral uncoating (e.g., amantadine, rimantadine, pleconaril), viral synthesis, viral integration, viral transcription, or viral translation (e.g., fomivirsen). In some instances, the antiviral therapy is a morpholino antisense. Antiviral therapies should be distinguished from viricides, which actively deactivate virus particles outside the body.

Many of the antiviral drugs available are designed to treat infections by retroviruses, mostly HIV. Antiretroviral drugs may include the class of protease inhibitors, reverse transcriptase inhibitors, and integrase inhibitors. Drugs to treat HIV may include a protease inhibitor (e.g., invirase, saquinavir, kaletra, lopinavir, lexiva, fosamprenavir, norvir, ritonavir, prezista, duranavir, reyataz, viracept), integrase inhibitor (e.g., raltegravir), transcriptase inhibitor (e.g., abacavir, ziagen, agenerase, amprenavir, aptivus, tipranavir, crixivan, indinavir, fortovase, saquinavir, Intelence™, etravirine, isentress, viread), reverse transcriptase inhibitor (e.g., delavirdine, efavirenz, epivir, hivid, nevirapine, retrovir, AZT, stuvadine, truvada, videx), fusion inhibitor (e.g., fuzeon, enfuvirtide), chemokine coreceptor antagonist (e.g., selzentry, emtriva, emtricitabine, epzicom, or trizivir). Alternatively, antiretroviral therarapies may be combination therapies, such as atripla (e.g., efavirenz, emtricitabine, and tenofovira disoproxil fumarate) and completer (embricitabine, rilpivirine, and tenofovir disoproxil fumarate). Herpes viruses, which may cause cold sores and genital herpes, are usually treated with the nucleoside analogue acyclovir. Viral hepatitis (A-E) are caused by five unrelated hepatotropic viruses and are also commonly treated with antiviral drugs depending on the type of infection. Influenza A and B viruses are important targets for the development of new influenza treatments to overcome the resistance to existing neuraminidase inhibitors such as oseltamivir.

In some instances, the antiviral therapy may comprise a reverse transcriptase inhibitor. Reverse transcriptase inhibitors may be nucleoside reverse transcriptase inhibitors or non-nucleoside reverse transcriptase inhibitors. Nucleoside reverse transcriptase inhibitors may include, but are not limited to, combivir, emtriva, epivir, epzicom, hivid, retrovir, trizivir, truvada, videx ec, videx, viread, zerit, and ziagen. Non-nucleoside reverse transcriptase inhibitors may comprise edurant, intelence, rescriptor, sustiva, and viramune (immediate release or extended release).

Protease inhibitors are another example of antiviral drugs and may include, but are not limited to, agenerase, aptivus, crixivan, fortovase, invirase, kaletra, lexiva, norvir, prezista, reyataz, and viracept. Alternatively, the antiviral therapy may comprise a fusion inhibitor (e.g., enfuviride) or an entry inhibitor (e.g., maraviroc).

Additional examples of antiviral drugs include abacavir, acyclovir, adefovir, amantadine, amprenavir, ampligen, arbidol, atazanavir, atripla, boceprevir, cidofovir, combivir, darunavir, delavirdine, didanosine, docosanol, edoxudine, efavirenz, emtricitabine, enfuvirtide, entecavir, famciclovir, fomivirsen, fosamprenavir, foscarnet, fosfonet, fusion inhibitors, ganciclovir, ibacitabine, imunovir, idoxuridine, imiquimod, indinavir, inosine, integrase inhibitor, interferons (e.g., interferon type I, II, III), lamivudine, lopinavir, loviride, maraviroc, moroxydine, methisazone, nelfinavir, nevirapine, nexavir, nucleoside analogues, oseltamivir, peginterferon alfa-2a, penciclovir, peramivir, pleconaril, podophyllotoxin, protease inhibitors, raltegravir, reverse transcriptase inhibitors, ribavirin, rimantadine, ritonavir, pyramidine, saquinavir, stavudine, tea tree oil, tenofovir, tenofovir disoproxil, tipranavir, trifluridine, trizivir, tromantadine, truvada, valaciclovir, valganciclovir, vicriviroc, vidarabine, viramidine, zalcitabine, zanamivir, and zidovudine.

An antifungal drug is medication that may be used to treat fungal infections such as athlete's foot, ringworm, candidiasis (thrush), serious systemic infections such as cryptococcal meningitis, and others. Antifungals work by exploiting differences between mammalian and fungal cells to kill off the fungal organism. Unlike bacteria, both fungi and humans are eukaryotes. Thus, fungal and human cells are similar at the molecular level, making it more difficult to find a target for an antifungal drug to attack that does not also exist in the infected organism.

Antiparasitics are a class of medications which are indicated for the treatment of infection by parasites, such as nematodes, cestodes, trematodes, infectious protozoa, and amoebae. Like antifungals, they must kill the infecting pest without serious damage to the host.

Methods of the disclosure can be implemented by way of systems, kits, libraries, or a combination thereof. The methods of the present disclosure may comprise one or more systems. Systems of the disclosure can be implemented by way of kits, libraries, or both. A system may comprise one or more components to perform any of the methods or any of the operations of the methods disclosed herein. For example, a system may comprise one or more kits, devices, libraries, or a combination thereof. A system may comprise one or more sequencers, processors, memory locations, computers, computer systems, or a combination thereof. A system may comprise a transmission device.

A kit may comprise various reagents for implementing various operations disclosed herein, including sample processing and/or analysis operations. A kit may comprise instructions for implementing at least some of the operations disclosed herein. A kit may comprise one or more capture probes, one or more beads, one or more labels, one or more linkers, one or more devices, one or more reagents, one or more buffers, one or more samples, one or more databases, or a combination thereof.

Figure 7:
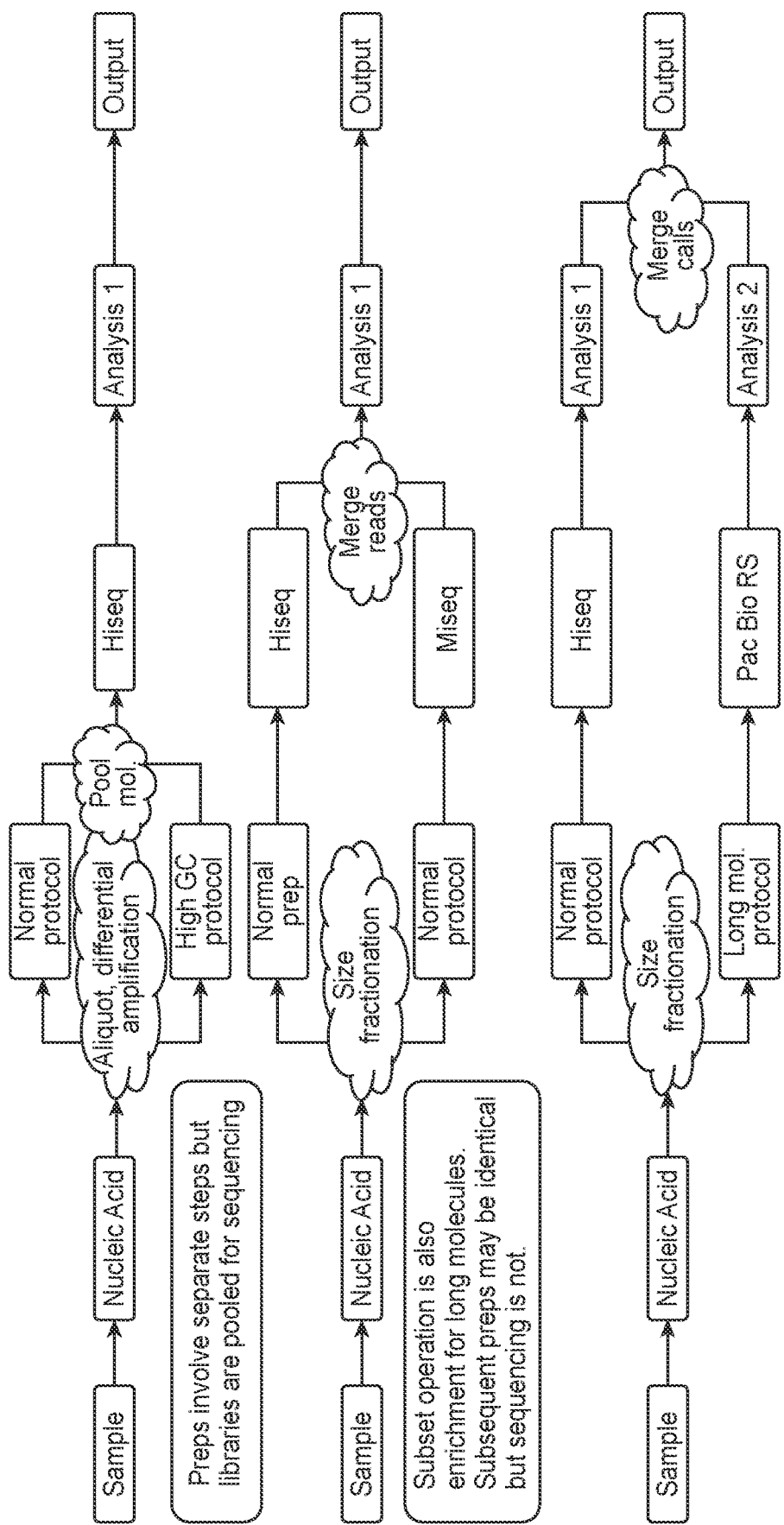
FIG. 7 depicts examples of assay workflows described herein.
Figure 13:
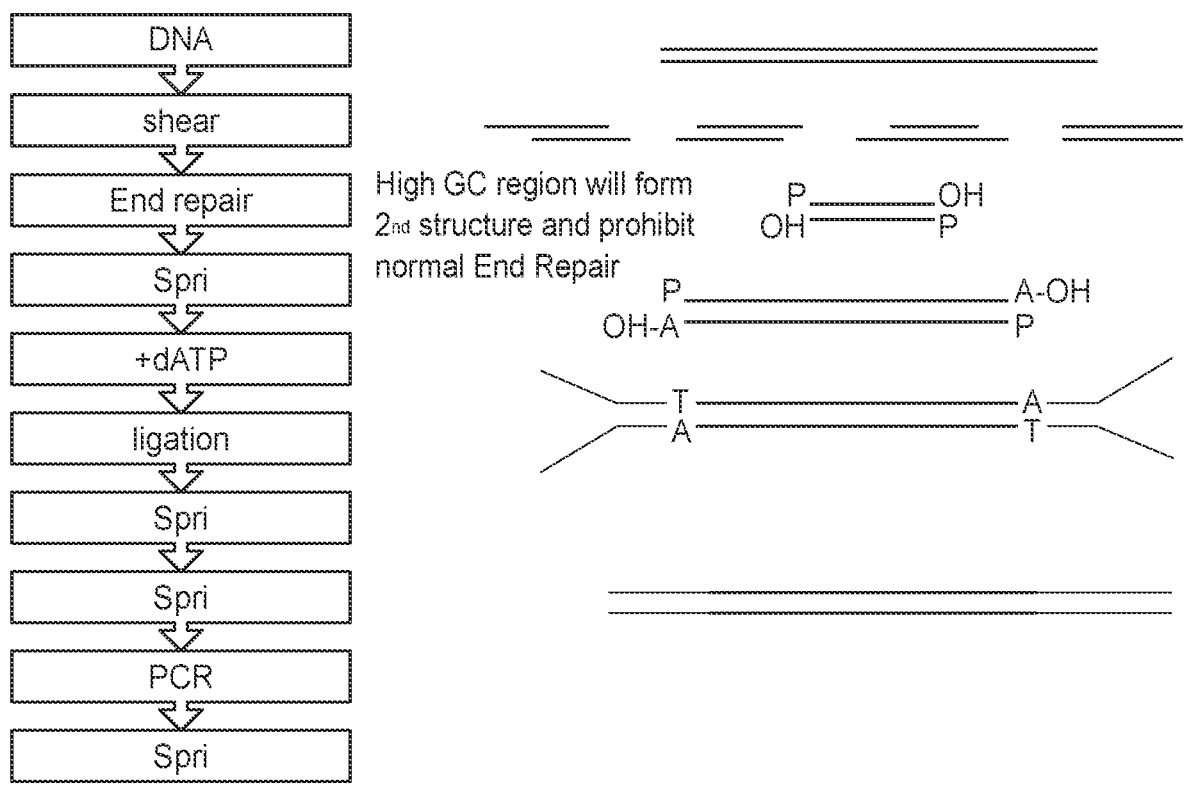
FIG. 13 depicts a schematic of a nucleic acid library construction workflow.

A library may comprise one or more capture probes. A library may comprise one or more subsets of nucleic acid molecules. A library may comprise one or more databases. A library may be produced or generated from any of the methods, kits, or systems disclosed herein. A database library may be produced from one or more databases. A method for producing one or more libraries may comprise (a) aggregating information from one or more databases to produce an aggregated data set; (b) analyzing the aggregated data set; and (c) producing one or more database libraries from the aggregated data set. FIG. 13 provides an example of a library construction workflow. In some cases, a library may be pooled, FIG. 7.

Computer Systems

Figure 5:
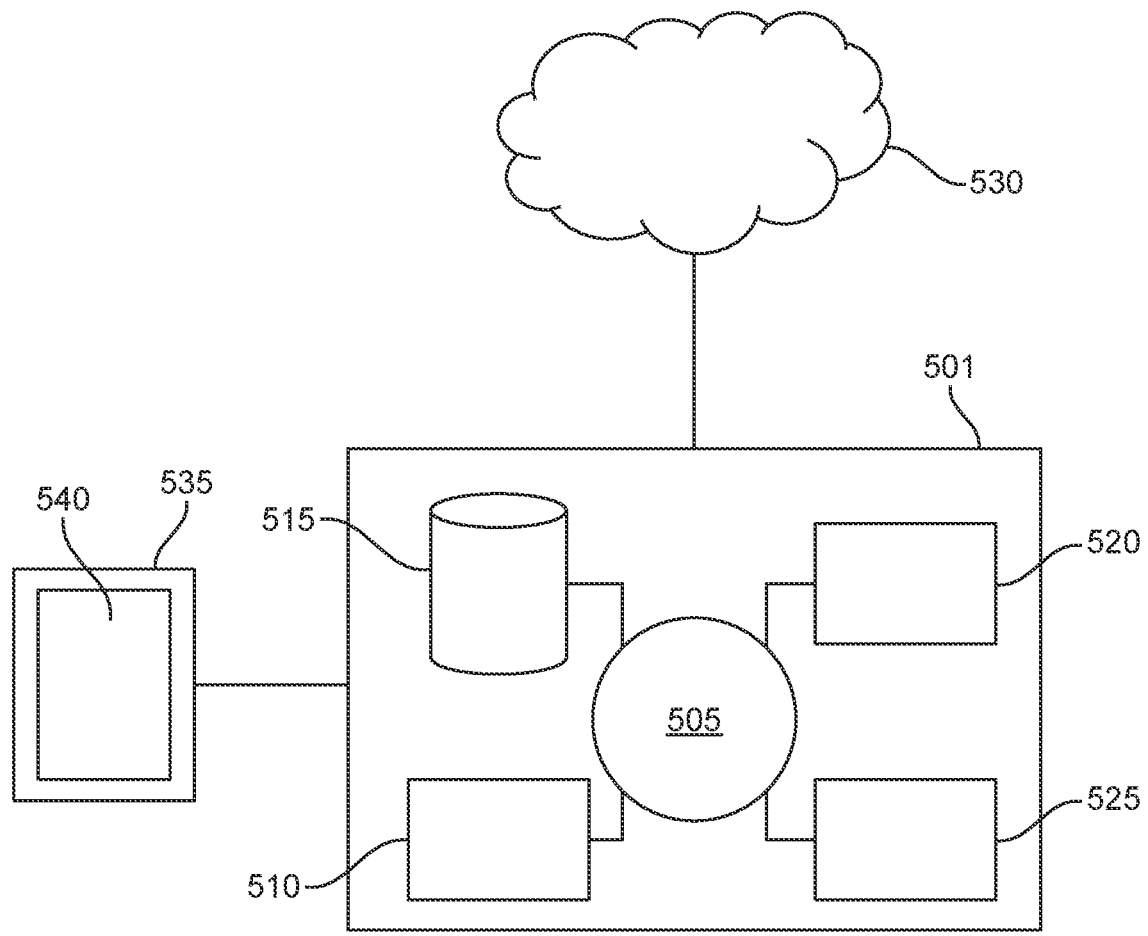
FIG. 5 shows a computer system that is programmed or otherwise configured to implements methods of the present disclosure.

The present disclosure provides computer systems that are programmed to implement methods of the disclosure. FIG. 5 shows a computer system 501 that is programmed or otherwise configured to map and/or align sequence reads to identify a source of nucleic acid molecules (e.g., human or non-human, host or non-host), identify one or more features (e.g., genetic variants), or any combination thereof. The computer system 501 can regulate various aspects of processing sequencing information as provided in the present disclosure, such as, for example, aligning sequence reads to one or more reference sequences to identify a source of a nucleic acid sequence in a biological sample. The computer system 501 can be an electronic device of a user or a computer system that is remotely located with respect to the electronic device. The electronic device can be a mobile electronic device.

The computer system 501 includes a central processing unit (CPU, also "processor" and "computer processor" herein) 505, which can be a single core or multi core processor, or a plurality of processors for parallel processing. The computer system 501 also includes memory or memory location 510 (e.g., random-access memory, read-only memory, flash memory), electronic storage unit 515 (e.g., hard disk), communication interface 520 (e.g., network adapter) for communicating with one or more other systems, and peripheral devices 525, such as cache, other memory, data storage and/or electronic display adapters. The memory 510, storage unit 515, interface 520 and peripheral devices 525 are in communication with the CPU 505 through a communication bus (solid lines), such as a motherboard. The storage unit 515 can be a data storage unit (or data repository) for storing data. The computer system 501 can be operatively coupled to a computer network ("network") 530 with the aid of the communication interface 520. The network 530 can be the Internet, an internet and/or extranet, or an intranet and/or extranet that is in communication with the Internet. The network 530 in some cases is a telecommunication and/or data network. The network 530 can include one or more computer servers, which can enable distributed computing, such as cloud computing. The network 530, in some cases with the aid of the computer system 501, can implement a peer-to-peer network, which may enable devices coupled to the computer system 501 to behave as a client or a server.

The CPU 505 can execute a sequence of machine-readable instructions, which can be embodied in a program or software. The instructions may be stored in a memory location, such as the memory 510. The instructions can be directed to the CPU 505, which can subsequently program or otherwise configure the CPU 505 to implement methods of the present disclosure. Examples of operations performed by the CPU 505 can include fetch, decode, execute, and writeback.

The CPU 505 can be part of a circuit, such as an integrated circuit. One or more other components of the system 501 can be included in the circuit. In some cases, the circuit is an application specific integrated circuit (ASIC).

The storage unit 515 can store files, such as drivers, libraries and saved programs. The storage unit 515 can store user data, e.g., user preferences and user programs. The computer system 501 in some cases can include one or more additional data storage units that are external to the computer system 501, such as located on a remote server that is in communication with the computer system 501 through an intranet or the Internet.

The computer system 501 can communicate with one or more remote computer systems through the network 530. For instance, the computer system 501 can communicate with a remote computer system of a user (e.g., a healthcare provider). Examples of remote computer systems include personal computers (e.g., portable PC), slate or tablet PC's (e.g., Apple® iPad, Samsung® Galaxy Tab), telephones, Smart phones (e.g., Apple® iPhone, Android-enabled device, Blackberry®), or personal digital assistants. The user can access the computer system 501 via the network 1130.

Methods as described herein can be implemented by way of machine (e.g., computer processor) executable code stored on an electronic storage location of the computer system 501, such as, for example, on the memory 510 or electronic storage unit 515. The machine executable or machine readable code can be provided in the form of software. During use, the code can be executed by the processor 505. In some cases, the code can be retrieved from the storage unit 515 and stored on the memory 510 for ready access by the processor 505. In some situations, the electronic storage unit 515 can be precluded, and machine-executable instructions are stored on memory 510.

The code can be pre-compiled and configured for use with a machine having a processer adapted to execute the code, or can be compiled during runtime. The code can be supplied in a programming language that can be selected to enable the code to execute in a pre-compiled or as-compiled fashion.

Aspects of the systems and methods provided herein, such as the computer system 501, can be embodied in programming. Various aspects of the technology may be thought of as "products" or "articles of manufacture" typically in the form of machine (or processor) executable code and/or associated data that is carried on or embodied in a type of machine readable medium. Machine-executable code can be stored on an electronic storage unit, such as memory (e.g., read-only memory, random-access memory, flash memory) or a hard disk. "Storage" type media can include any or all of the tangible memory of the computers, processors or the like, or associated modules thereof, such as various semiconductor memories, tape drives, disk drives and the like, which may provide non-transitory storage at any time for the software programming. All or portions of the software may at times be communicated through the Internet or various other telecommunication networks. Such communications, for example, may enable loading of the software from one computer or processor into another, for example, from a management server or host computer into the computer platform of an application server. Thus, another type of media that may bear the software elements includes optical, electrical and electromagnetic waves, such as used across physical interfaces between local devices, through wired and optical landline networks and over various air-links. The physical elements that carry such waves, such as wired or wireless links, optical links or the like, also may be considered as media bearing the software. As used herein, unless restricted to non-transitory, tangible "storage" media, terms such as computer or machine "readable medium" refer to any medium that participates in providing instructions to a processor for execution.

Hence, a machine readable medium, such as computer-executable code, may take many forms, including but not limited to, a tangible storage medium, a carrier wave medium or physical transmission medium. Non-volatile storage media include, for example, optical or magnetic disks, such as any of the storage devices in any computer(s) or the like, such as may be used to implement the databases, etc. shown in the drawings. Volatile storage media include dynamic memory, such as main memory of such a computer platform. Tangible transmission media include coaxial cables; copper wire and fiber optics, including the wires that comprise a bus within a computer system. Carrier-wave transmission media may take the form of electric or electromagnetic signals, or acoustic or light waves such as those generated during radio frequency (RF) and infrared (IR) data communications. Common forms of computer-readable media therefore include for example: a floppy disk, a flexible disk, hard disk, magnetic tape, any other magnetic medium, a CD-ROM, DVD or DVD-ROM, any other optical medium, punch cards paper tape, any other physical storage medium with patterns of holes, a RAM, a ROM, a PROM and EPROM, a FLASH-EPROM, any other memory chip or cartridge, a carrier wave transporting data or instructions, cables or links transporting such a carrier wave, or any other medium from which a computer may read programming code and/or data. Many of these forms of computer readable media may be involved in carrying one or more sequences of one or more instructions to a processor for execution.

The computer system 501 can include or be in communication with an electronic display 535 that comprises a user interface (UI) 540 for providing, for example, one or more biomedical reports comprising one or more sets of data selected from the group consisting of: (i) candidate tumor neoantigens, (ii) detected non-human species, (iii) detected CDR3 sequences, and any combination thereof. Examples of UI's include, without limitation, a graphical user interface (GUI) and web-based user interface.

Methods and systems of the present disclosure can be implemented by way of one or more algorithms. An algorithm can be implemented by way of software upon execution by the central processing unit 505. The algorithm can, for example, map and/or align sequence reads, call variants, annotate sequence information, or any combination thereof.

EXAMPLES

Example 1. Preparation of Genomic DNA

The following operations were used to prepare subsets of nucleic acid molecules from a sample comprising genomic DNA:

1. A sample comprising genomic DNA is sheared with M220 for 15-35 seconds.
2. The fragmented gDNA was purified with SPRI beads after ligation (ratio of the volume of SPRI beads to the DNA sample was 1) and the DNA was eluted into 100 µL of elution buffer (EB).
3. 50 µL of SPRI beads were added to the 100 µL of DNA.
4. The supernatant was transferred to a new tube.
5. The DNA from the remaining bead bound DNA was eluted. This eluted DNA was called the long insert.
6. 10 µL of SPRI beads were added to the supernatant from Operation 4.
7. The supernatant from Operation 6 was transferred to a new tube.
8. The DNA from the remaining bead bound DNA of Operation 6 was eluted. This eluted DNA was called the mid insert.
9. 20 µL of SPRI beads were added to the supernatant from Operation 7.
10. The supernatant from Operation 9 was transferred to a new tube.
11. The DNA from the remaining bead bound DNA of Operation 9 was eluted. This eluted DNA was called the short insert.

Example 2. Obtaining a Biological Sample

Subjects with evaluable metastatic cancer undergo resection of tumor. Lymphocytes from the tumor, tumor infiltrating lymphocytes (TILs), are grown and expanded. Multiple individual fragments or multiple individual cultures of TILs are grown. Individual cultures are separately expanded and when a sufficient yield of TIL (approximately $10^8$ cells) is expanded from each culture, the TIL are cryopreserved and aliquots taken for immunologic testing. An aliquot of the original tumor is subjected to exomic and transcriptome sequencing to identify mutations uniquely present in the tumor as compared to normal cells. Sequencing also identifies the presence and identity of non-human genomes including microbes.

Example 3. Extracting Genomic Material from the Biological Sample

Genomic DNA (gDNA) and total RNA are purified from various tumors and matched normal apheresis samples using the QIAGEN AllPrep DNA/RNA kit (cat #80204) following manufacturer's suggestions. A tumor sample is formalin-fixed, paraffin-embedded (FFPE) and gDNA is extracted using the Covaris truXTRAC™ FFPE DNA kit as directed by the manufacturer.

Example 4. Sequencing Analysis of the Biological Sample

Whole-exome library construction and exon capture of approximately 20,000 coding genes is prepared using Agilent Technologies SureSelectXT Target Enrichment System (cat #5190-8646) for paired-end libraries coupled with Human All Exon V6 RNA bait (cat #5190-8863) (Agilent Technologies, Santa Clara, Calif., USA) and Bacterial RNA bait. Whole-exome sequencing (WES) libraries are subsequently sequenced on a NextSeq 500 desktop sequencer (Illumina, San Diego, Calif., USA). The library is prepped using 3 μg gDNA from fresh tumor tissue samples and 200 ng gDNA from the FFPE tumor sample following manufacturer's protocol. Paired-end sequencing is done with an Illumina High-output flow cell kit (300 cycles) (cat #FC-404-2004). The Tu-1, Tu-2A and Tu-2B samples are run initially on v1 of the reagent/flow cell kit, and a subsequent run of the same library prep is performed using v2 of the reagent/flow cell kit. The tumor sample is run on the v2 reagent/flow cell kit. The mean sequencing depth and percentage of tumor in each sample (tumor purity) are determined, as estimated with the bioinformatics program Allele-Specific Copy Number Analysis of Tumors (ASCAT) 1. RNA-seq libraries are prepared using 2 μg of total RNA with the Illumina TruSeq RNA Stranded library prep kit following the manufacturer's protocol. RNA-seq libraries are paired-end sequenced on a NextSeq 500 desktop sequencer (Illumina, San Diego, Calif., USA). Alignment, processing and variant calling For WES, alignments are performed using novoalign MPI from novocraft (http://www.novocraft.com/) to human genome build hg19. Duplicates are marked using Picard's MarkDuplicates tool. In/del realignment and base recalibration is carried out according to the GATK best practices workflow (https://www.broadinstitute.org/gatk/). Post cleanup of data, samtools (http://samtools.sourceforge.net) is used to create pileup files and Varscan2 (http://varscan.sourceforge.net) is used to call somatic variants using the following criteria: tumor and normal read counts of 10 or greater, variant allele frequency of 10% or greater and tumor variant reads of 4 or more. These variants are then annotated using Annovar (http://annovar.openbioinformatics.org). For RNA-seq, alignments are performed using the STAR (https://github.com/alexdobin/STAR) two pass method to human genome build hg19. Duplicates are marked using Picard's MarkDuplicates tool. Reads are split and trimmed using GATK SplitNTrim tool. After which In/del realignment and base recalibration are performed using GATK toolbox. A pileup file is created using the final recalibrated bam file and samtools mpileup. Finally, variants are called using Varscan2.

Example 5: Sequence Alignment of Non-Human Genomes

Genomic information extracted from the sequencing analysis is aligned to the ribosomal RNA gene, 16S, genome reference. Reads that perfectly matched to the 16S gene are identified. Capture probes which are designed to hybridize to the shared regions of the 16S gene can be used to capture nucleic acid molecules from a wide variety of species, even species which have yet to be identified and characterized. Captured molecules whose sequences extend from these shared regions into the variable regions, are assigned to their source species based on the sequence from the variable region part.

Example 6. Shear Time and Fragment Sizes

Figure 10:
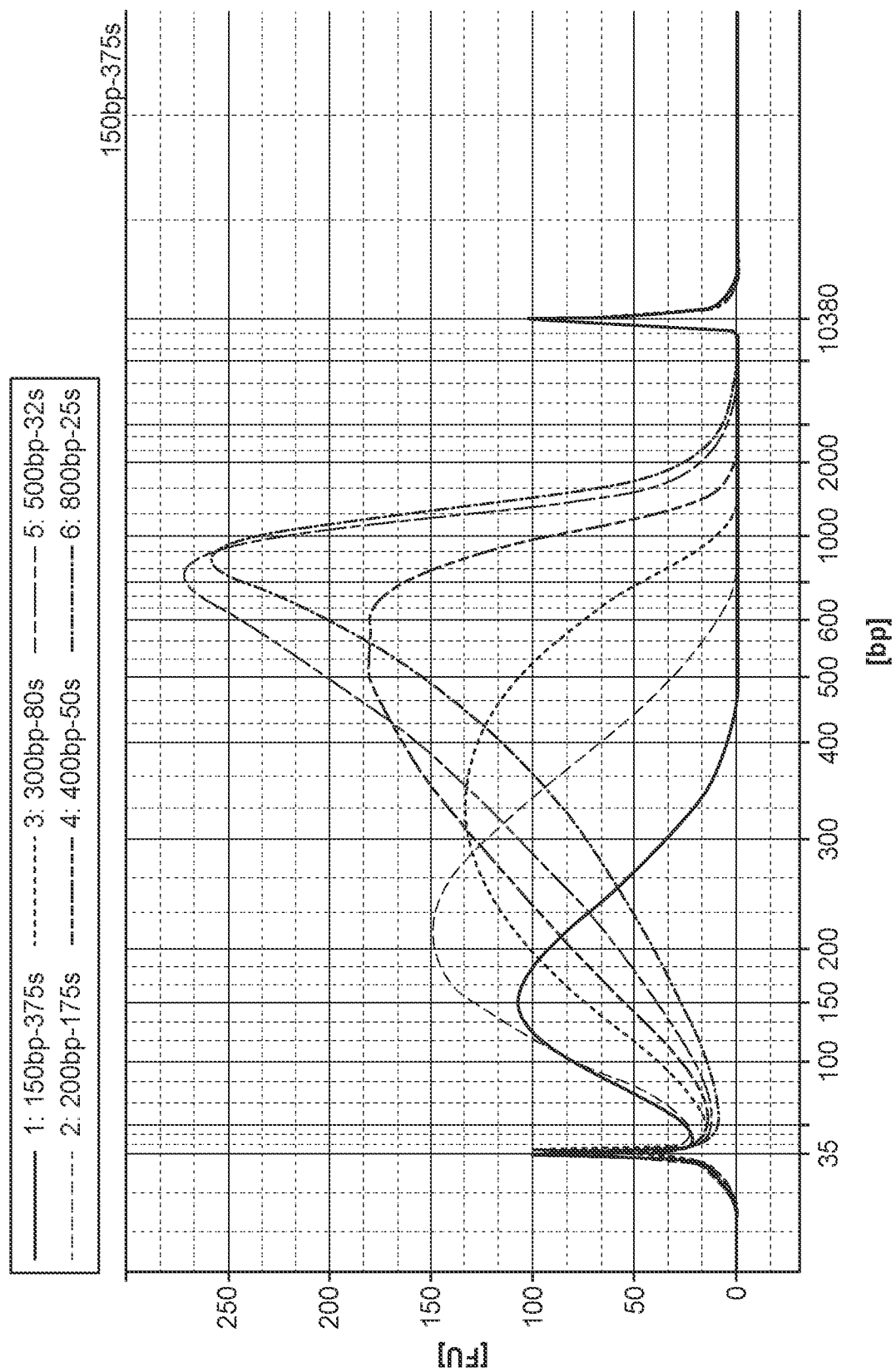
FIG. 10 shows effects of shear time on fragment size.

Genomic DNA (gDNA) was sheared by varying the shear time of a Covaris setting. The gDNA fragments produced by various shear times was then analyzed. Results are shown in FIG. 10 and Table 1.

TABLE 1

| Shear time and mean fragment size | | |
| --- | --- | --- |
| Number | Shear Time (seconds) | Mean Fragment Size (base pairs) |
| 1 | 375 | 150 |
| 2 | 175 | 200 |
| 3 | 80 | 200 |
| 4 | 40 | 400 |
| 5 | 32 | 500 |
| 6 | 25 | 800 |

Example 7. Bead Ratio and Fragment Size

Figure 11:
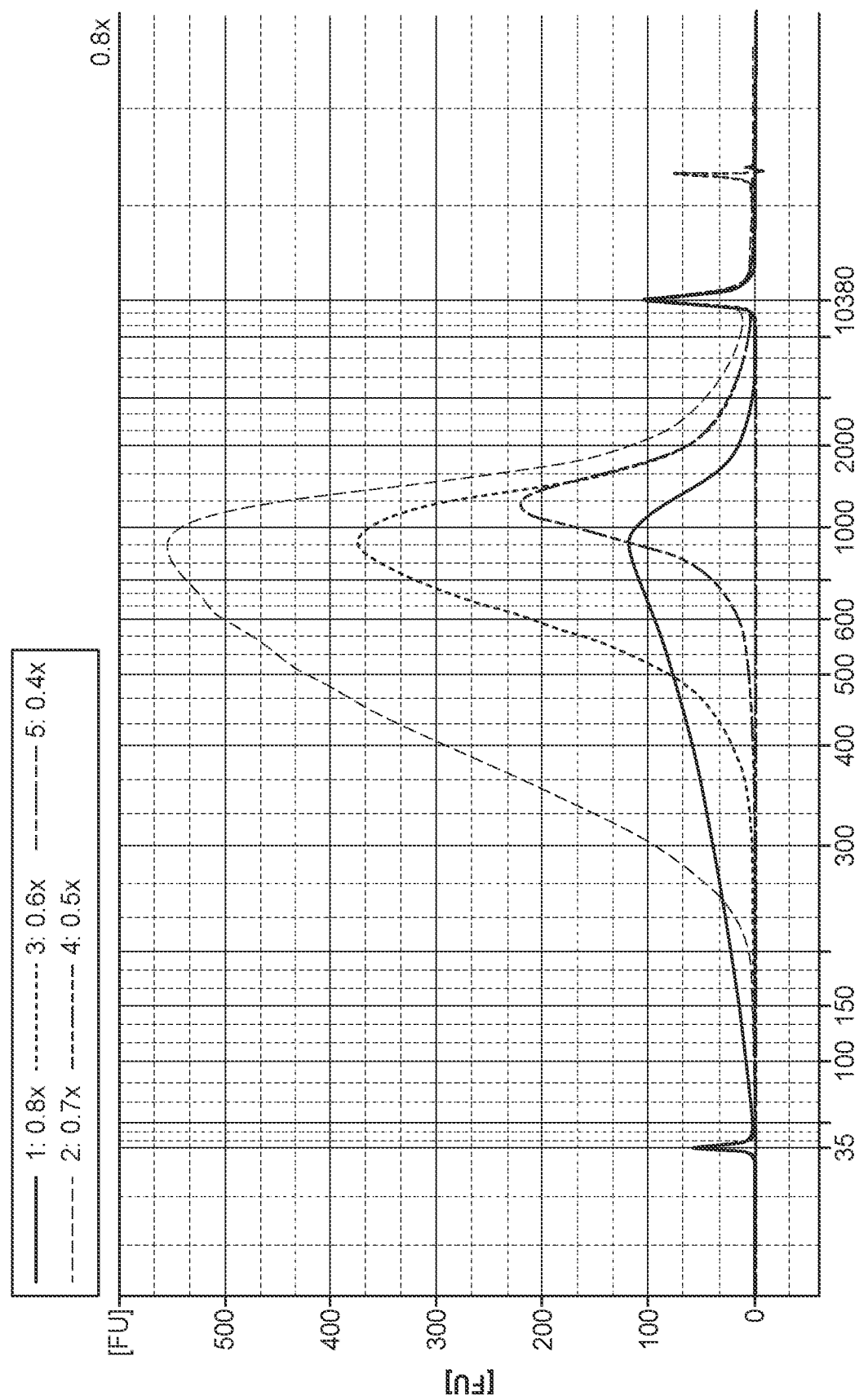
FIG. 11 shows effects of bead ratio on fragment size.

The ratio of the volume of beads to the volume of the nucleic acid sample was varied and the effects of these ratios on mean fragment size was analyzed. As can be shown in FIG. 11, varying the ratio of the volume of the volume of the beads to the volume of the nucleic acid sample from 0.8 (line 1), 0.7 (line 2), 0.6 (line 3), 0.5 (line 4) and 0.4 (line 5) resulted in a shift in the mean size of the DNA fragments. Generally, it appeared that the lower the ratio, then the larger the mean fragment size.

Example 8. Ligation Reactions and Fragment Size

Figure 12:
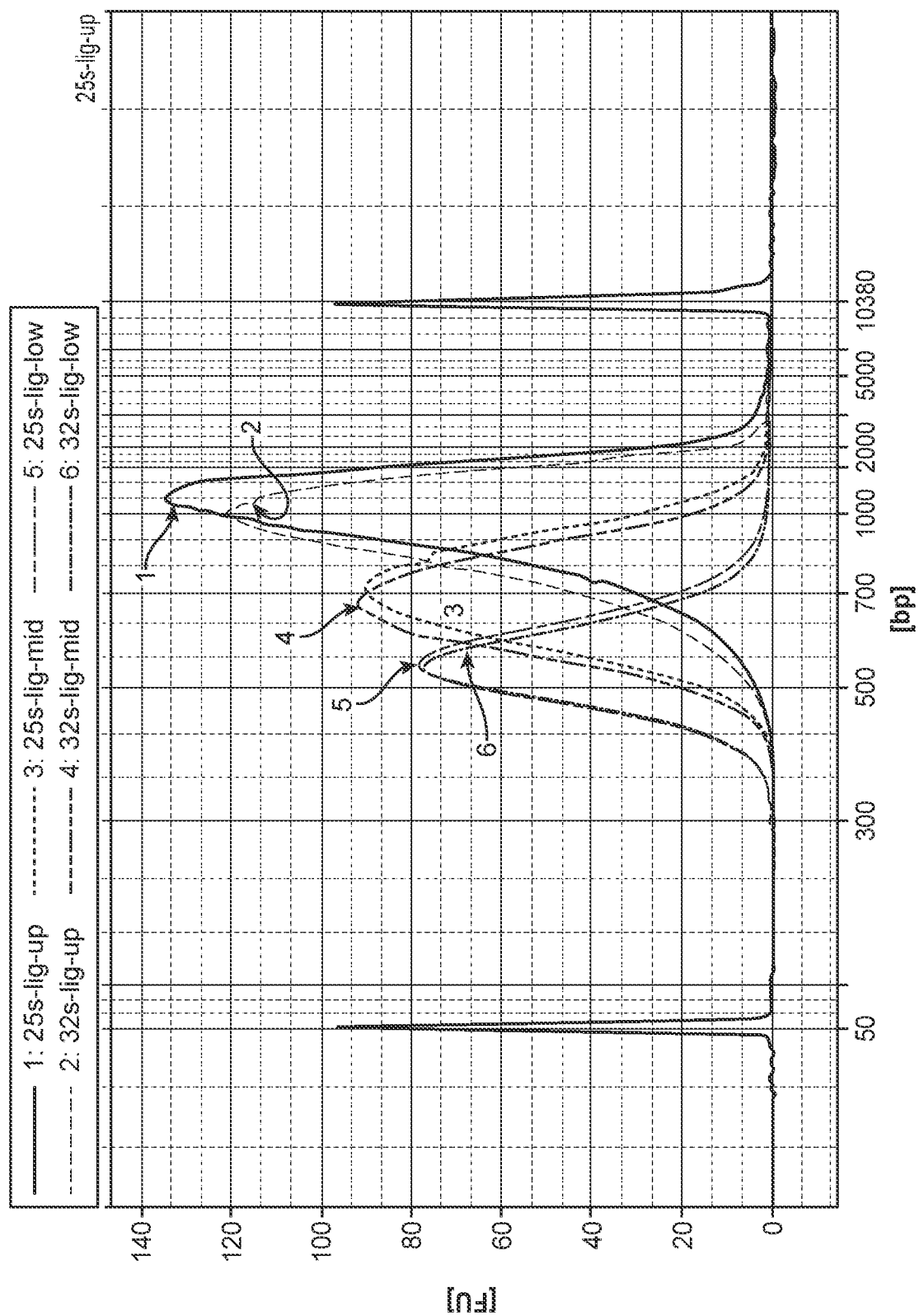
FIG. 12 shows effects of shear time on fragment size.

A combination of two different shear times and three different ligation reactions were conducted on a nucleic acid sample. Sample 1 was sheared for 25 seconds and a ligation reaction was performed on the long insert DNA. Sample 2 was sheared for 32 seconds and a ligation reaction was performed on the long insert DNA. Sample 3 was sheared for 25 seconds and a ligation reaction was performed on the mid insert DNA. Sample 4 was sheared for 32 seconds and a ligation reaction was performed on the mid insert DNA. Sample 5 was sheared for 25 seconds and a ligation reaction was performed on the short insert DNA. Sample 6 was sheared for 32 seconds and a ligation reaction was performed on the short insert DNA. FIG. 12 shows the mean fragment size for the six reactions.

Example 9. Capture of Nucleic Acids of Interest

A nucleic acid sample is obtained from a subject. The sample can be divided in to two separate samples and each separate sample can be subjected to different pools of probes and conditions. A first pool of biotinylated capture probes is be generated by combining an Agilent Clinical Research Exome Kit (based on exomes in GRCh37 reference genome) with additional probes of interest including exome regions corresponding to the GRCh38 reference sequence, HLA specific probes, T-cell receptor and B-cell receptor recombination specific probes (i.e. regions corresponding to V(D)J regions), regions of microsatellite instability, and oncovirus sequences. Additional probes are titrated into the pool to tune the relative capture rate of nucleic acids. This can be beneficial for sequencing reactions downstream to increase sequencing depth or sensitivity for a set of captured nucleic acids. A second pool of probes (e.g., a "boost set" of probes targeting specific sequences, or a subset of sequences) can capture nucleic acids with sequences that are difficult to capture. Probes of the boost set can include exomes of the GRCh37 and GRCh38 reference sequences that have high GC content, probes related to cancer therapies, additional T-cell receptor and B-cell recombination specific probes. Nucleic acid molecules captured by the first pool and nucleic acid molecules captured by the second pool are combined to create a combined pool of capture probes and captured nucleic acids. The combined pool can be created by combining different ratios of the two pools of captured molecules in order to tune the relative amounts of captured nucleic acids corresponding to each pool. This can be beneficial for sequencing reactions downstream to increase depth or sensitivity for a set of capture nucleic acids. The hybridized capture probes and capture nucleic acid are incubated with magnetic streptavidin beads. A magnetic separator is placed on the outside of the tube containing the sample and the capture probes are allowed to immobilize the magnetic streptavidin beads. The liquid is decanted off and additional buffer is added to wash the beads and remove any unbound nucleic acids. The captured nucleic acids are subjected to amplification reactions to append adapters for further downstream sequencing reactions.

Example 10. Identification of Microbiome and Oncoviruses

A nucleic acid sample is obtained from a subject. The sample can be divided in to two separate samples and each separate sample can be subjected to different pools of probes and conditions. A first pool of biotinylated capture probes is be generated by combining an Agilent Clinical Research Exome Kit (based on exomes in GRCh37 reference genome) with additional probes of interest including exome regions corresponding to the GRCh38 reference sequence, probes with homology to 16S rRNA regions of bacterial, fungal, archaea and protist genes, including genes of *Helicobacter pylori* and *Fusobacterium*, probes to viral genes (including Human Papilloma virus, Hepatitis B Virus, Hepatitis C Virus), and probes to genes related to pathogenicity. Additional probes are titrated into the pool to tune the relative capture rate of nucleic acids. A second pool of probes (e.g., a "boost set" of probes targeting specific sequences, or a subset of sequences) can capture nucleic acids with sequences that are difficult to capture. Probes of the boost set can include exomes of the GRCh37 and GRCh38 reference sequences that have high GC content or low homology to genes due to multiple alternate gene sequences or genes with high mutation rates. Nucleic acid molecules captured by the first pool and nucleic acid molecules captured by the second pool are combined to create a combined pool of nucleic acids. These two pools are combined and titrated in different ratios to increase sensitivity of one pool over the other pool. The hybridized capture probes and capture nucleic acid are incubated with magnetic streptavidin beads. A magnetic separator is placed on the outside of the tube containing the sample and the capture probes and allowed to immobilize the magnetic streptavidin beads. The liquid is decanted off and additional buffer is added to wash the beads and remove any unbound nucleic acids. The captured nucleic acids are subjected to amplification reactions to append adapters for further downstream sequencing reactions. The sequences are aligned with reference sequences to identify the presence of specific microbes in the microbiome of the subject or to identify any disease causing pathogen.

Example 11. Identification or CAR-T Cells

A nucleic acid sample from a subject is obtained. Two pools of probes are generated, with a first pool comprised of biotinylated Agilent Clinical Research Exome Kit probes. A supplement set of biotinylated probes is added to the first pool including sequences to specific to chimeric-antigen-receptors found in CAR-T cells. A second pool of biotinylated capture probes (e.g., a "boost set" of probes targeting specific sequences, or a subset of sequences) contains sequences directed at CAR sequences with high GC content and/or sequences that may have lower overall sequence homology with captured nucleic acids due to mutation or recombination. The sample is divided into two sample pools and a first sample pool is subjected to the first pool of probes and the second sample pool is subjected to the second pool of probes to allow the capture probes to capture nucleic acids from each of the sample pools. The first pool and second pool of probes hybridized to the captured nucleic acids are combined. Magnetic streptavidin beads are added into the mixture and the biotinylated probes are allowed to bind to the beads. A magnetic separator is placed on the outside of the tube containing the sample and the capture probes and allowed to immobilize the magnetic streptavidin beads. The liquid is decanted off and additional buffer is added to wash the beads and remove any unbound nucleic acids. Captured nucleic acids are re-suspended into fresh buffer and subjected to amplification reactions to append adapters and the captured nucleic are subsequently sequenced. Sequences reads are analyzed and aligned against CAR-T gene reference sequences to identify the presence of CAR-T related nucleic acids Example 12: Identification of Segmented Transcriptome Samples are obtained from a subject from different tissue types. The samples are processed by enzymatic digestion to remove DNA, and multiple types RNA molecules (rRNA, tRNA, miRNA). mRNA is left undigested and is subjected to reverse transcription to generate cDNA molecules. A biotinylated probe set with sequence homology to approximately 20,000 genes is generated and mixed with the cDNA sample. Magnetic streptavidin beads are added into the mixture and the biotinylated probes are allowed to bind to the bead. A magnetic separator is placed on the outside of the tube containing the sample and the capture probes and allowed to immobilize the magnetic streptavidin beads. The liquid is decanted off and additional buffer is added to wash the beads and remove any unbound nucleic acids. Captured nucleic acids are re-suspended into fresh buffer and subjected to amplification reactions to append adapters and the captured nucleic are subsequently sequenced. Sequences reads are analyzed and aligned against reference sequence to determine the identity of the genes in each sample and correlated to the tissue type of the sample. Multiple replicate of samples are run in which the biotinylated probes are titrated in different ratios. By analyzing the specific signal of the nucleic acids in relation to the amount of probes provided to the sample, expression level of each gene can be determined. The transcriptome analysis can be run in parallel with exome or genome analysis. Exome or genome probes may be used as a first pool of probes and the cDNA capture probes can be used as second pool. The sample in this case can be split into portions and subjected to DNA specific or mRNA specific reactions. As disclosed in prior examples, the captured nucleic acids can be pooled together and subjected to sequencing reactions to determine the identity of the nucleic acids.

Example 13. Identification and Capture of Cell-Free DNA (cfDNA) Related to Cancer Nucleic acid sample extract from whole blood or serum is obtained. Cells of the blood sample are removed via centrifugation and a cell-free sample is obtained. A biotinylated probe set with sequence homology to approximately 20,000 genes is generated and mixed with the cell-free sample. A first pool of biotinylated capture probes is be generated by combining an Agilent Clinical Research Exome Kit (based on exomes in GRCh37 reference genome) with additional probes of interest including exome regions corresponding to the GRCh38 reference sequence, and probes with homology to genes associated with cancer. Additional probes are titrated into the pool to tune the relative capture rate of nucleic acids. A second pool of probes (e.g., a "boost set" of probes targeting specific sequences, or a subset of sequences) can capture nucleic acids with sequences that are difficult to capture. Probes of the boost set can include exomes of the GRCh37 and GRCh38 reference sequences that have high GC content or low homology to genes due to multiple alternate gene sequences or genes with high mutation rates. Magnetic streptavidin beads are added into the mixture and the biotinylated probes are allowed to bind to the bead. A magnetic separator is placed on the outside of the tube containing the sample and the capture probes and allowed to immobilize the magnetic streptavidin beads. The liquid is decanted off and additional buffer is added to wash the beads and remove any unbound nucleic acids. Captured nucleic acids are re-suspended into fresh buffer and subjected to amplification reactions to append adapters and the captured nucleic are subsequently sequenced. Sequences reads are analyzed and aligned against reference sequence to determine the identity of the genes in each sample. cfDNA analysis can be run in parallel with exome sequencing of genomic DNA by applying genomic DNA to the same or similar probe sets as performed with cfDNA.

While preferred embodiments of the present invention have been shown and described herein, it will be obvious to those skilled in the art that such embodiments are provided by way of example only. It is not intended that the invention be limited by the specific examples provided within the specification. While the invention has been described with reference to the aforementioned specification, the descriptions and illustrations of the embodiments herein are not meant to be construed in a limiting sense. Numerous variations, changes, and substitutions will now occur to those skilled in the art without departing from the invention. Furthermore, it shall be understood that all aspects of the invention are not limited to the specific depictions, configurations or relative proportions set forth herein which depend upon a variety of conditions and variables. It should be understood that various alternatives to the embodiments of the invention described herein may be employed in practicing the invention. It is therefore contemplated that the invention shall also cover any such alternatives, modifications, variations or equivalents. It is intended that the following claims define the scope of the invention and that methods and structures within the scope of these claims and their equivalents be covered thereby.

What is claimed is:

1. A method for detecting the presence of cancer in a subject, comprising:
    (a) providing said biological sample from said human subject, wherein said biological sample of said human subject comprises (i) human nucleic acid molecules derived from said human subject, and (ii) non-human nucleic acid molecules derived from one or more oncoviruses or bacteria associated with cancer;
    (b) enriching said human nucleic acid molecules and said non-human nucleic acid molecules derived from said biological sample, to yield an enriched set of nucleic acid molecules comprising (i) a subset of said human nucleic acids derived from said human subject and (ii) a subset of said non-human nucleic acids derived from one or more oncoviruses or bacteria associated with cancer, wherein said enriching comprises hybridizing said human nucleic acid molecules and said non-human nucleic acid molecules to capture probes, wherein said capture probes comprise (i) a first plurality of probes configured to hybridize to said human nucleic acid molecules and (ii) a second plurality of probes configured to hybridize to said non-human nucleic acid molecules; and
    (c) sequencing said enriched set of nucleic acid molecules to yield sequence information comprising sequences of said enriched set of nucleic acid molecules, wherein said sequences of said enriched set of nucleic acid molecules comprise sequences of (i) human nucleic acids from said biological sample from said human subject and (ii) non-human nucleic acids from said biological sample of said human subject.

2. The method of claim 1, wherein said capture probes comprise biotinylated capture probes.

3. The method of claim 1, wherein (b) further comprises, attaching said capture probes to a support.

4. The method of claim 3, wherein said support comprises an array, a bead, a slide, or a chip.

5. The method of claim 4, wherein said bead is a magnetic bead.

6. The method of claim 4, wherein said bead is a streptavidin bead.

7. The method of claim 1, wherein said concentration of said first plurality of probes and said second plurality of probes are different.

8. The method of claim 1, wherein b) further comprises titrating the relative concentration of said first plurality of probes and said second plurality of probes.

9. The method of claim 1, wherein said first plurality of probes comprises sequences complementary to human exome sequences.

10. The method of claim 1, wherein said first plurality of probes comprises sequences complementary to sequences in a reference genome that comprise a GC content that is higher than average amount in said reference sequence.

11. The method of claim 1, wherein said first plurality of probes comprises sequences complementary to HLA, T-cell receptors, B-cell receptors, or regions of microsatellite instability.

12. The method of claim 1, further comprising aligning said sequences of said enriched set of nucleic acid molecules to a plurality of reference sequences.

13. The method of claim 12, wherein said plurality of reference sequences are derived from two or more species.

14. The method of claim 12, further comprising identifying a source of said human nucleic acids or said non-human nucleic acid based on said aligning.

15. The method of claim 14, further comprising detecting the presence or absence of cancer in a subject based on the identified sources of said non-human nucleic acids.

16. The method of claim 1, wherein said sample is a tumor biopsy.

17. The method of claim 1, wherein said sample is a plasma sample.

18. The method of claim 1, wherein said capture probes perform a capture reaction in solution.

19. The method of claim 18, wherein said capture probes are attached to a solid support after capturing said human nucleic acid molecules and said non-human nucleic acid molecules.

20. The method of claim 19, wherein said solid support comprises an array, a bead, a slide, or a chip.

21. The method of claim 1, wherein said capture probes are attached to a support and perform a capture reaction.

22. The method of claim 21, wherein said support comprises an array, a bead, a slide, or a chip.

23. The method of claim 21, wherein said capture probes are coupled to said support and subsequently capture said human nucleic acid molecules and said non-human nucleic acid molecules.

24. The method of claim 23, wherein said support comprises an array, a bead, a slide, or a chip.

* * * * *